US012655123B2

(12) United States Patent
Li et al.

(10) Patent No.: US 12,655,123 B2
(45) Date of Patent: Jun. 16, 2026

(54) HETEROARYL COMPOUNDS, SOLID FORMS, PREPARATION METHODS AND USES THEREOF

(71) Applicants: InventisBio Co., Ltd., Shanghai (CN); InventisBio LLC, Short Hills, NJ (US)

(72) Inventors: Wei Li, Shanghai (CN); Yanqin Liu, Shanghai (CN); Xing Dai, Short Hills, NJ (US)

(73) Assignees: InventisBio Co., Ltd., Shanghai (CN); InventisBio LLC

( * ) Notice: Subject to any disclaimer, the term of this patent is extended or adjusted under 35 U.S.C. 154(b) by 0 days.

(21) Appl. No.: 19/240,239

(22) Filed: Jun. 17, 2025

(65) Prior Publication Data

US 2025/0313545 A1 Oct. 9, 2025

Related U.S. Application Data

(63) Continuation of application No. 18/211,741, filed on Jun. 20, 2023.

(30) Foreign Application Priority Data

Jun. 20, 2022 (CN) ........................ 202210700943.X

(51) Int. Cl.
*C07D 401/12* (2006.01)

(52) U.S. Cl.
CPC ........ *C07D 401/12* (2013.01); *C07B 2200/05* (2013.01)

(58) Field of Classification Search
CPC .................................................... C07D 401/12
See application file for complete search history.

(56) References Cited

U.S. PATENT DOCUMENTS

| | | | |
|---|---|---|---|
| 8,901,124 B2 | 12/2014 | Hermann et al. |
| 10,000,480 B2 | 6/2018 | Moslin et al. |
| 12,492,184 B2 | 12/2025 | Dai |
| 2024/0025876 A1 | 1/2024 | Li et al. |
| 2024/0101548 A1 | 3/2024 | Wang et al. |
| 2024/0140929 A1 | 5/2024 | Dai et al. |
| 2024/0182429 A1 | 6/2024 | Wang |
| 2024/0382477 A1 | 11/2024 | Zhang et al. |

FOREIGN PATENT DOCUMENTS

| | | |
|---|---|---|
| CN | 104159891 | 11/2014 |
| CN | 111315737 | 6/2020 |
| CN | 111484480 | 8/2020 |
| CN | 111757878 | 10/2020 |
| CN | 113490664 | 10/2021 |
| CN | 113773262 | 12/2021 |
| CN | 115141149 | 10/2022 |
| WO | 2013054351 | 4/2013 |
| WO | 2014/074661 | 5/2014 |
| WO | 2018/111787 | 6/2018 |
| WO | 2018/118842 | 6/2018 |
| WO | 2019/079485 | 4/2019 |
| WO | 2019103952 | 5/2019 |
| WO | 2019/183186 | 9/2019 |
| WO | 2020/086616 | 4/2020 |
| WO | 2020/092196 | 5/2020 |
| WO | 2020/159904 | 8/2020 |
| WO | 2020156311 | 8/2020 |
| WO | 2021/222153 | 11/2021 |
| WO | 2022/117016 | 6/2022 |
| WO | WO 2022/135430 * | 6/2022 |
| WO | 2022/175745 | 8/2022 |
| WO | 2022/175747 | 8/2022 |
| WO | 2022/175752 | 8/2022 |
| WO | 2022/193499 | 9/2022 |
| WO | 2022/233286 | 11/2022 |
| WO | 2022/241171 | 11/2022 |
| WO | 2022/241172 | 11/2022 |
| WO | 2022/241173 | 11/2022 |
| WO | 2022/241174 | 11/2022 |
| WO | 2022/241175 | 11/2022 |

OTHER PUBLICATIONS

EP Search Report in related EP Application No. 21909426.5-1102 dated Dec. 11, 2024, 9 pages.
International Search Report in related PCT Application No. PCT/CN2021/140271 dated Mar. 22, 2022, 6 pages.
Utility U.S. Appl. No. 18/268,681, filed Jun. 21, 2023, 170 pages.
Non-final Office Action in U.S. Appl. No. 18/268,681 dated Aug. 20, 2025, 8 pages.
Response to Non-final Office Action in U.S. Appl. No. 18/268,681 dated Sep. 18, 2025, 6 pages.
U.S. Appl. No. 19/382,830, filed Nov. 7, 2025, 170 pages.

* cited by examiner

*Primary Examiner* — Brian E McDowell
(74) *Attorney, Agent, or Firm* — NIXON & VANDERHYE, PC

(57) ABSTRACT

Provided herein are compounds, crystalline free forms, crystalline salt forms, and pharmaceutical compositions of Compound 1. Also provided are methods of preparing and methods of using the same, e.g., for inhibiting a kinase and/or for treating various diseases or disorders, such as autoimmune diseases.

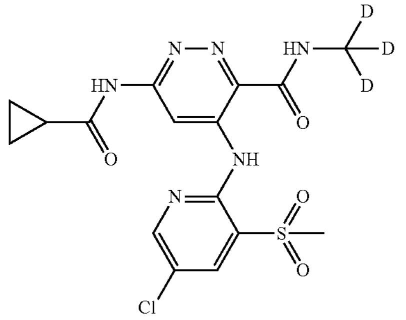

12 Claims, 64 Drawing Sheets

Figure 16A:
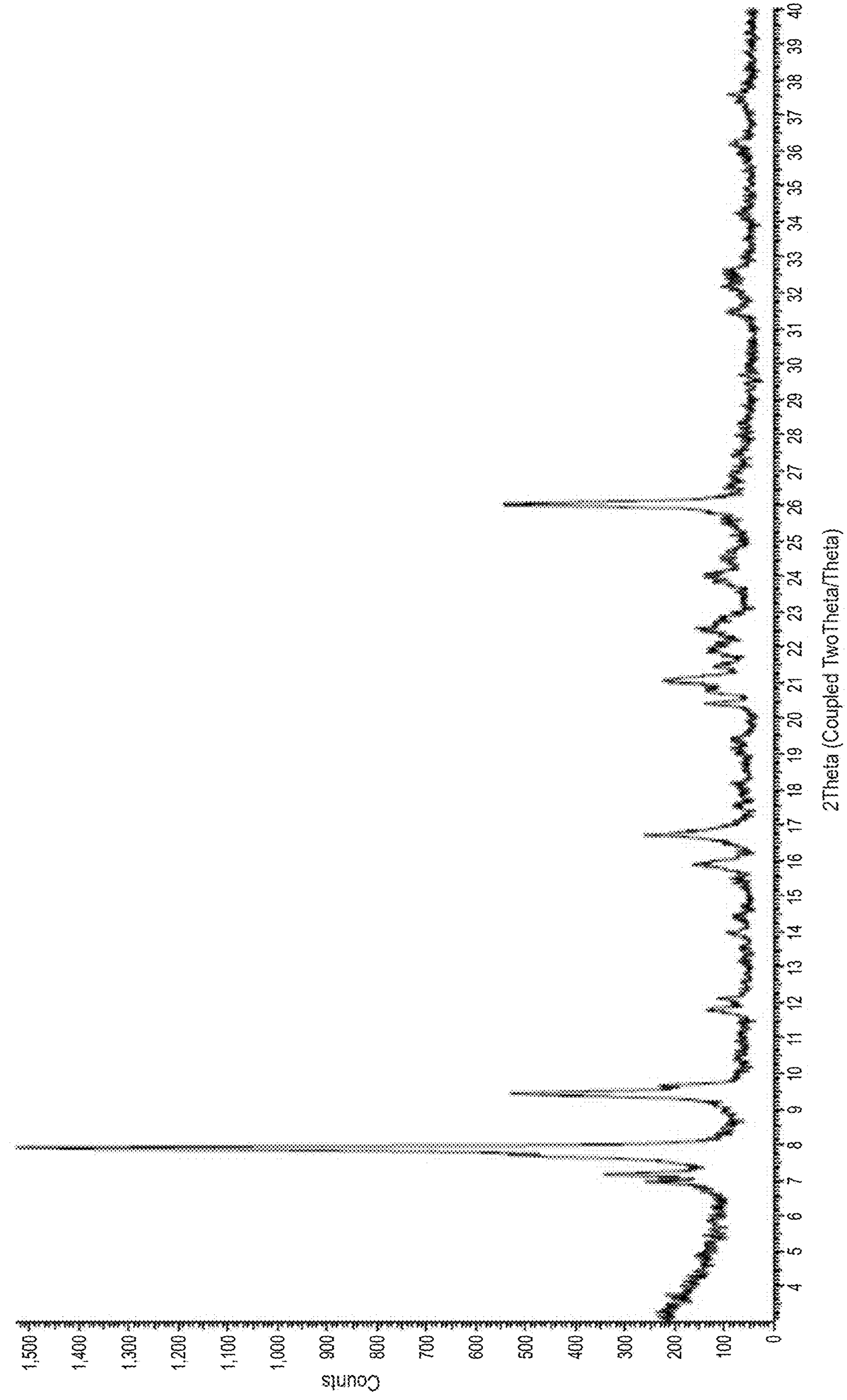
Figure 16B:
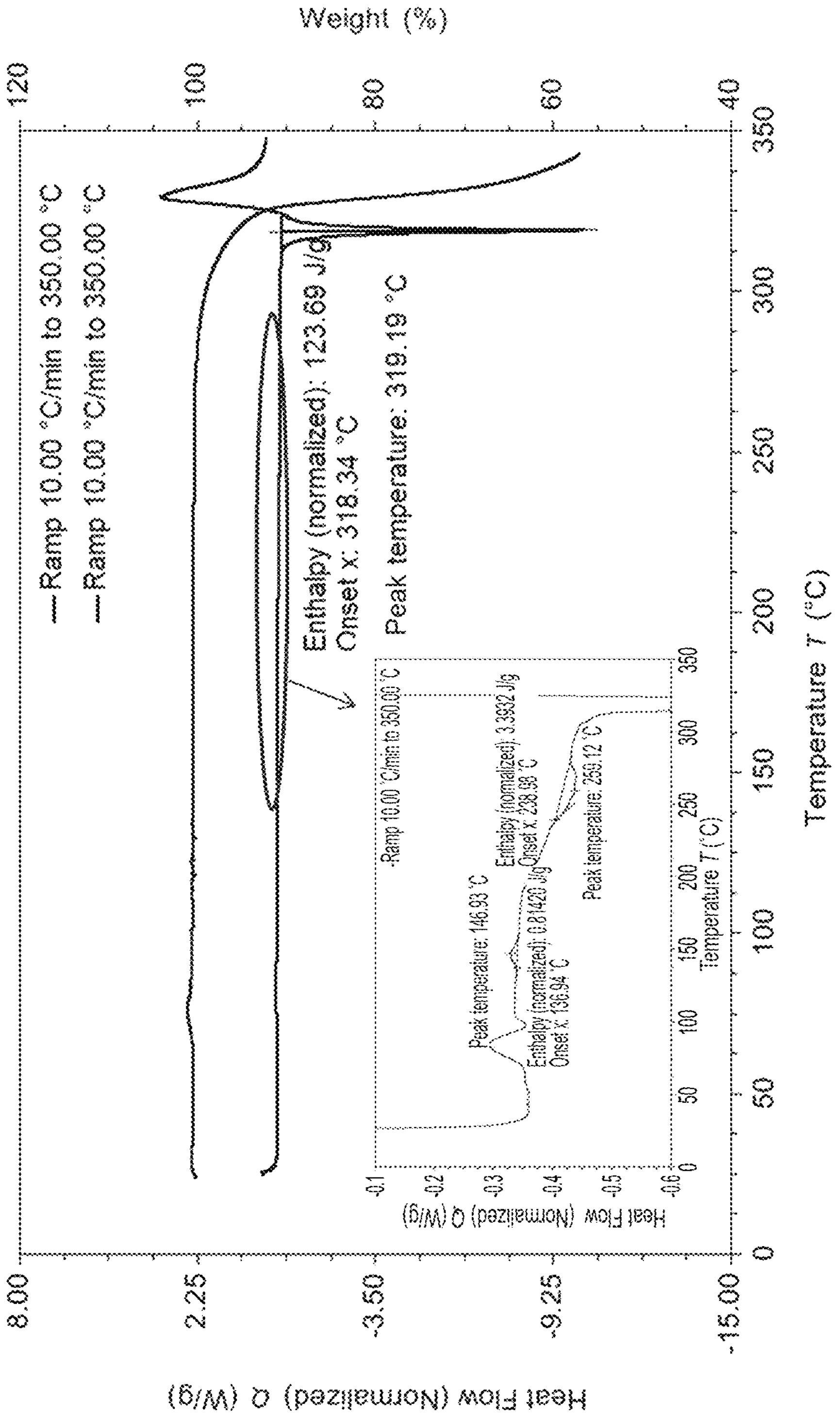

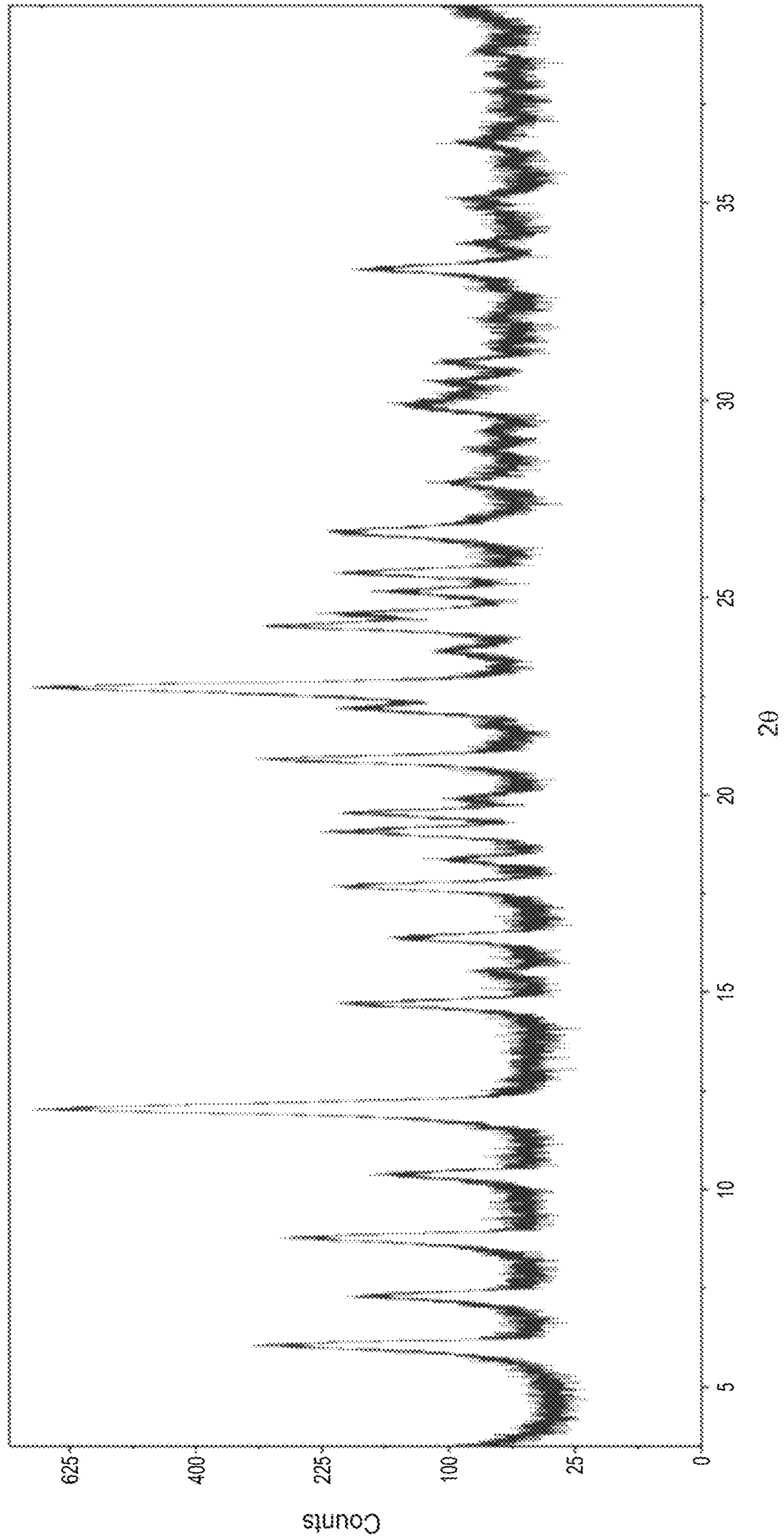
FIG. 16B-a

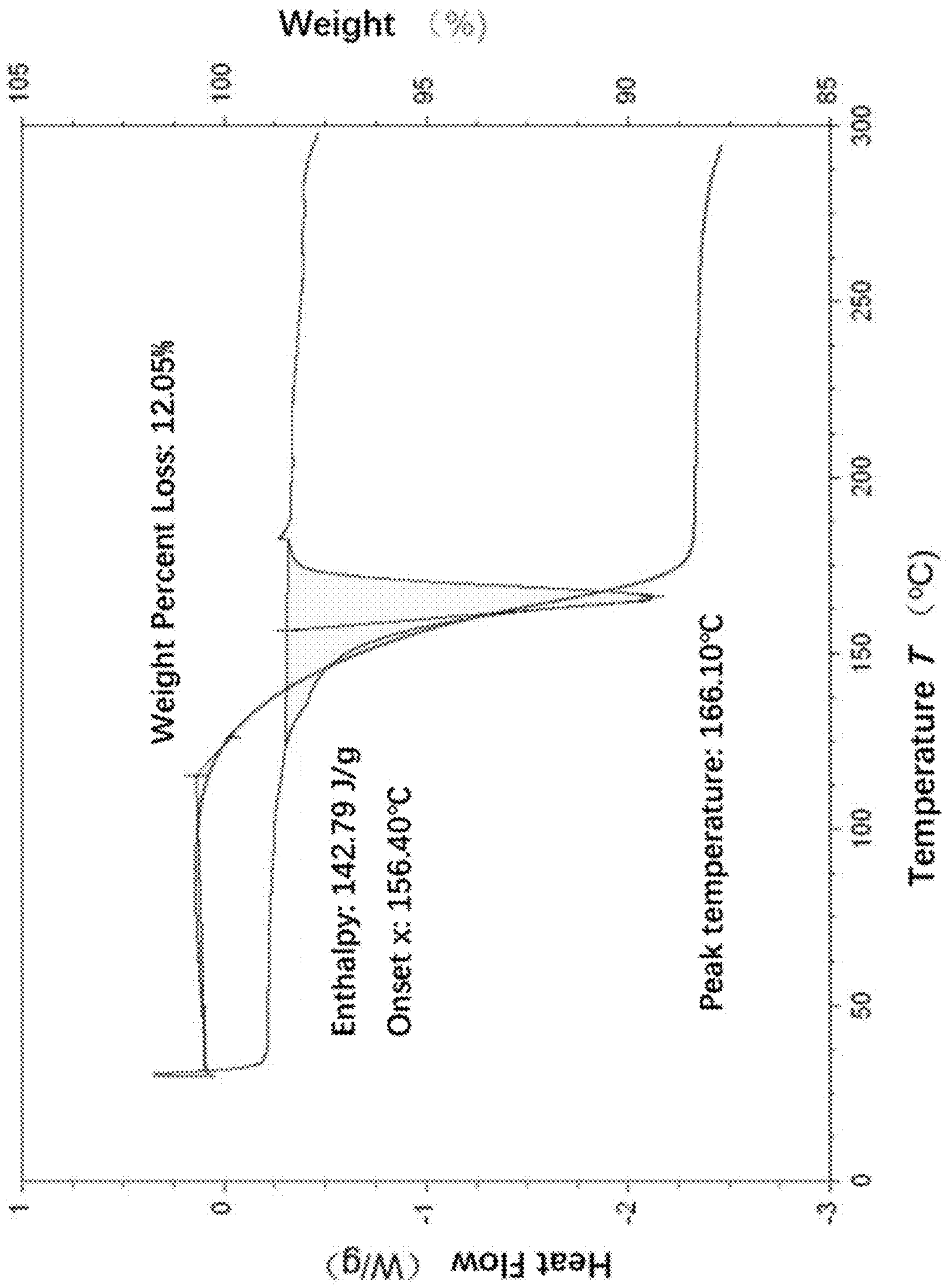
FIG. 16B-b

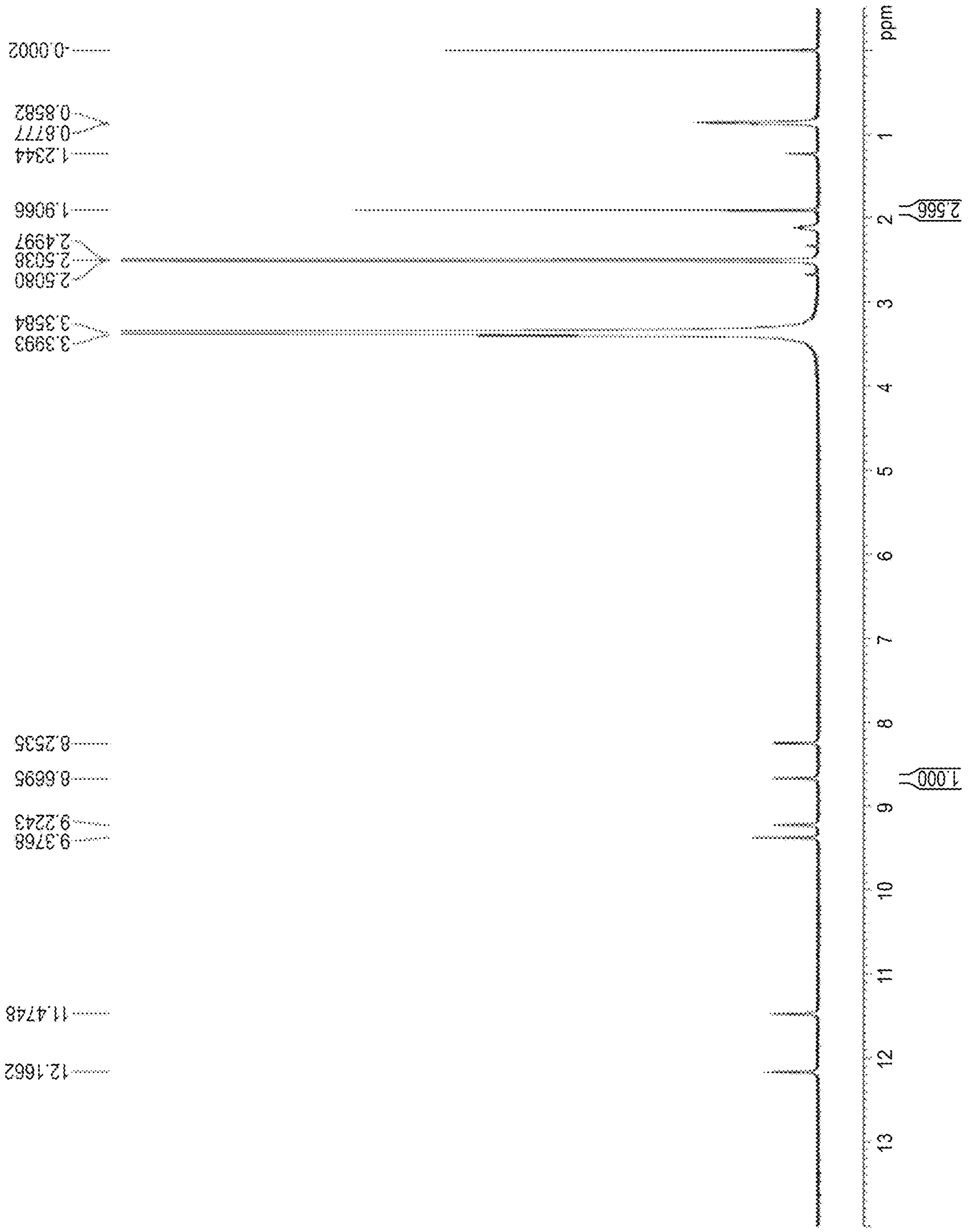
FIG. 16B-c

HETEROARYL COMPOUNDS, SOLID FORMS, PREPARATION METHODS AND USES THEREOF

CROSS REFERENCE TO RELATED APPLICATIONS

This application is a continuation of U.S. application Ser. No. 18/211,741, filed on Jun. 20, 2023, which claims priority of Chinese Application No. CN202210700943.X, filed on Jun. 20, 2022, the content of each of which is incorporated herein by reference in its entirety.

BACKGROUND

In various embodiments, the present disclosure generally relates to novel crystalline Forms of heteroaryl compounds, compositions comprising the same, methods of preparing and methods of using the same, e.g., for inhibiting a kinase and/or for treating various diseases or disorders, such as autoimmune diseases described herein.

BACKGROUND

The Janus kinase (JAK) family is a small family of receptor-associated tyrosine kinases that are essential for the signal cascade downstream of type I and type II cytokine receptors, Type I and type II cytokine receptors—which compose a family of receptors bound by over 50 cytokines, interleukins, interferons (IFNs), colony-stimulating factors (CSFs) and hormones—share a distinct intracellular signaling pathway mediated by JAKs that bind directly to the intracellular domains of type I and type II cytokine receptors and not to other classes of cytokine receptor. JAK-dependent cytokines are major contributors to immunopathology. The dependence of type I and type II cytokines on JAKs was established in a variety of genetic models from mutagenized cell lines and knockout mice to humans. Polymorphisms in JAK and signal transducer and activator of transcription (STAT) genes are associated with autoimmunity, and loss of function mutations cause immunodeficiency due to the inability of type I and type II cytokines to transmit signals through their receptors. The critical role of JAKs in type I and type II cytokine signaling strongly argues that interfering with the activity of these kinases could lead to a new class of immunomodulatory drugs.

A new compound and its novel crystalline forms and salts that modulate cytokines and/or interferons, such as IL-12, IL-23 and/or IFNα, should deliver a pharmacological response that favorably treats one or more of the conditions described herein and may provide substantial therapeutic benefits to a wide variety of patients in need thereof.

BRIEF SUMMARY

International Application No. PCT/CN2021/140271, filed on Dec. 22, 2021, the content of which is incorporated herein by reference in its entirety, describes Compound 1, which can modulate the function of IL-12, IL-23 and/or IFNα.

Compound 1

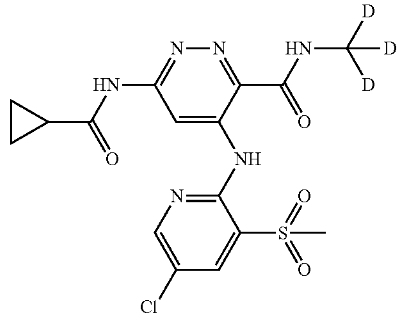

In various embodiments, the present disclosure is directed to Compound 1 or a pharmaceutically acceptable salt thereof or a hydrate or a solvate of the same, which can be for example, in an isolated form, a substantially pure form, and/or in a solid form. Further provided are pharmaceutical compositions comprising the Compound 1 or a pharmaceutically acceptable salt thereof or a hydrate or a solvate thereof, methods of preparing the same, and methods of using the same.

Certain embodiments of the present disclosure are directed to Compound 1, which can be for example, in a substantially pure form and/or in a solid form. In some embodiments, the Compound 1 can be in an amorphous form. In some embodiments, the Compound 1 can be in a crystalline form, such as crystalline Form I, II, III, IV, V, VI, VII, VIII, IX, X, XI, XII, XIII, XIV, XV, XVI, or XVII, or salt Form A, B, C, D, E, F, G, H, J, K, or L as described herein. In some embodiments, Compound 1 can be substantially pure.

Compounds of the present disclosure can be used for preparing a pharmaceutical composition. In some embodiments, the pharmaceutical composition can comprise one or more of the compounds of the present disclosure (e.g., Compound 1 in crystalline Forms I, II, III, IV, V, VI, VII, VIII, IX, X, XI, XII, XIII, XIV, XV, XVI, and XVII, or in salt Forms A, B, C, D, E, F, G, H, J, K, and L, or in any combination thereof).

The pharmaceutical compositions described herein can be formulated for any suitable routes of administration. In some embodiments, the pharmaceutical composition can be formulated for oral administration. For example, in some embodiments, the pharmaceutical composition can be a tablet or a capsule.

In some embodiments, the present disclosure provides a method of inhibiting the function of IL-23, IL-12 and/or IFN-alpha in a subject in need thereof, the method comprising administering to the subject a therapeutically effective amount of a compound of the present disclosure (e.g., Compound 1 in crystalline Form I, II, III, IV, V, VI, VII, VIII, IX, X, XI, XII, XIII, XIV, XV, XVI, or XVII, or in salt Form A, B, C, D, E, F, G, H, J, K, or L), or pharmaceutical composition described herein. Exemplary diseases or disorders that can be treated with the methods herein also include but not limited to those proliferative, metabolic, allergic, autoimmune and/or inflammatory diseases or disorders described herein.

Compounds of the present disclosure can be used as a monotherapy or in a combination therapy. In some embodiments, the methods of treating IL-23-, IL-12 and/or IFNα-associated diseases or disorders can comprise administering compounds of the present disclosure alone or in combination with each other and/or other suitable therapeutic agents useful in treating such conditions. Exemplary of such other suitable therapeutic agents include corticosteroids, rolipram, calphostin, cytokine-suppressive anti-inflammatory drugs (CSAIDs), interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The administering herein is not limited to any particular route of administration. For example, in some embodiments, the administering can be orally, nasally, transdermally, pulmonary, inhalationally, buccally, sublingually, intraperitoneally, subcutaneously, intramuscularly, intravenously, rectally, intrapleurally, intrathecally and parenterally. In some embodiments, the administering is orally.

Dosing regimen including doses can vary and can be adjusted, which can depend on the recipient of the treatment, the disease or disorder being treated and the severity thereof, the composition containing the compound, the time of administration, the route of administration, the duration of treatment, the compound potency, its rate of clearance and whether or not another drug is co-administered.

It is to be understood that both the foregoing summary and the following detailed description are exemplary and explanatory only, and are not restrictive of the invention herein.

BRIEF DESCRIPTION OF THE DRAWINGS/FIGURES

Figure 1A:
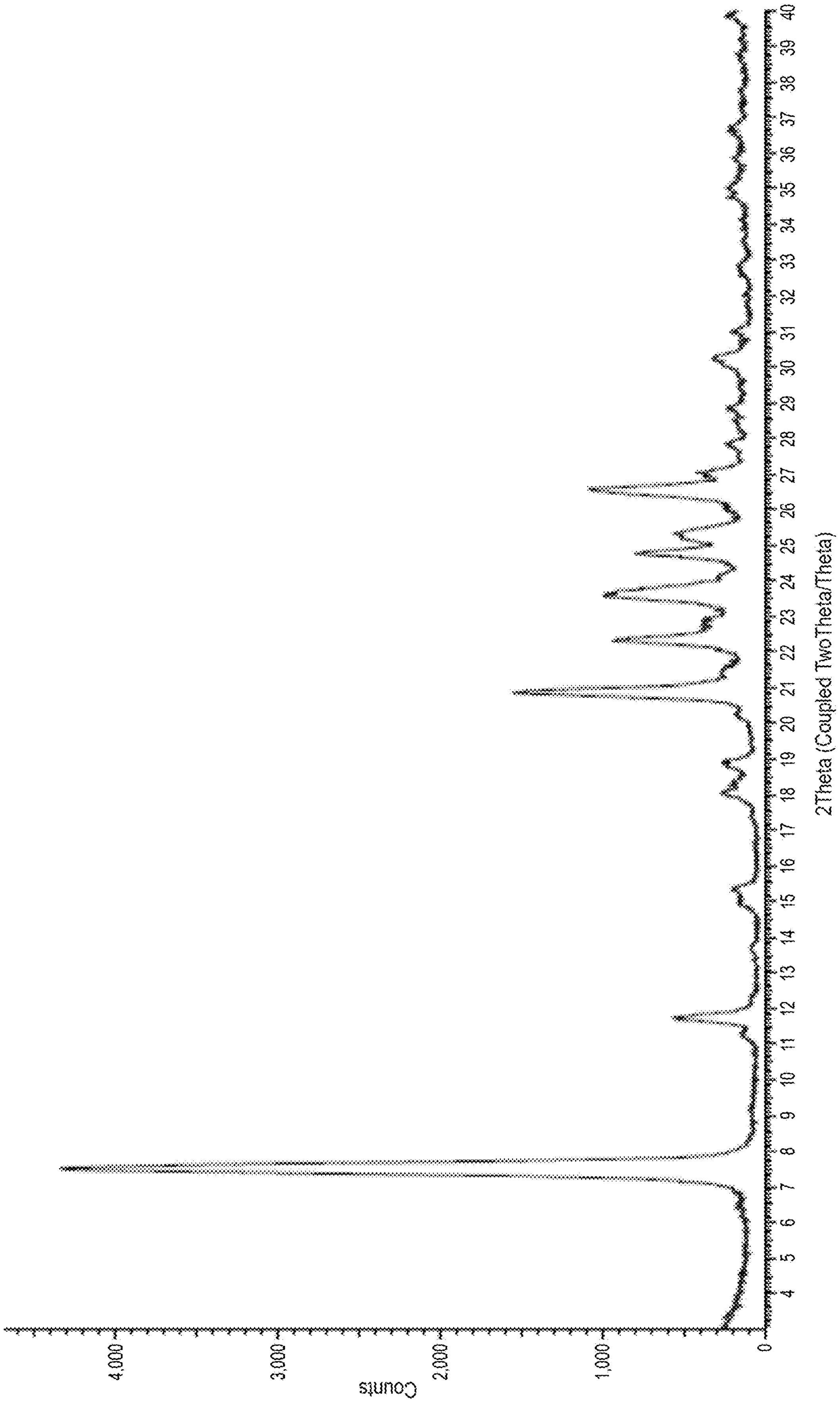
Figure 1B:
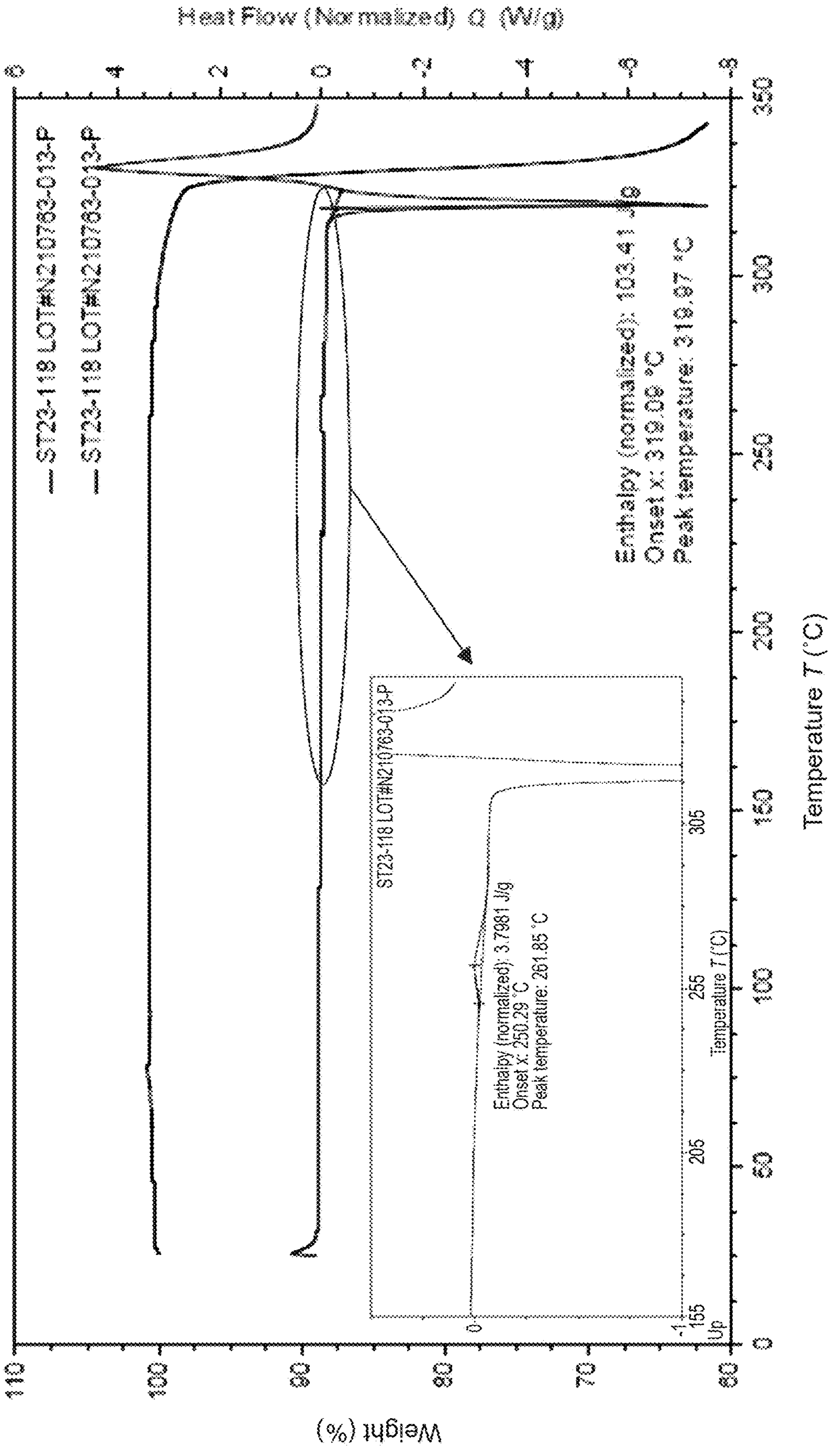

FIG. 1*a* shows a representative X-ray powder diffraction (XRPD) spectrum of crystalline Form I of Compound 1. FIG. 1*b* shows a representative thermogravimetric analysis (TGA) and differential scanning calorimetry (DSC) analysis of crystalline Form I of Compound 1.

Figure 2A:
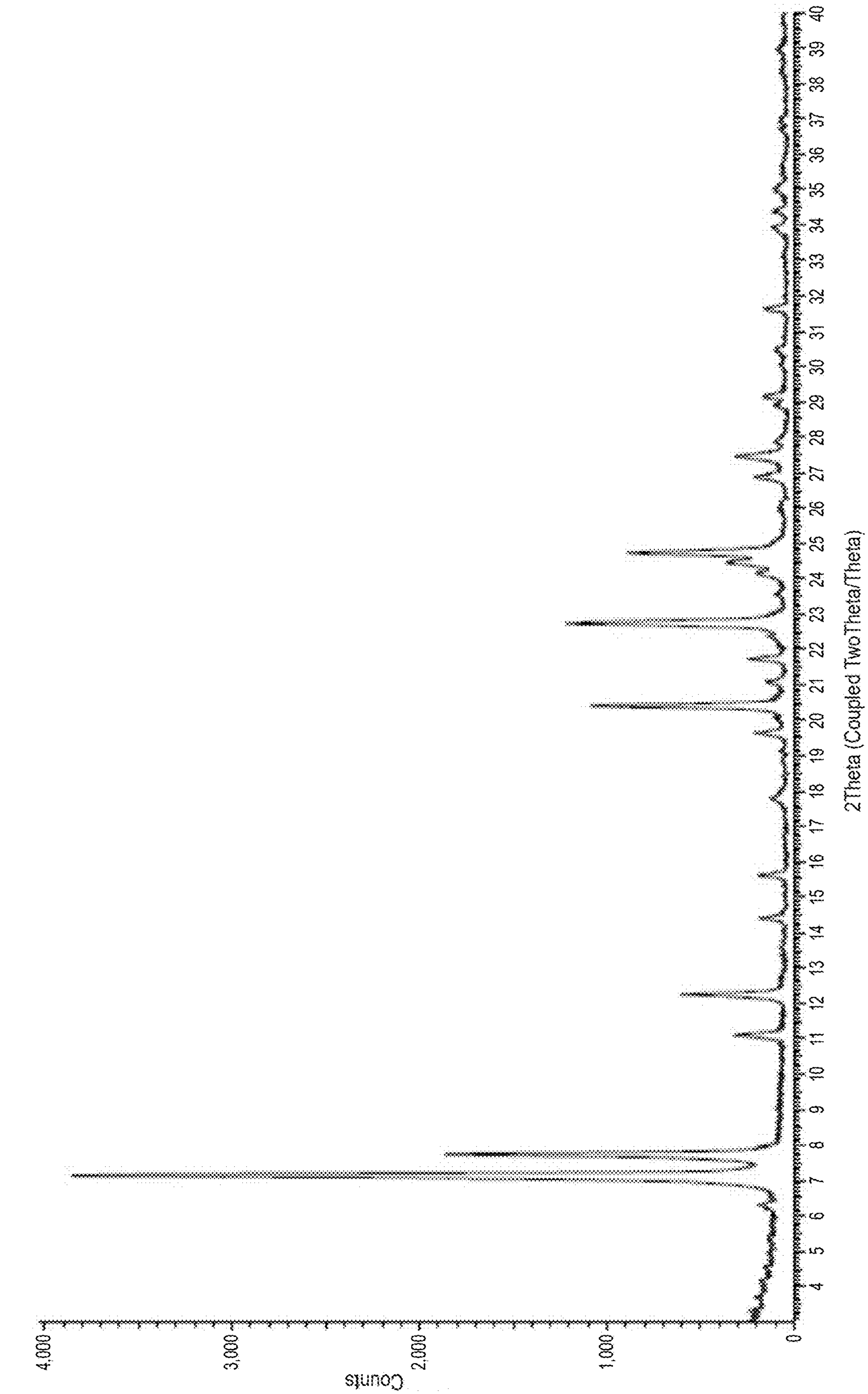
Figure 2B:
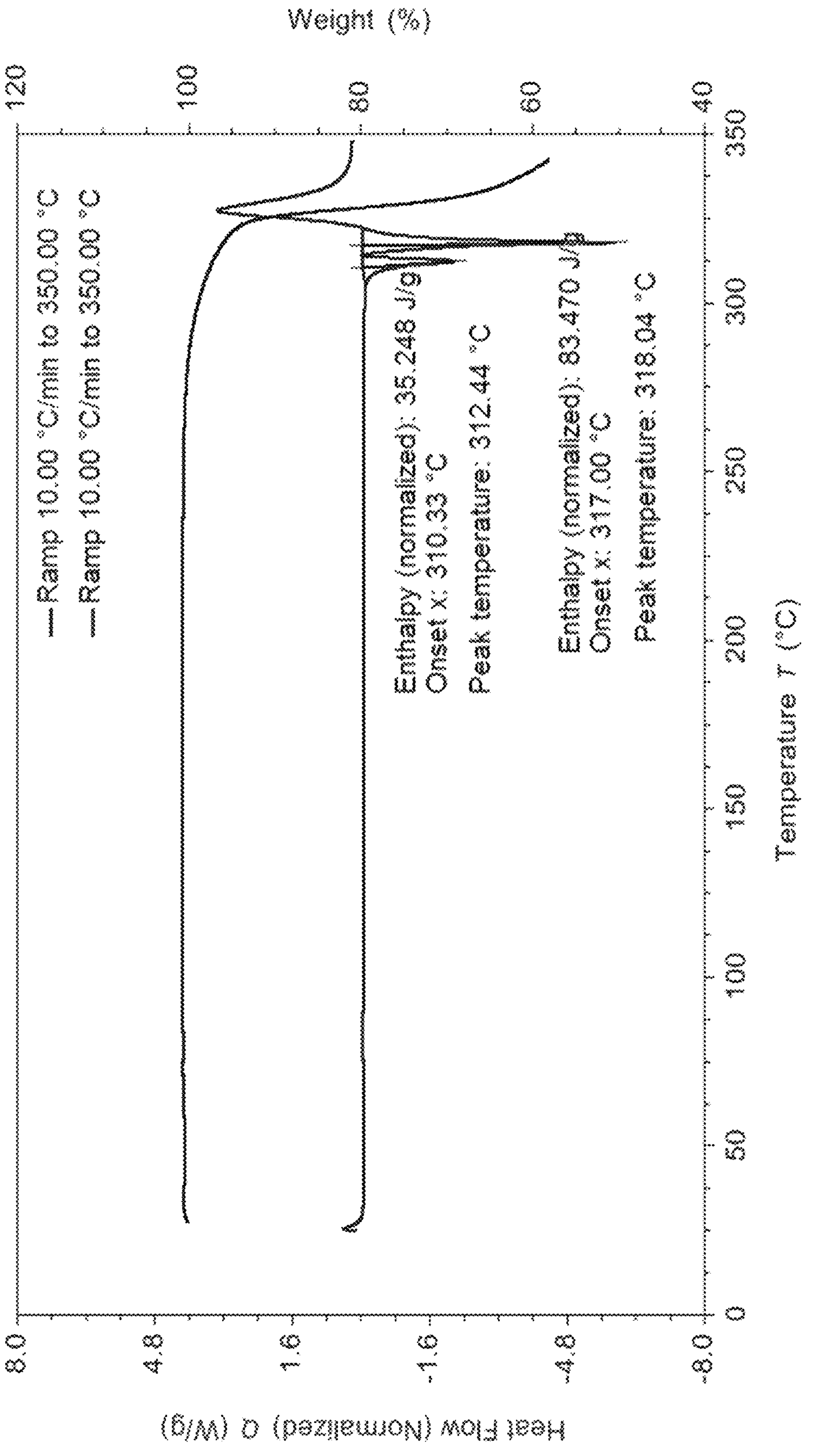

FIG. 2*a* shows a representative X-ray powder diffraction (XRPD) spectrum of crystalline Form II of Compound 1. FIG. 2*b* shows a representative thermogravimetric analysis (TGA) and differential scanning calorimetry (DSC) analysis of crystalline Form II of Compound 1.

Figure 3A:
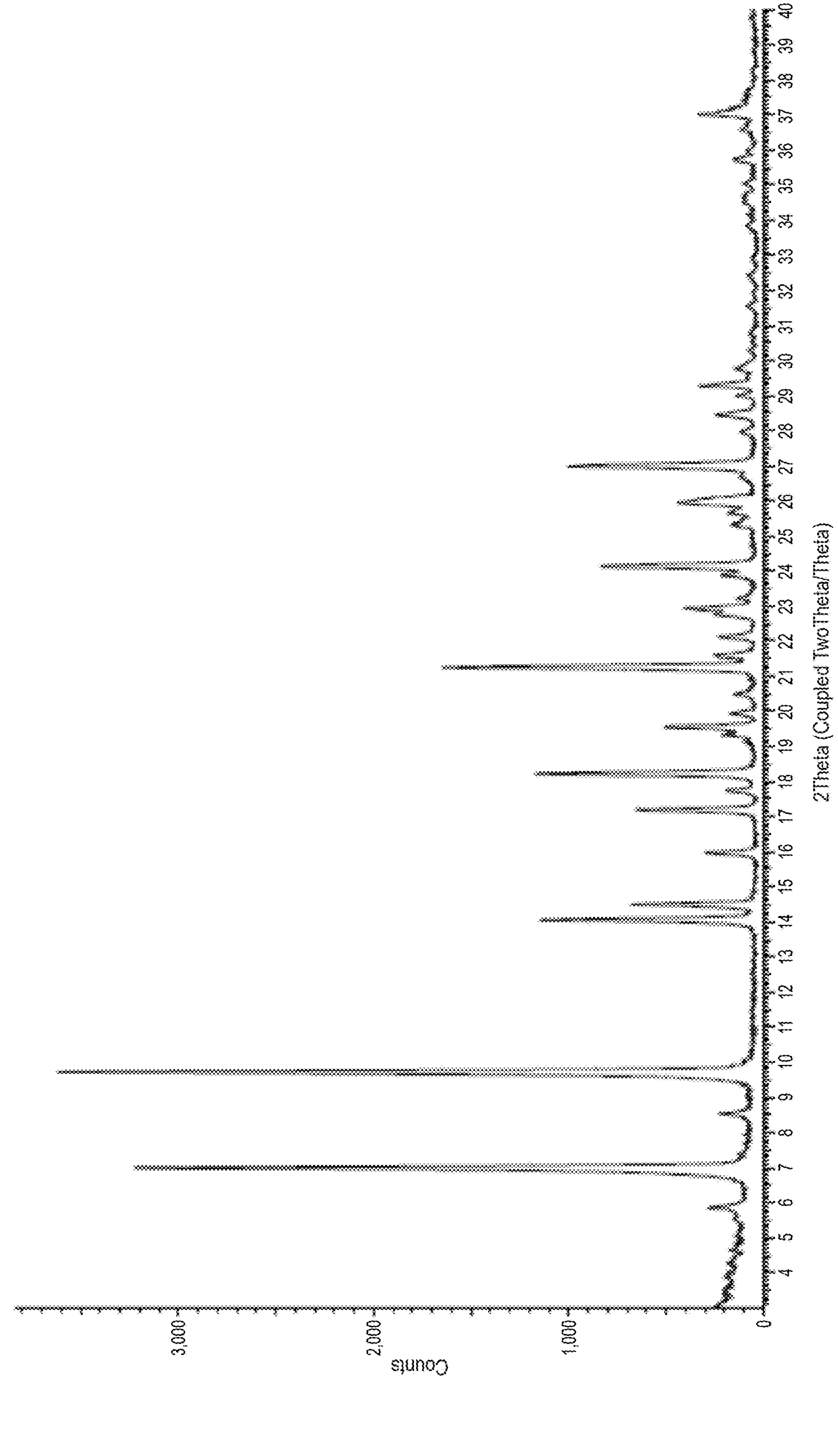
Figure 3B:
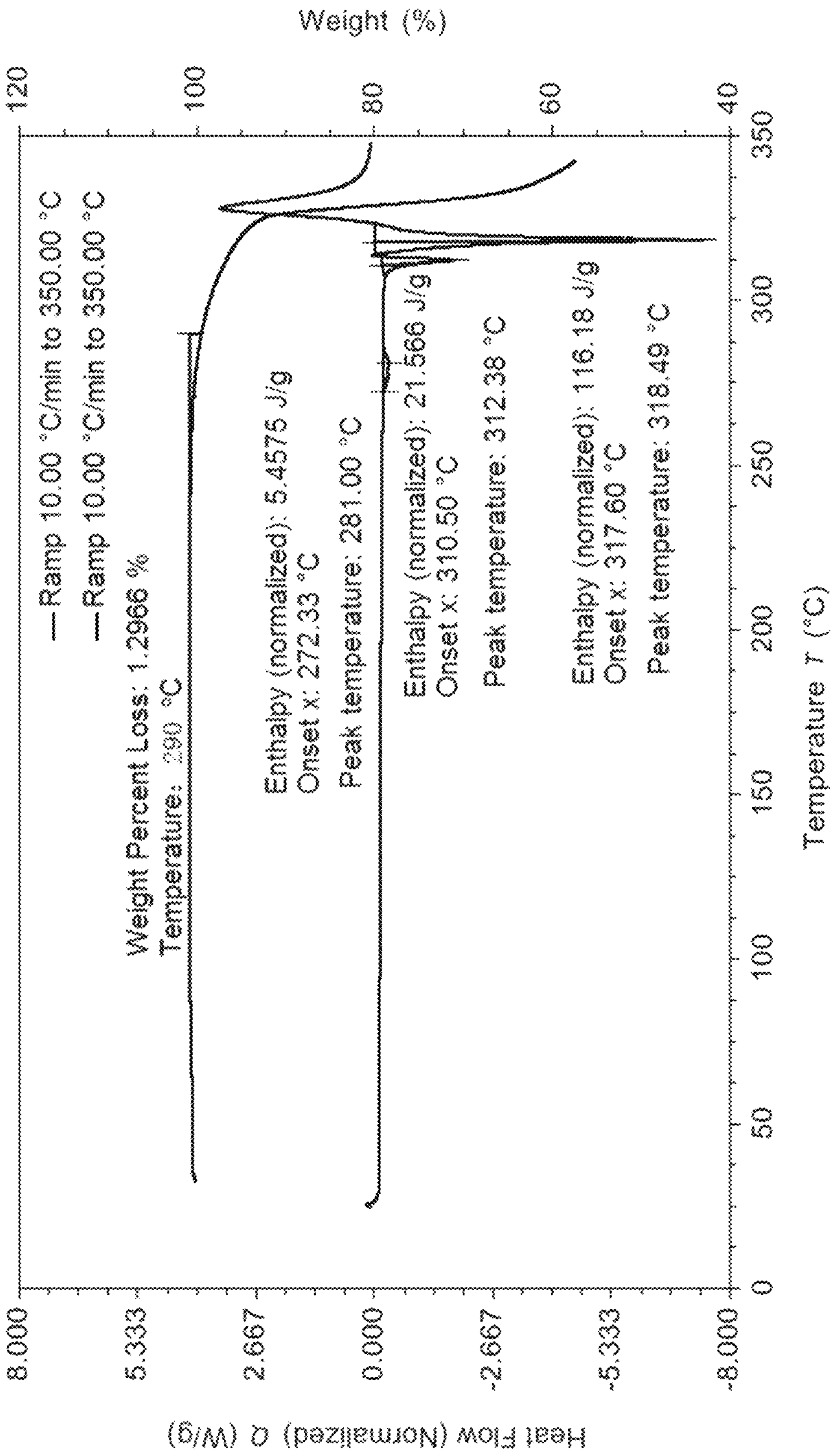
Figure 3C:
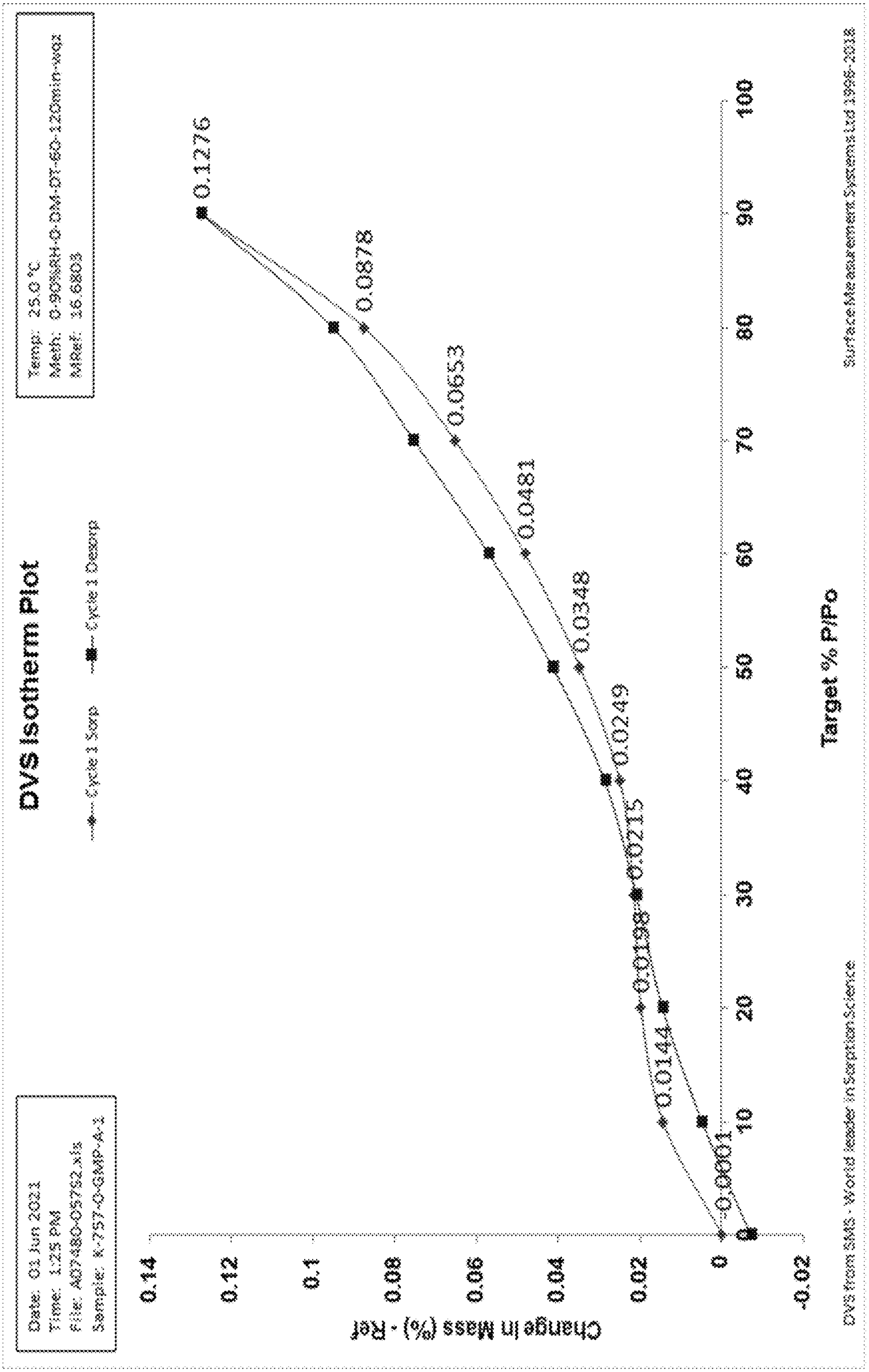

FIG. 3*a* shows a representative X-ray powder diffraction (XRPD) spectrum of crystalline Form III of Compound 1. FIG. 3*b* shows a representative thermogravimetric analysis (TGA) and differential scanning calorimetry (DSC) analysis of crystalline Form III of Compound 1. FIG. 3*c* presents a representative dynamic vapor sorption (DVS) analysis of Form III of Compound 1.

Figure 4A:
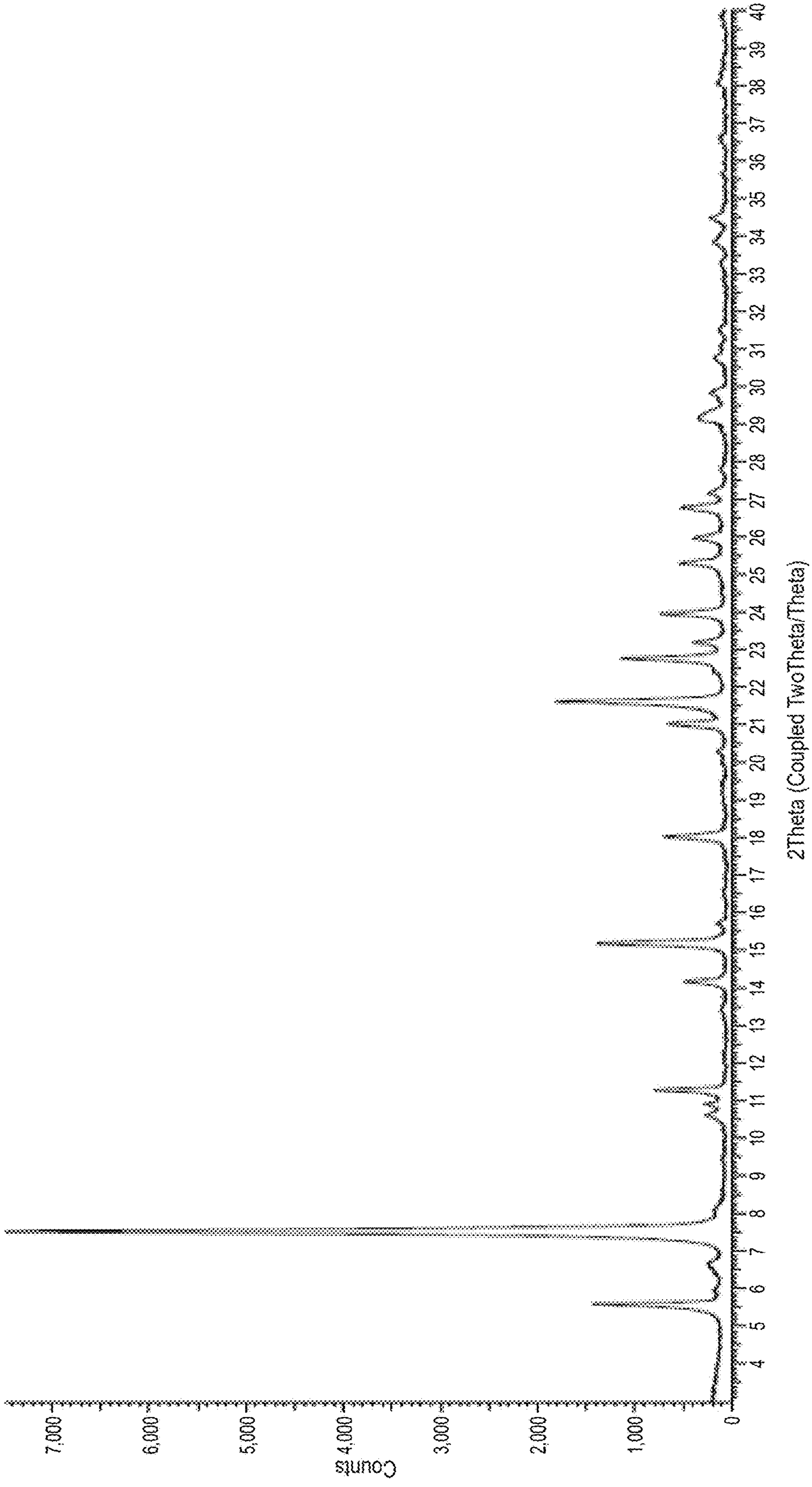
Figure 4B:
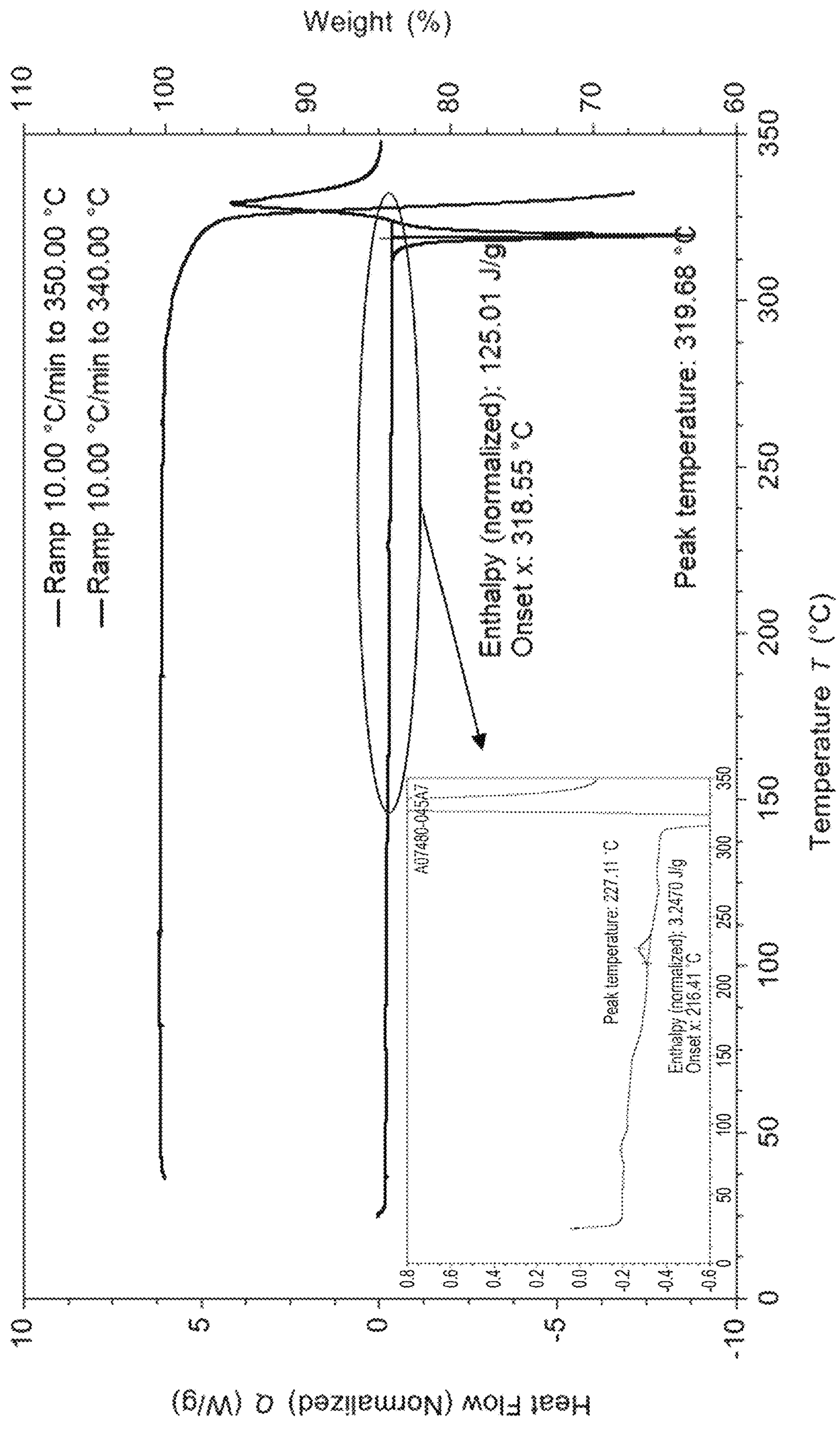

FIG. 4*a* shows a representative X-ray powder diffraction (XRPD) spectrum of crystalline Form IV of Compound 1. FIG. 4*b* shows a representative thermogravimetric analysis (TGA) and differential scanning calorimetry (DSC) analysis of crystalline Form IV of Compound 1.

Figure 5A:
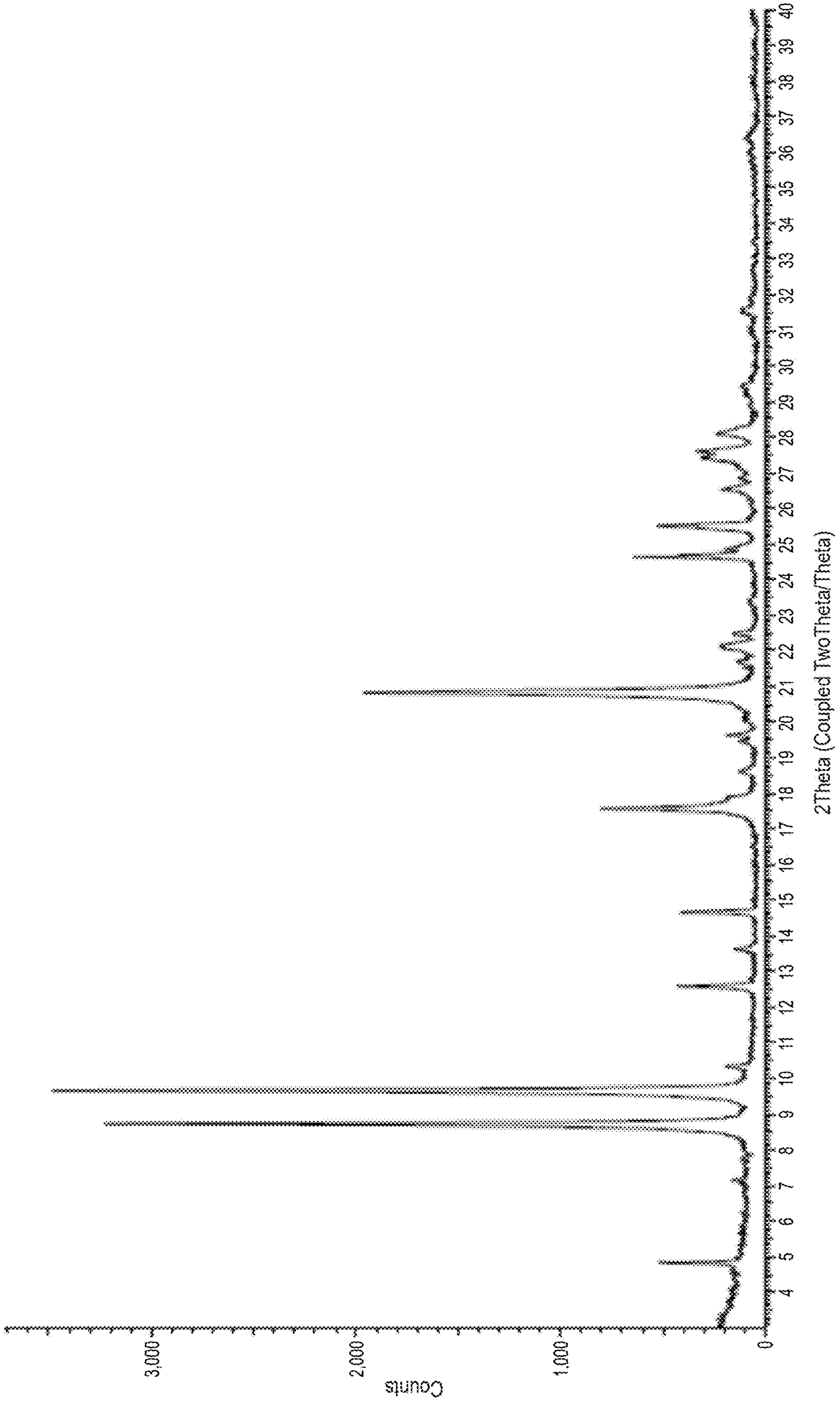
Figure 5B:
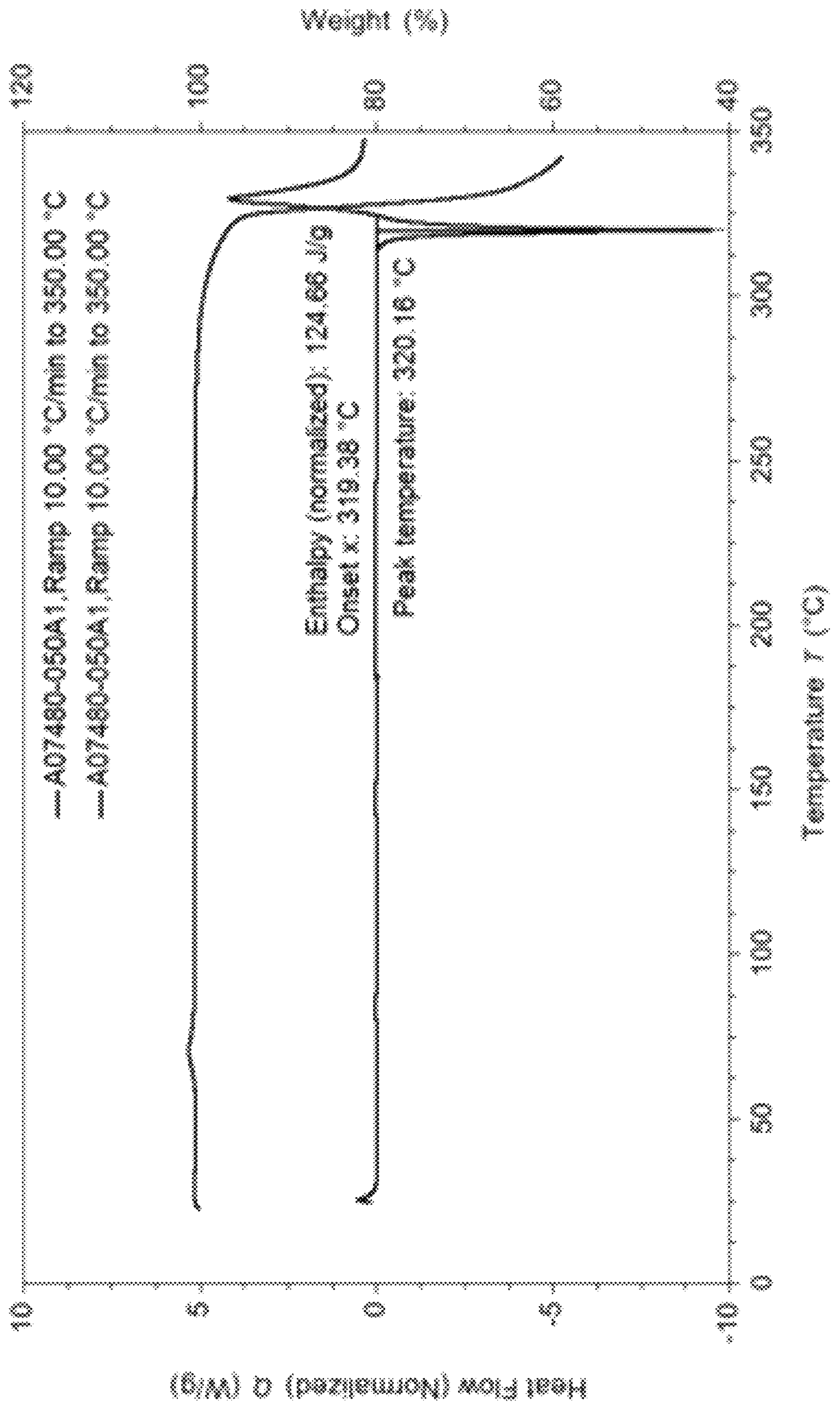

FIG. 5*a* shows a representative X-ray powder diffraction (XRPD) spectrum of crystalline Form V of Compound 1. FIG. 5*b* shows a representative thermogravimetric analysis (TGA) and differential scanning calorimetry (DSC) analysis of crystalline Form V of Compound 1.

Figure 6A:
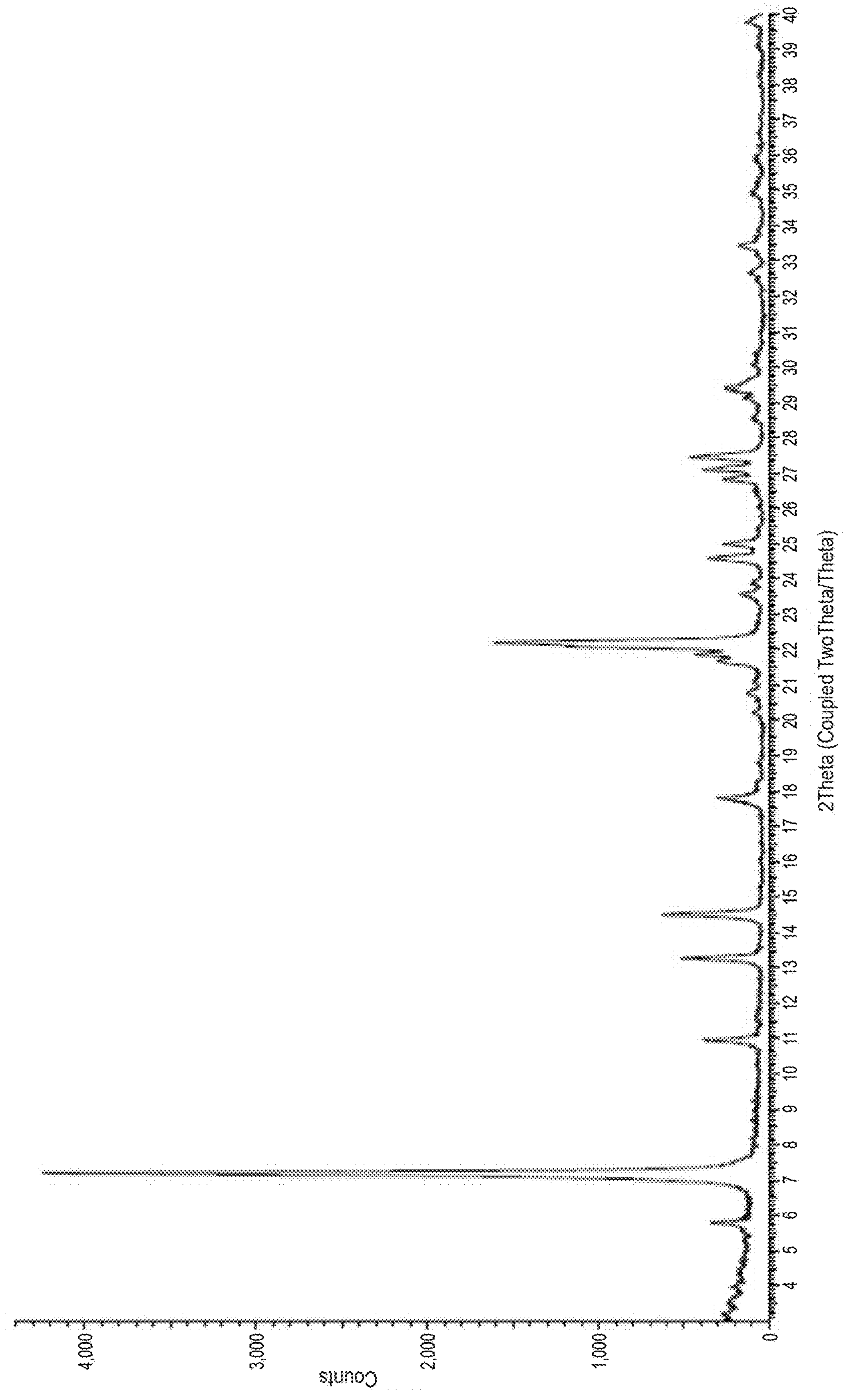
Figure 6B:
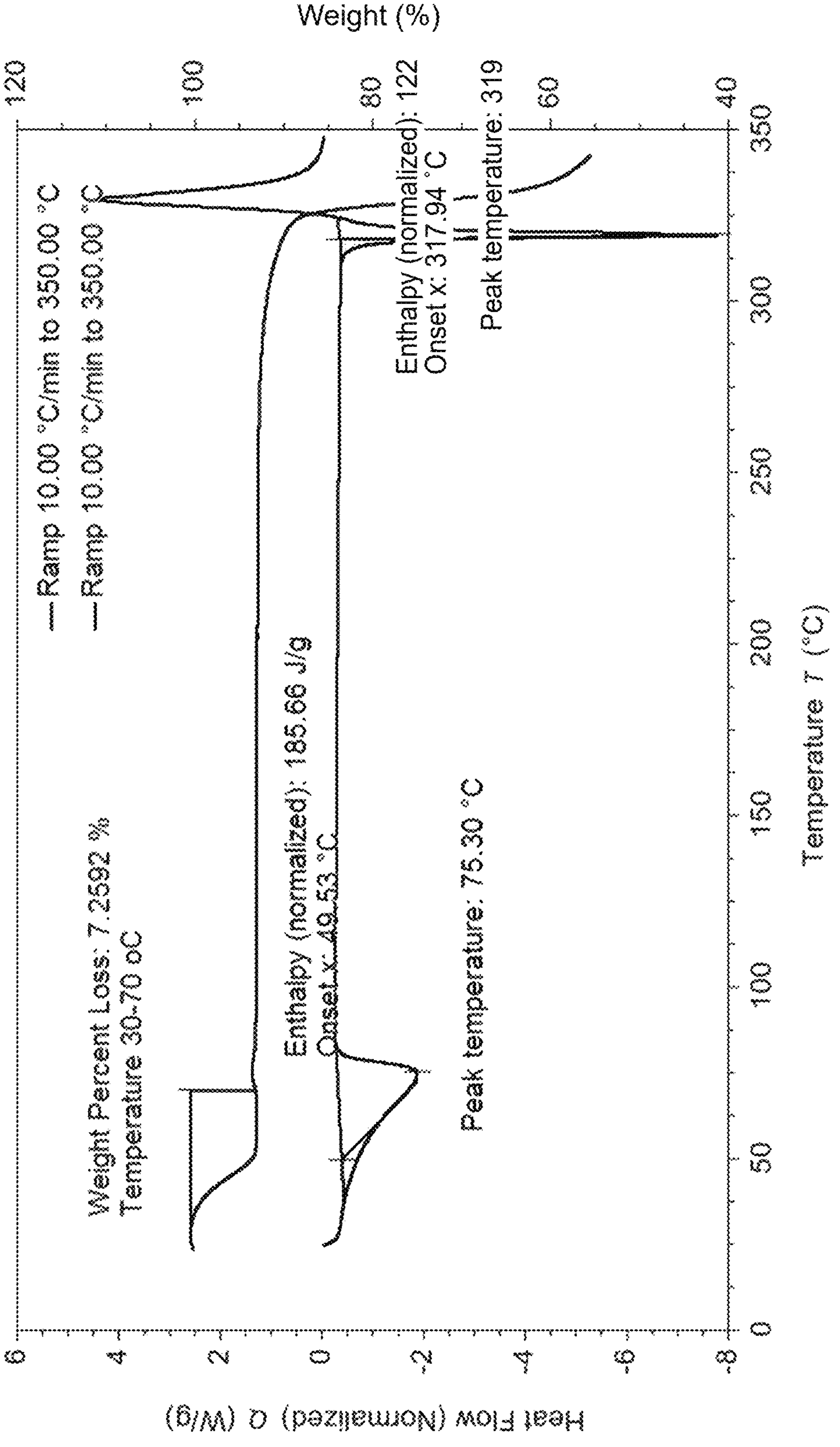

FIG. 6*a* shows a representative X-ray powder diffraction (XRPD) spectrum of crystalline Form VI of Compound 1. FIG. 6*b* shows a representative thermogravimetric analysis (TGA) and differential scanning calorimetry (DSC) analysis of crystalline Form VI of Compound 1.

Figure 7A:
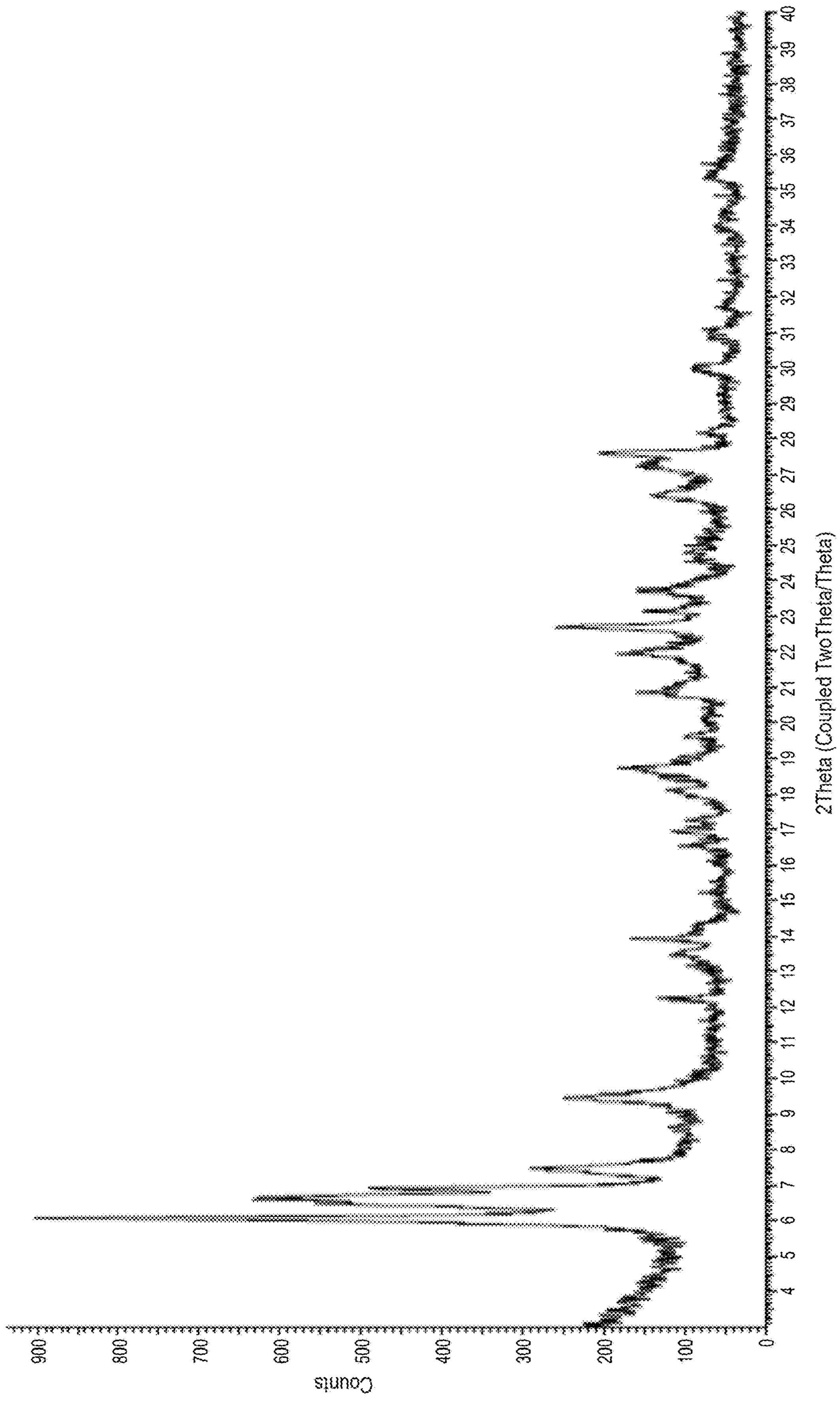
Figure 7B:
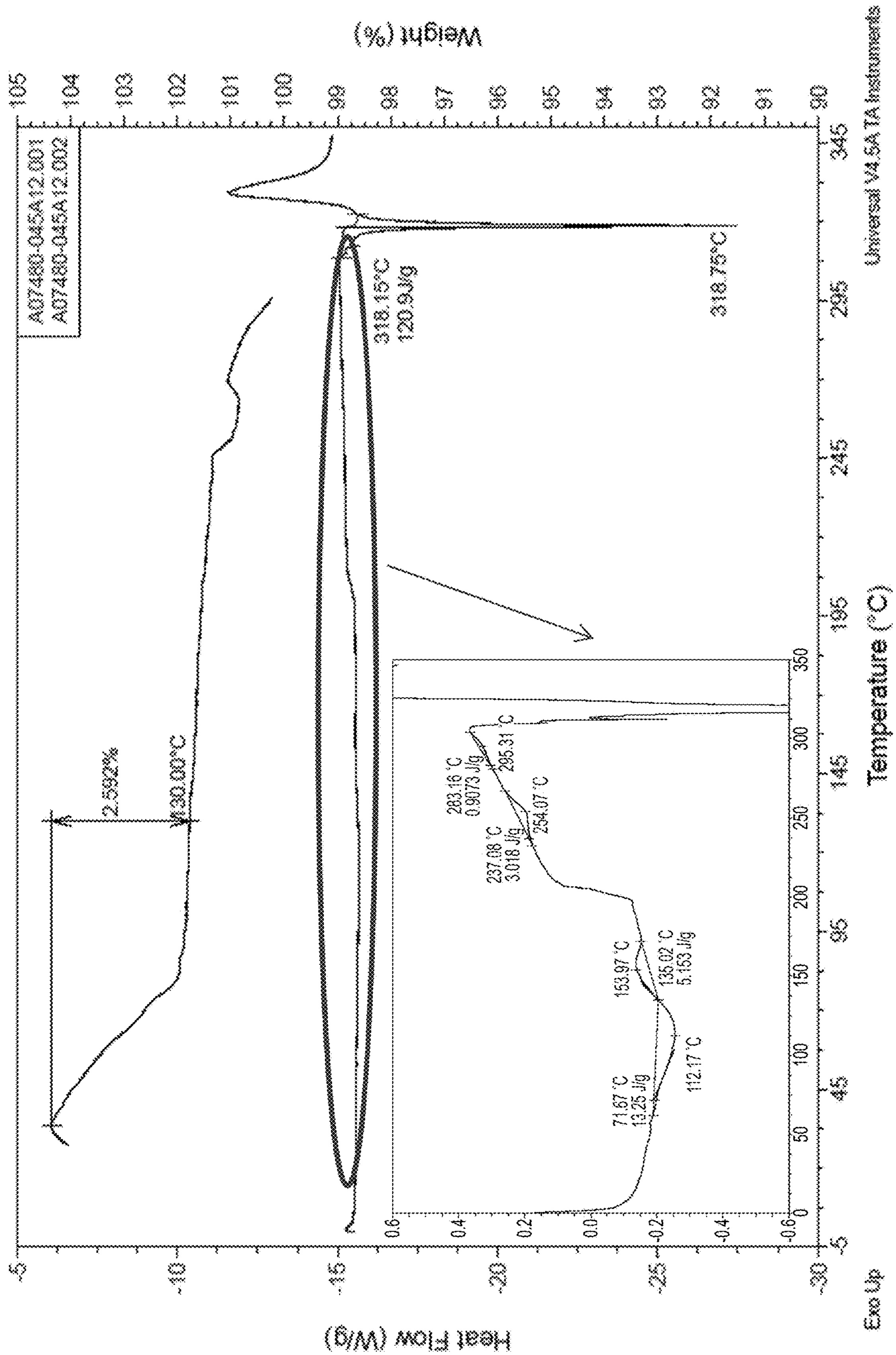

FIG. 7*a* shows a representative X-ray powder diffraction (XRPD) spectrum of crystalline Form VII of Compound 1. FIG. 7*b* shows a representative thermogravimetric analysis (TGA) and differential scanning calorimetry (DSC) analysis of crystalline Form VII of Compound 1.

Figure 8A:
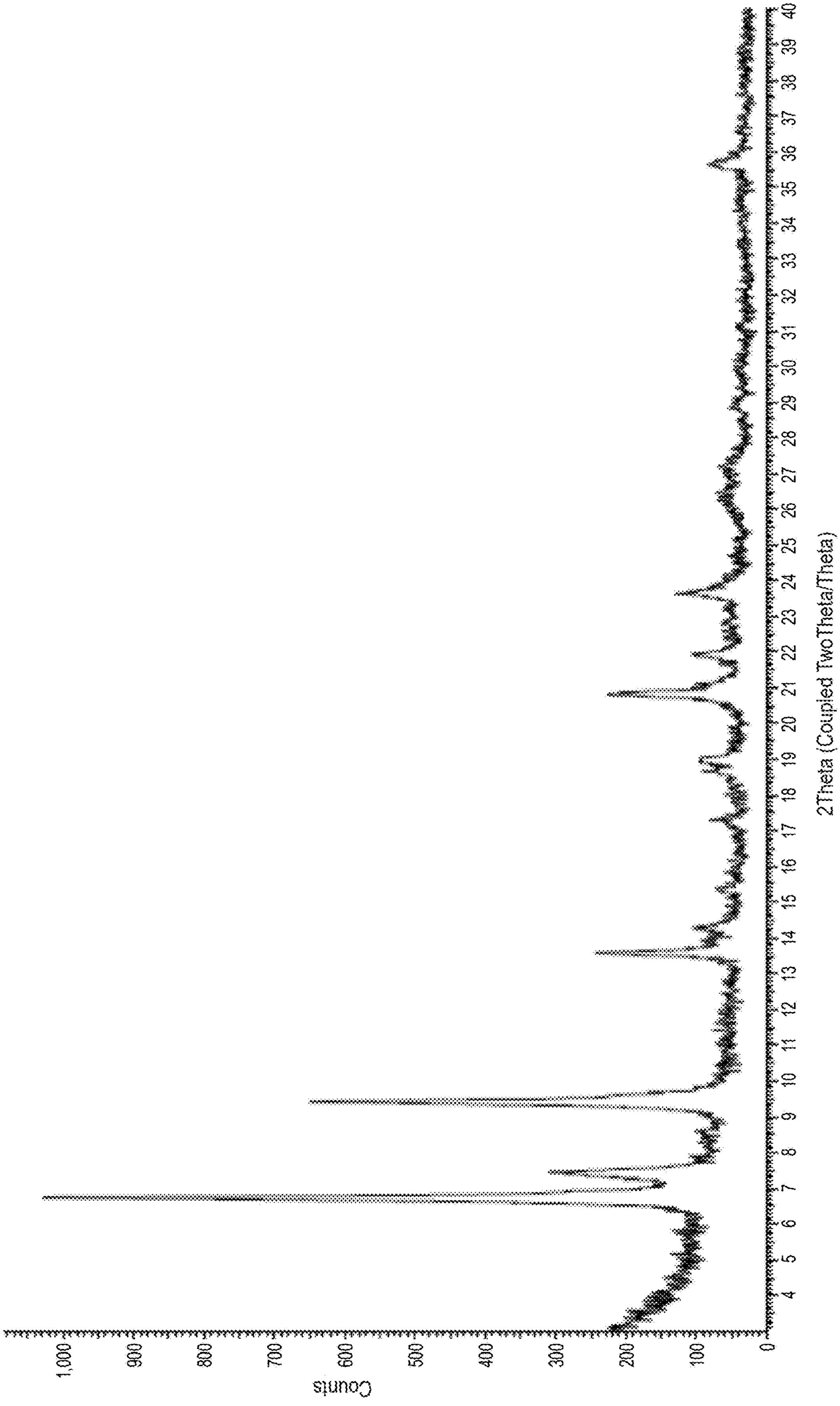
Figure 8B:
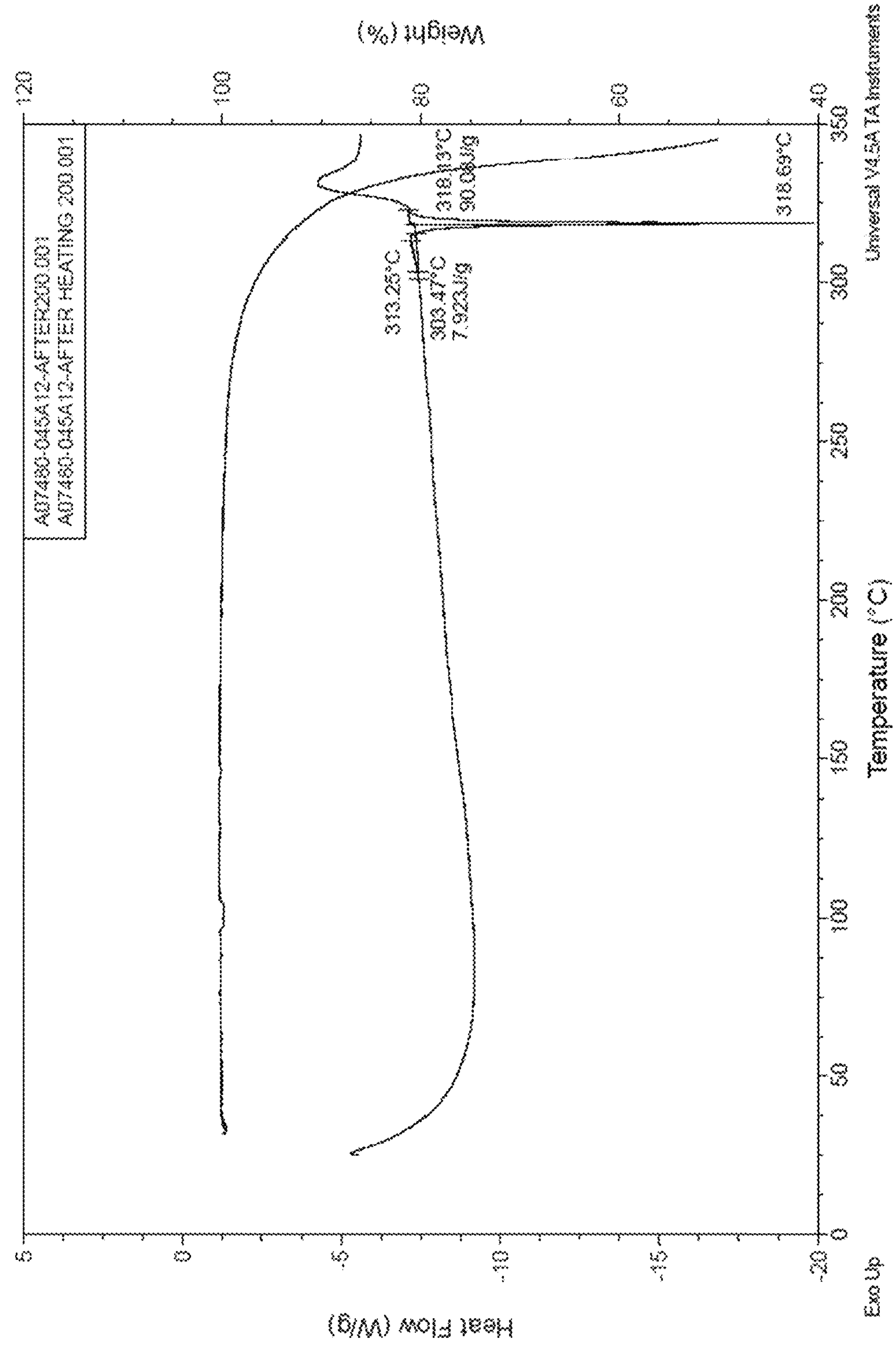

FIG. 8*a* shows a representative X-ray powder diffraction (XRPD) spectrum of crystalline Form VIII of Compound 1. FIG. 8*b* shows a representative thermogravimetric analysis (TGA) and differential scanning calorimetry (DSC) analysis of crystalline Form VIII of Compound 1.

Figure 9A:
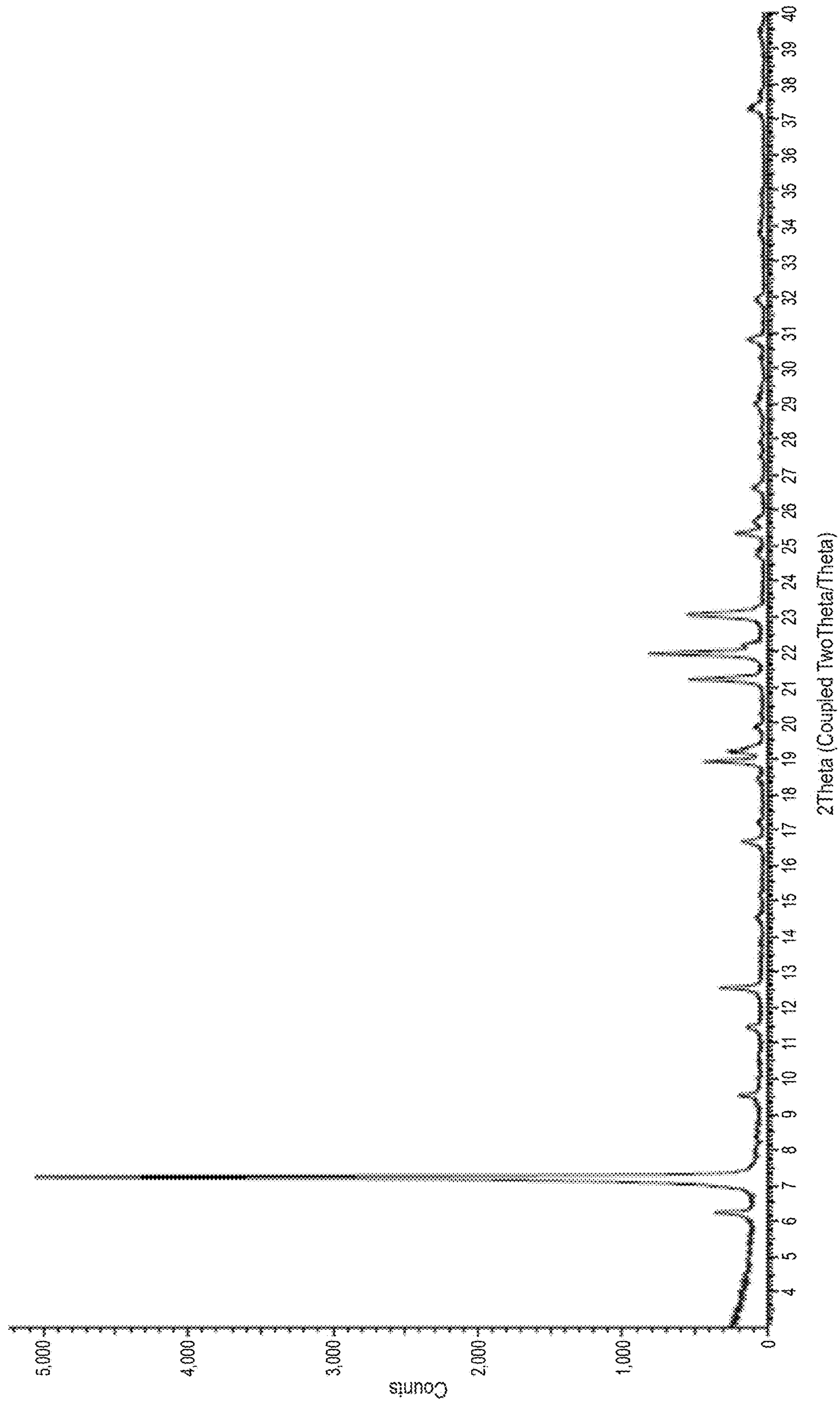
Figure 9B:
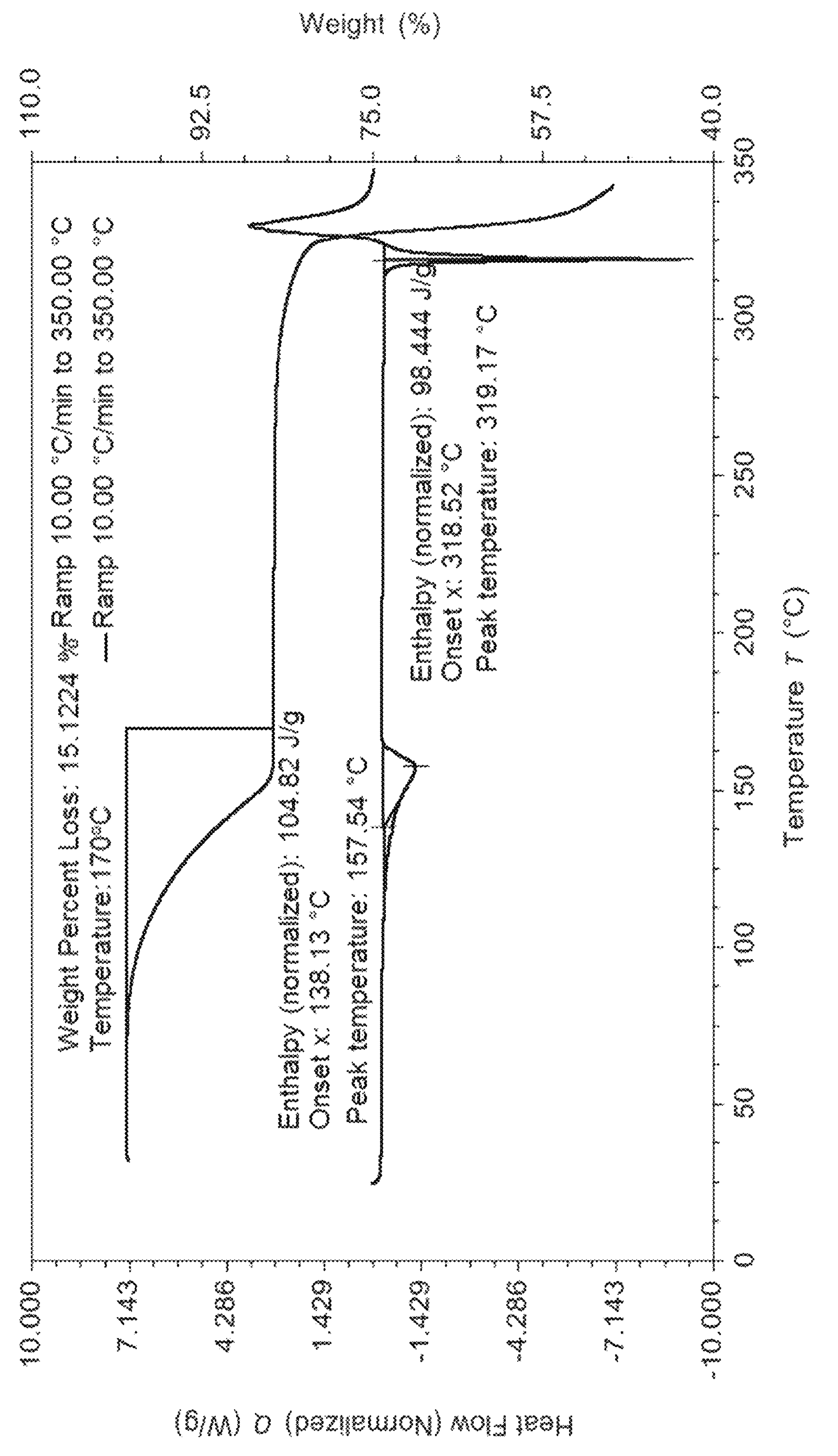

FIG. 9*a* shows a representative X-ray powder diffraction (XRPD) spectrum of crystalline Form IX of Compound 1. FIG. 9*b* shows a representative thermogravimetric analysis (TGA) and differential scanning calorimetry (DSC) analysis of crystalline Form IX of Compound 1.

Figure 10A:
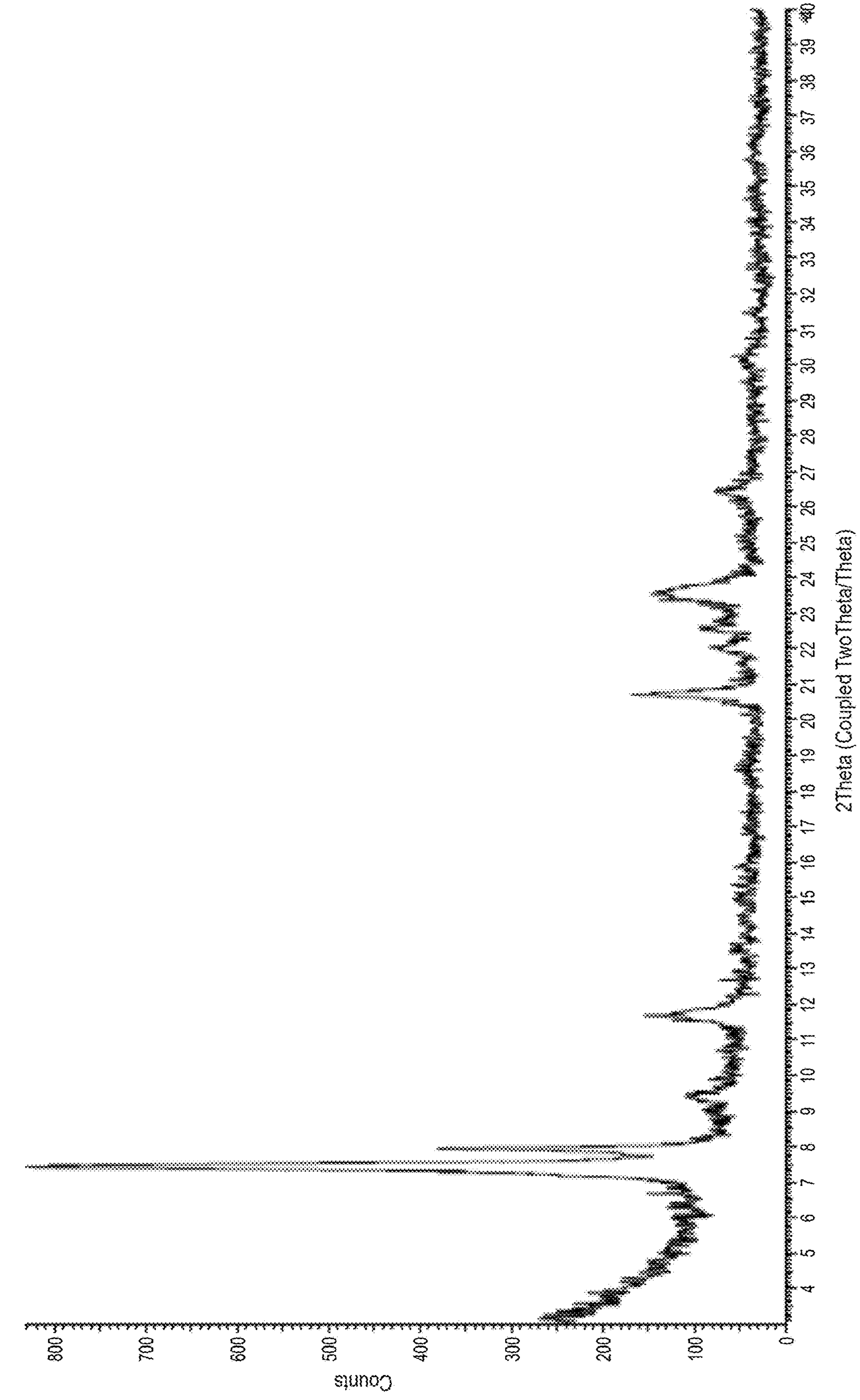
Figure 10B:
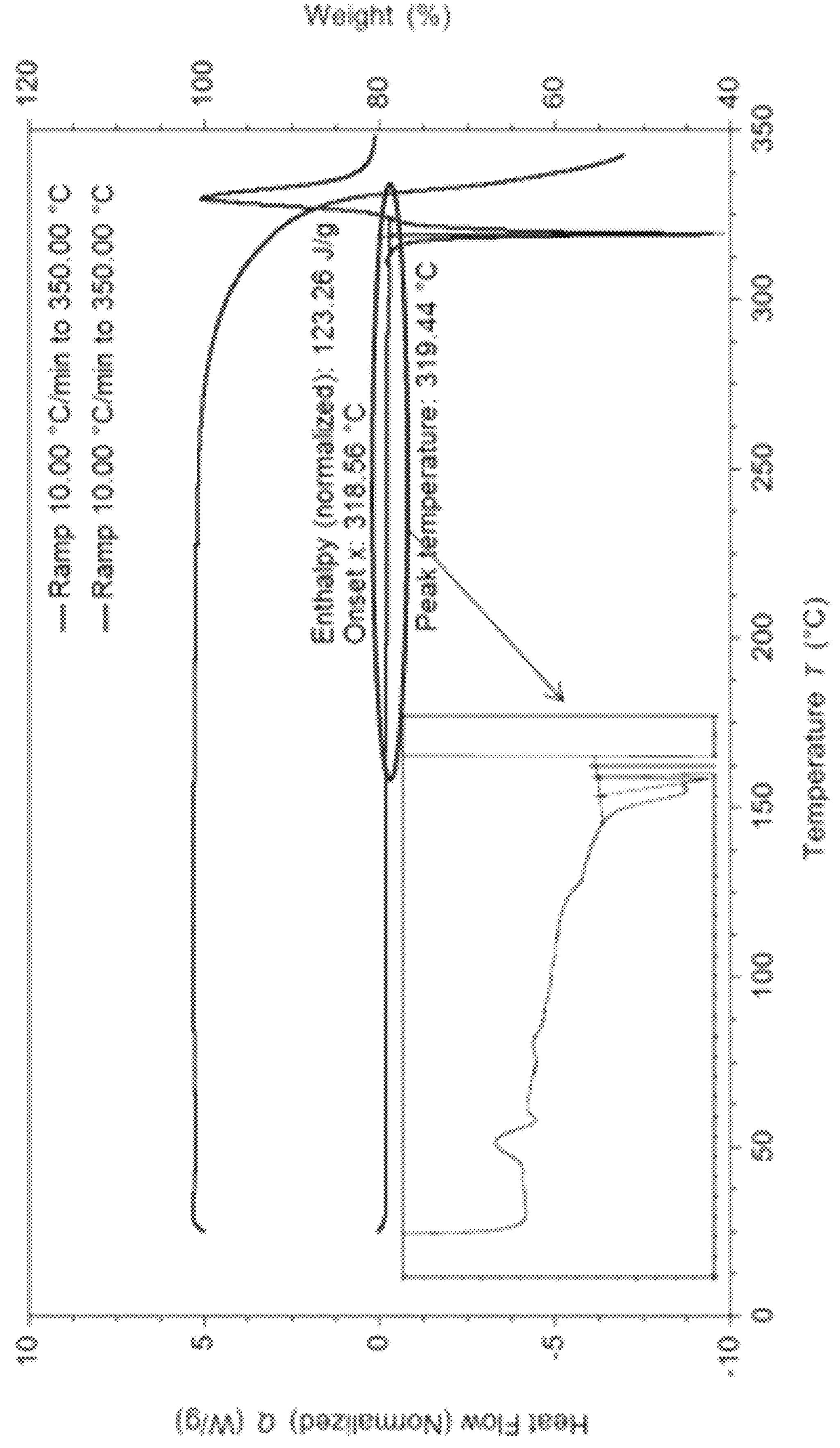

FIG. 10*a* shows a representative X-ray powder diffraction (XRPD) spectrum of crystalline Form X of Compound 1. FIG. 10*b* shows a representative thermogravimetric analysis (TGA) and differential scanning calorimetry (DSC) analysis of crystalline Form X of Compound 1.

Figure 11A:
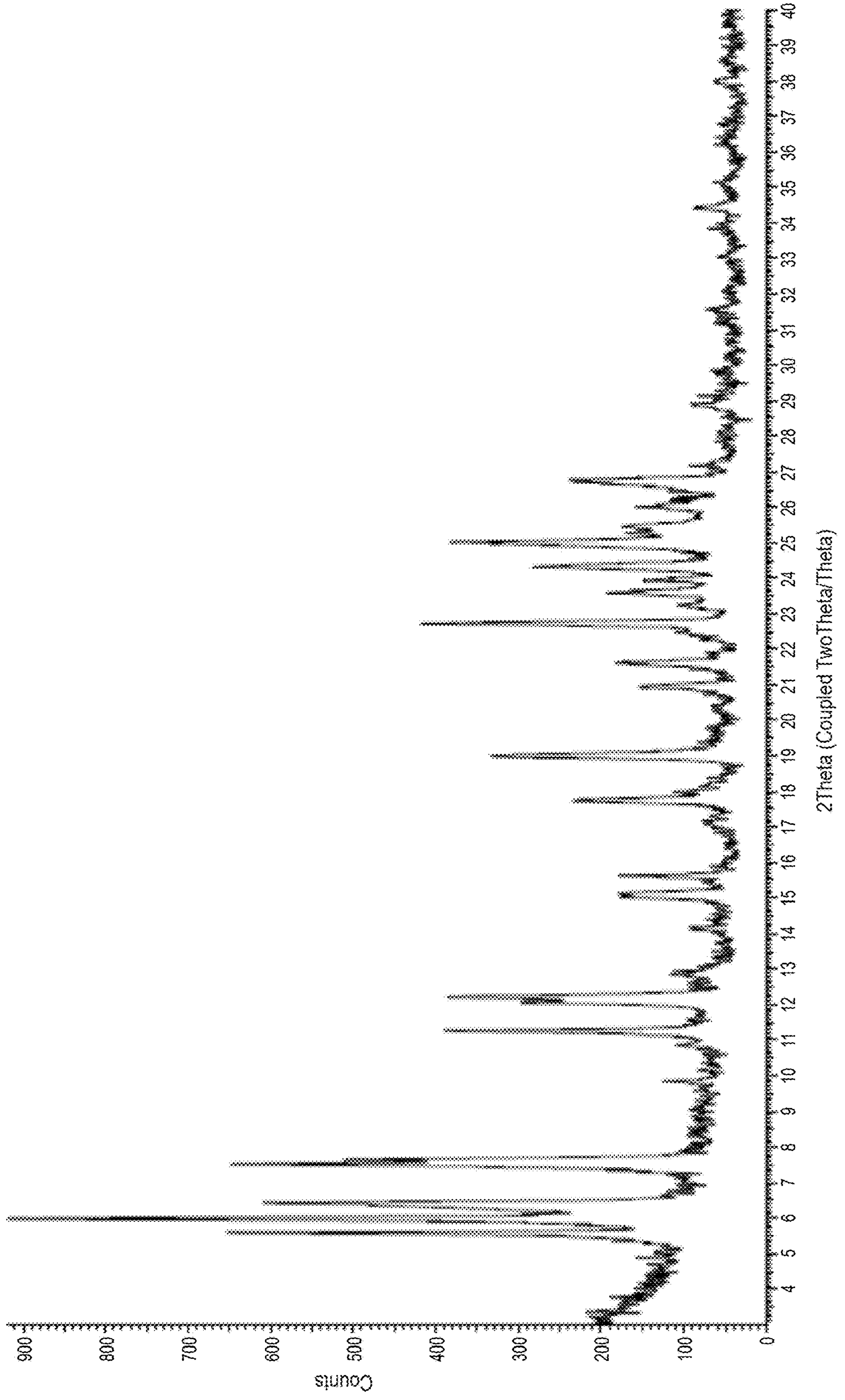
Figure 11B:
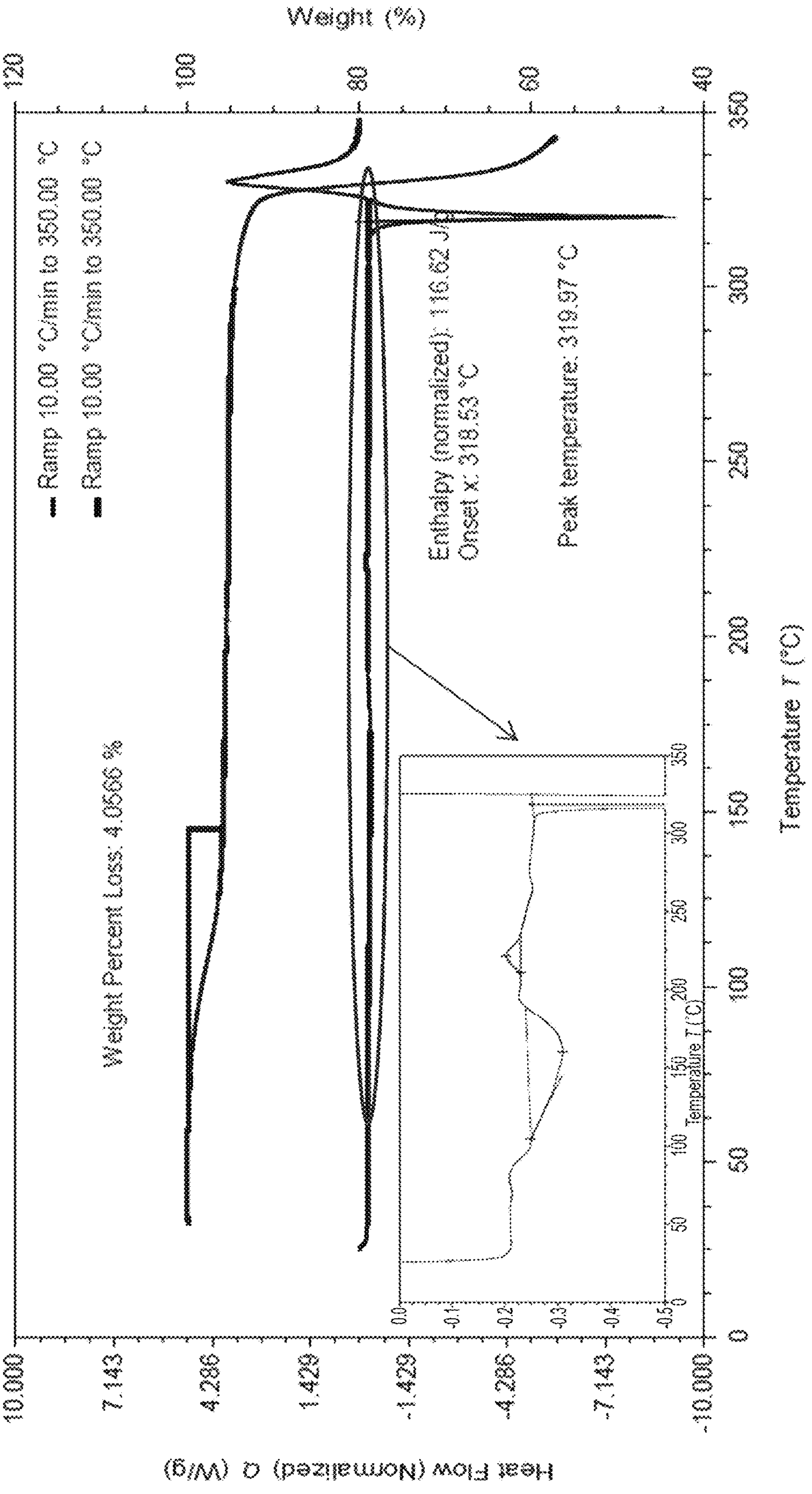

FIG. 11*a* shows a representative X-ray powder diffraction (XRPD) spectrum of crystalline Form XI of Compound 1. FIG. 11*b* shows a representative thermogravimetric analysis (TGA) and differential scanning calorimetry (DSC) analysis of crystalline Form XI of Compound 1.

Figure 12A:
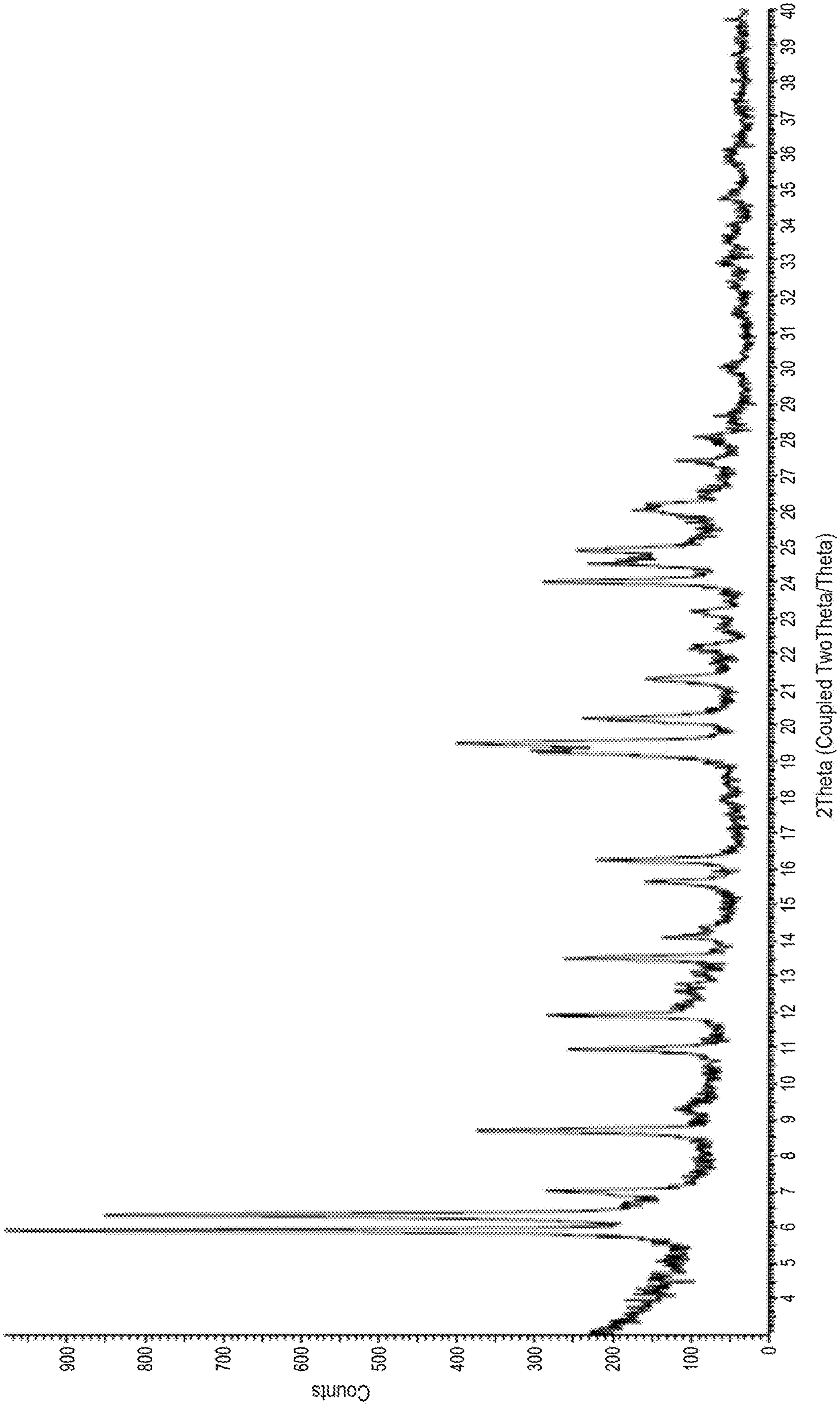
Figure 12B:
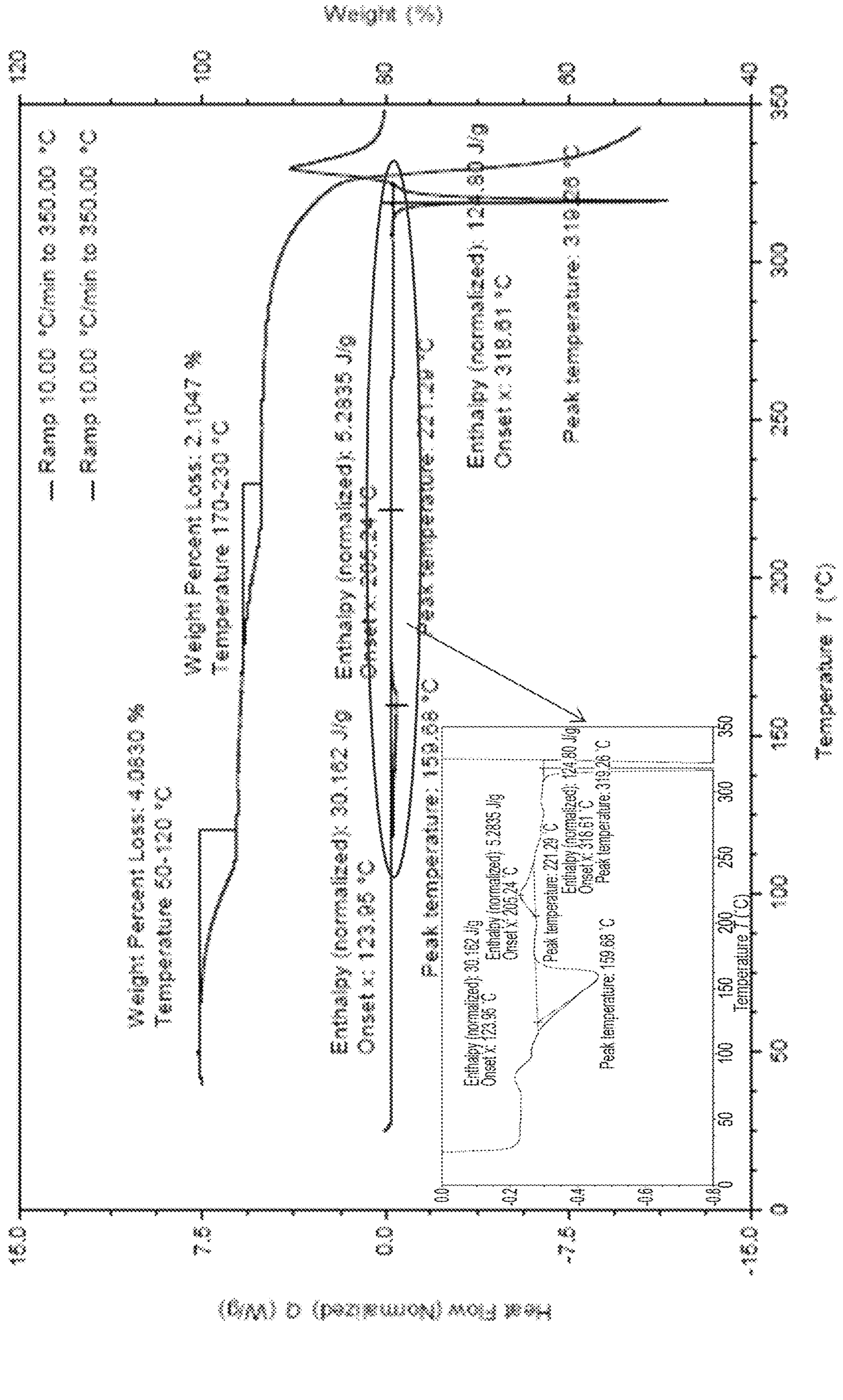

FIG. 12*a* shows a representative X-ray powder diffraction (XRPD) spectrum of crystalline Form XII of Compound 1. FIG. 12*b* shows a representative thermogravimetric analysis (TGA) and differential scanning calorimetry (DSC) analysis of crystalline Form XII of Compound 1.

Figure 13A:
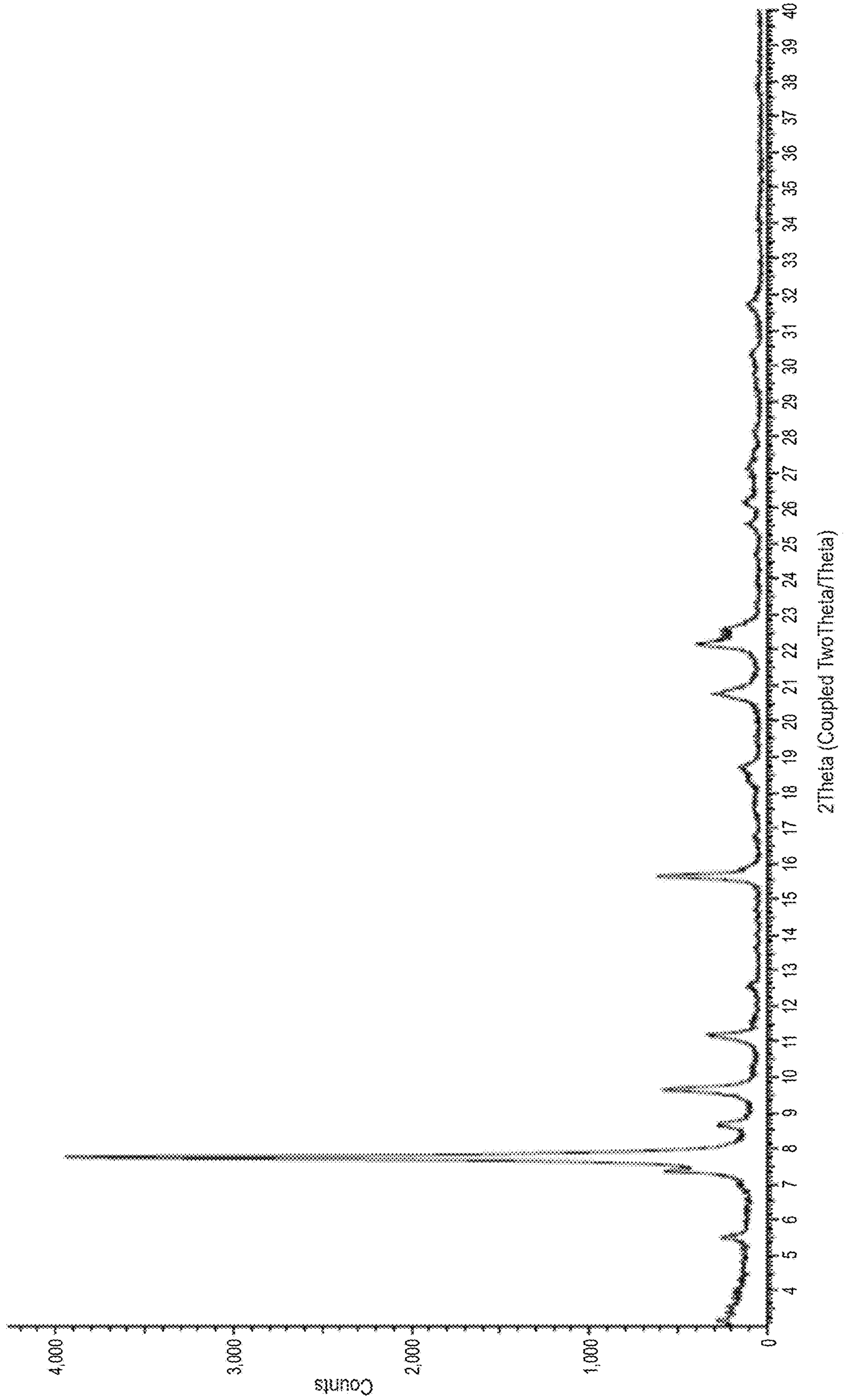
Figure 13B:
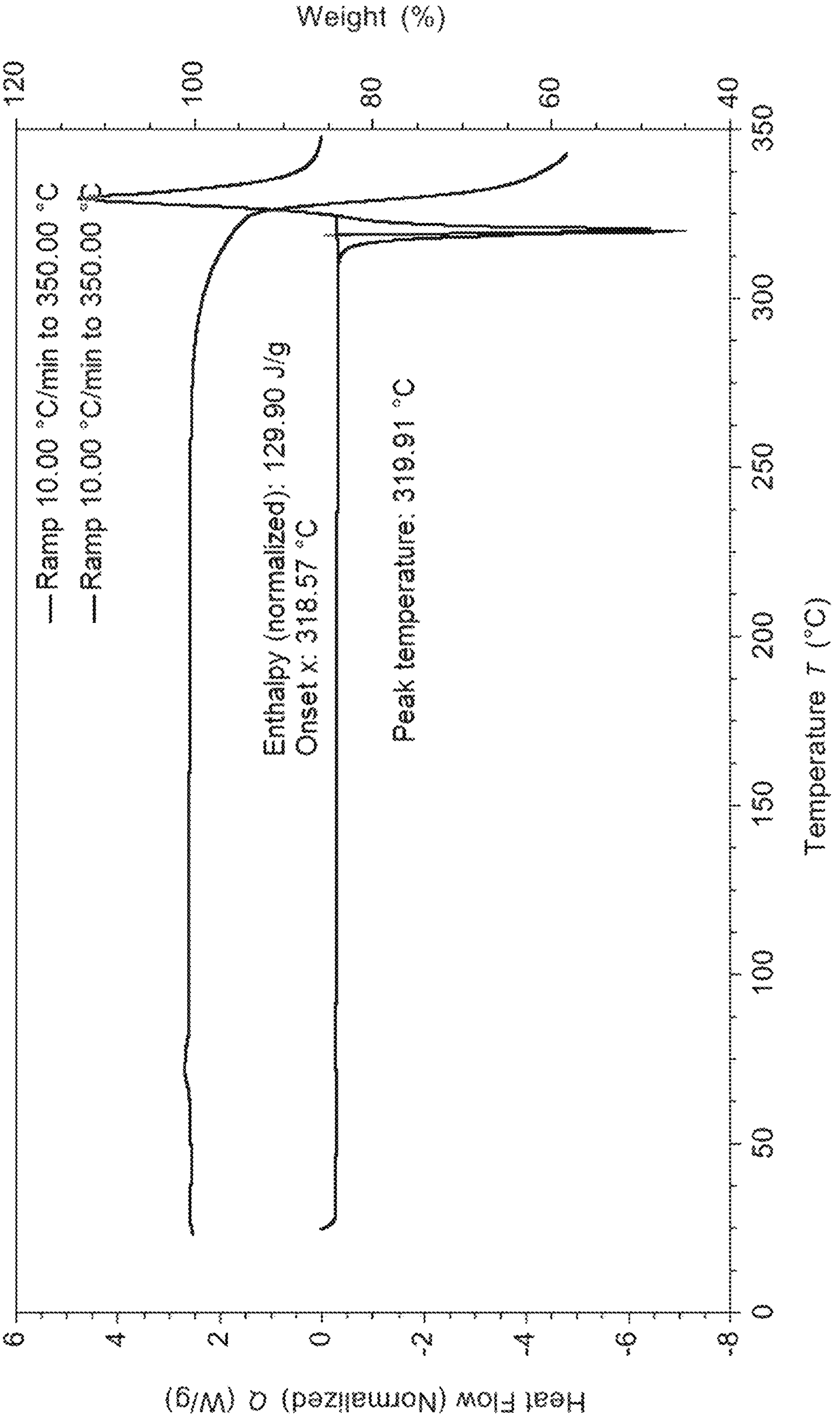

FIG. 13*a* shows a representative X-ray powder diffraction (XRPD) spectrum of crystalline Form XIII of Compound 1. FIG. 13*b* shows a representative thermogravimetric analysis (TGA) and differential scanning calorimetry (DSC) analysis of crystalline Form XIII of Compound 1.

Figure 14A:
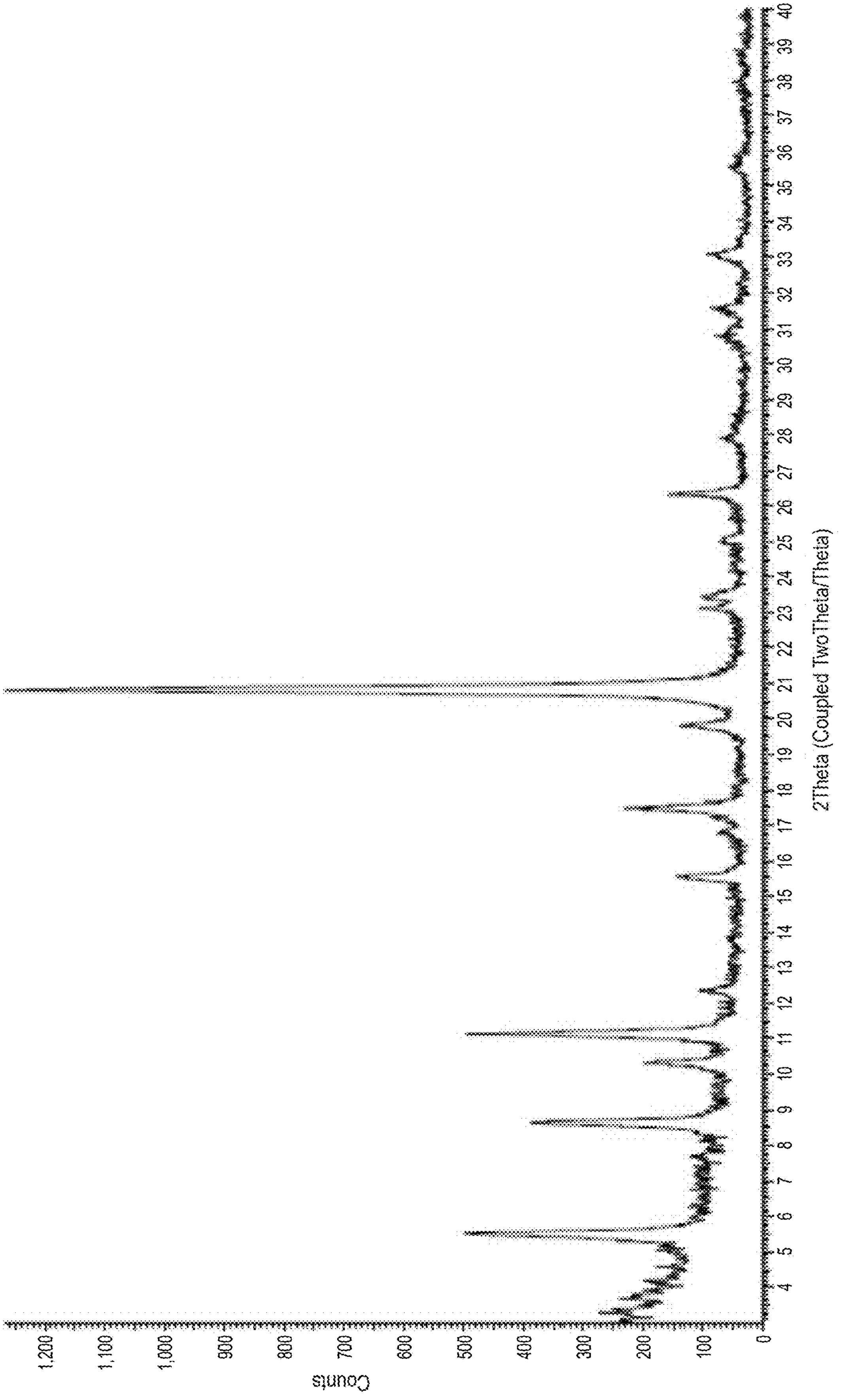
Figure 14B:
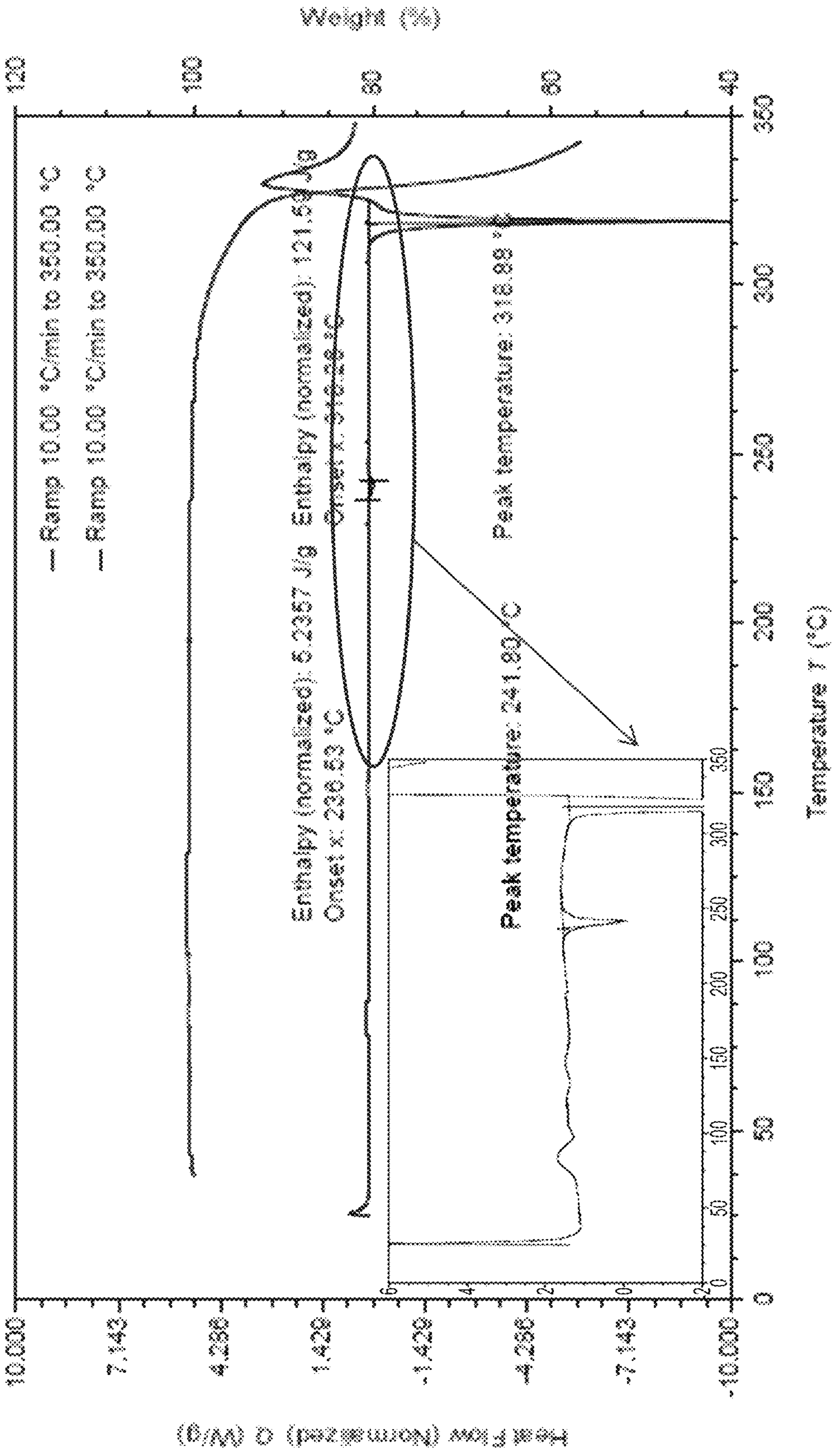

FIG. 14*a* shows a representative X-ray powder diffraction (XRPD) spectrum of crystalline Form XIV of Compound 1. FIG. 14*b* shows a representative thermogravimetric analysis (TGA) and differential scanning calorimetry (DSC) analysis of crystalline Form XIV of Compound 1.

Figure 15A:
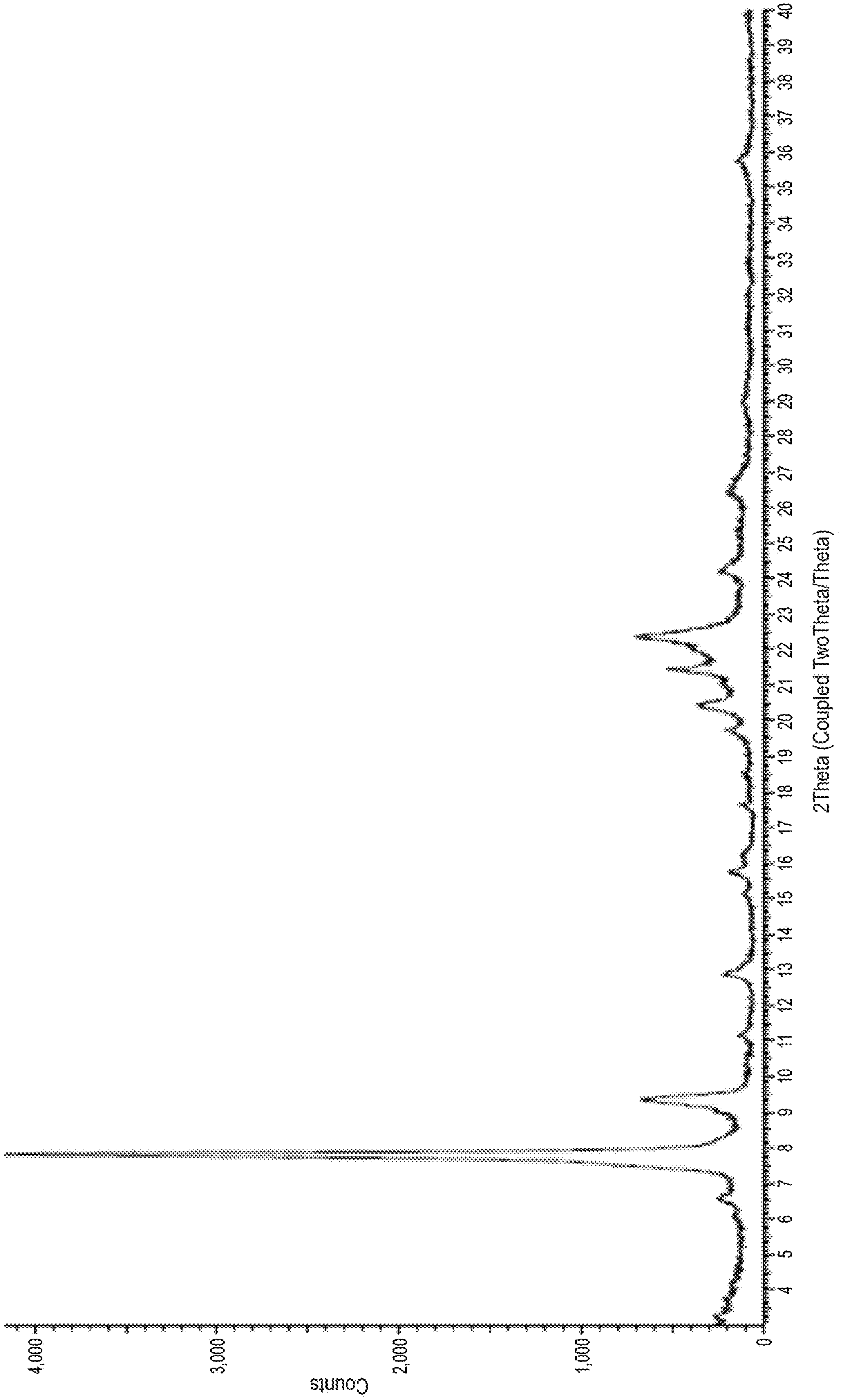
Figure 15B:
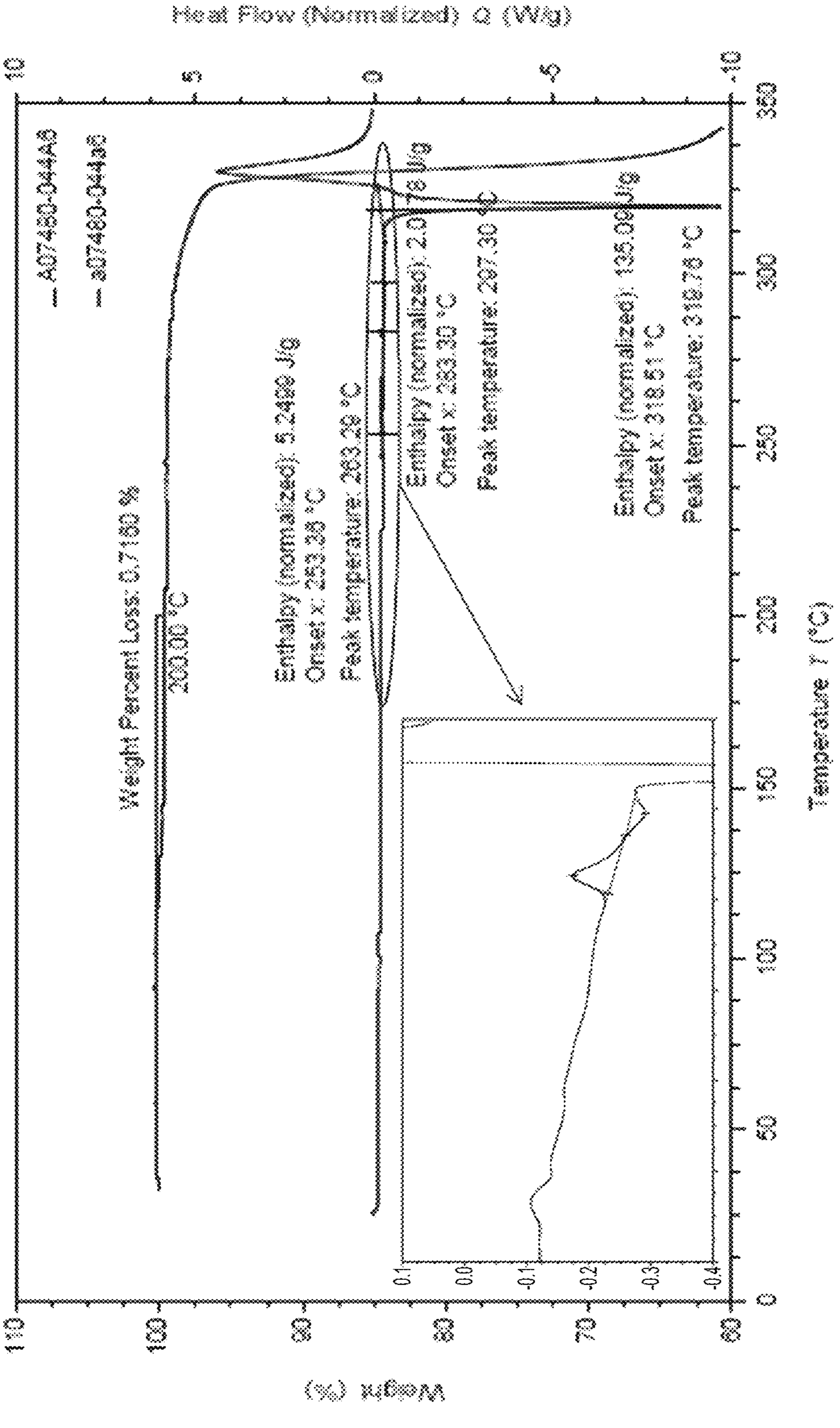

FIG. 15*a* shows a representative X-ray powder diffraction (XRPD) spectrum of crystalline Form XV of Compound 1. FIG. 15*b* shows a representative thermogravimetric analysis (TGA) and differential scanning calorimetry (DSC) analysis of crystalline Form XV of Compound 1.

FIG. 16*a* shows a representative X-ray powder diffraction (XRPD) spectrum of crystalline Form XVI of Compound 1. FIG. 16*b* shows a representative thermogravimetric analysis (TGA) and differential scanning calorimetry (DSC) analysis of crystalline Form XVI of Compound 1.

FIG. 16B-a shows a representative X-ray powder diffraction (XRPD) spectrum of crystalline Form XVII of Compound 1. FIG. 16B-b shows a representative thermogravimetric analysis (TGA) and differential scanning calorimetry (DSC) analysis of crystalline Form XVII of Compound 1. FIG. 16B-c shows a representative $^1$H-NMR spectrum of crystalline Form XVII of Compound 1.

Figure 17A:
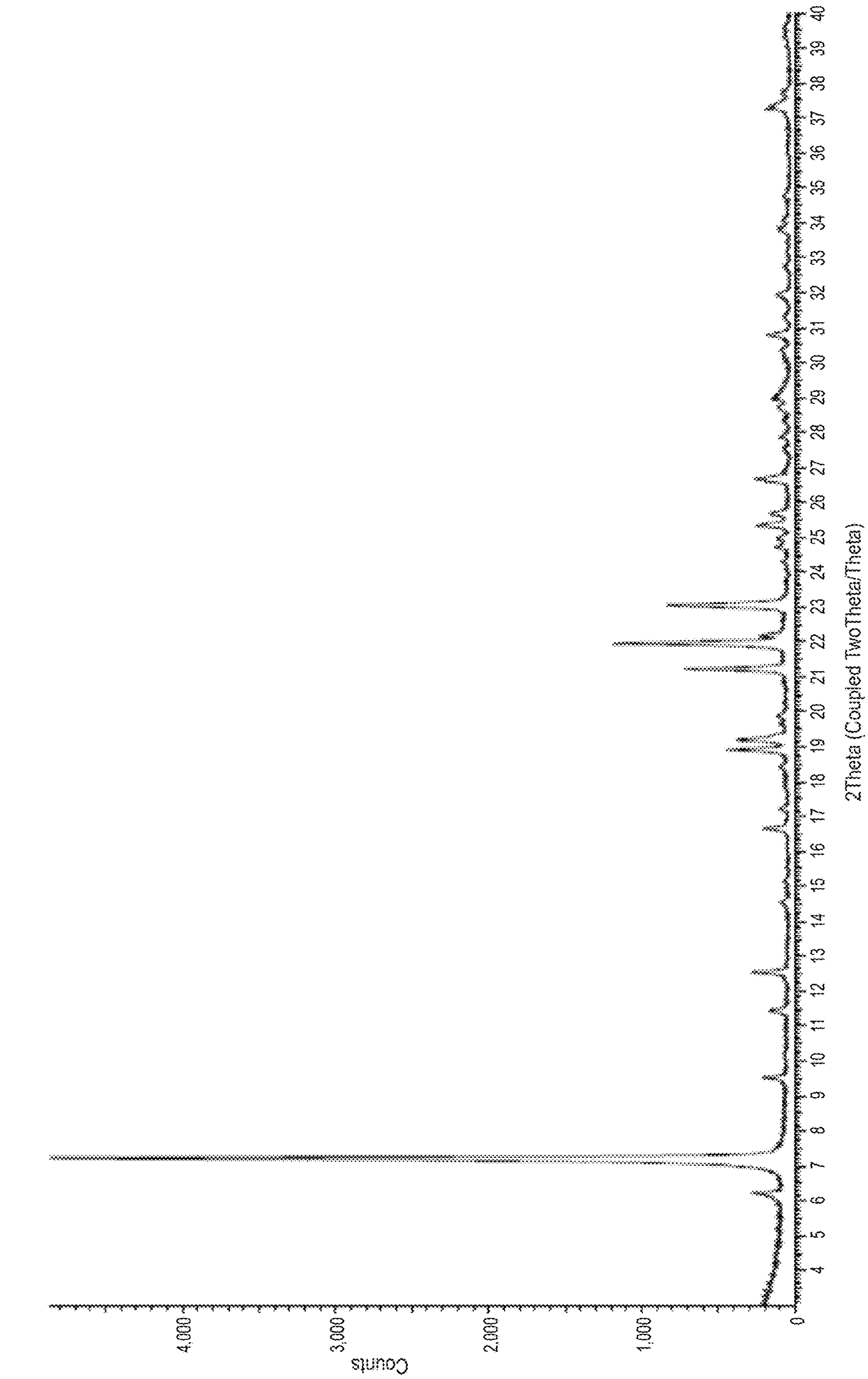
Figure 17B:
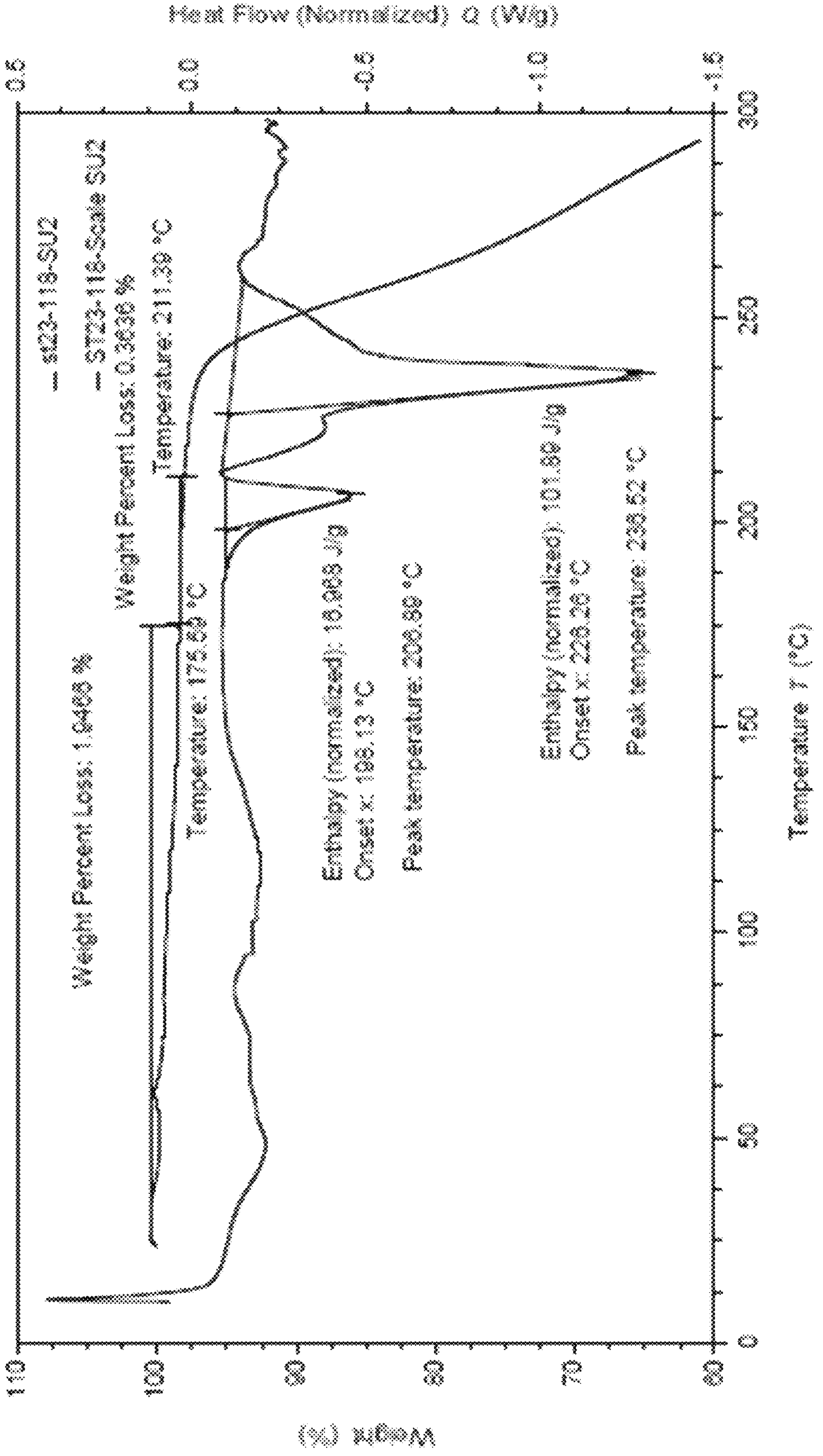
Figure 17C:
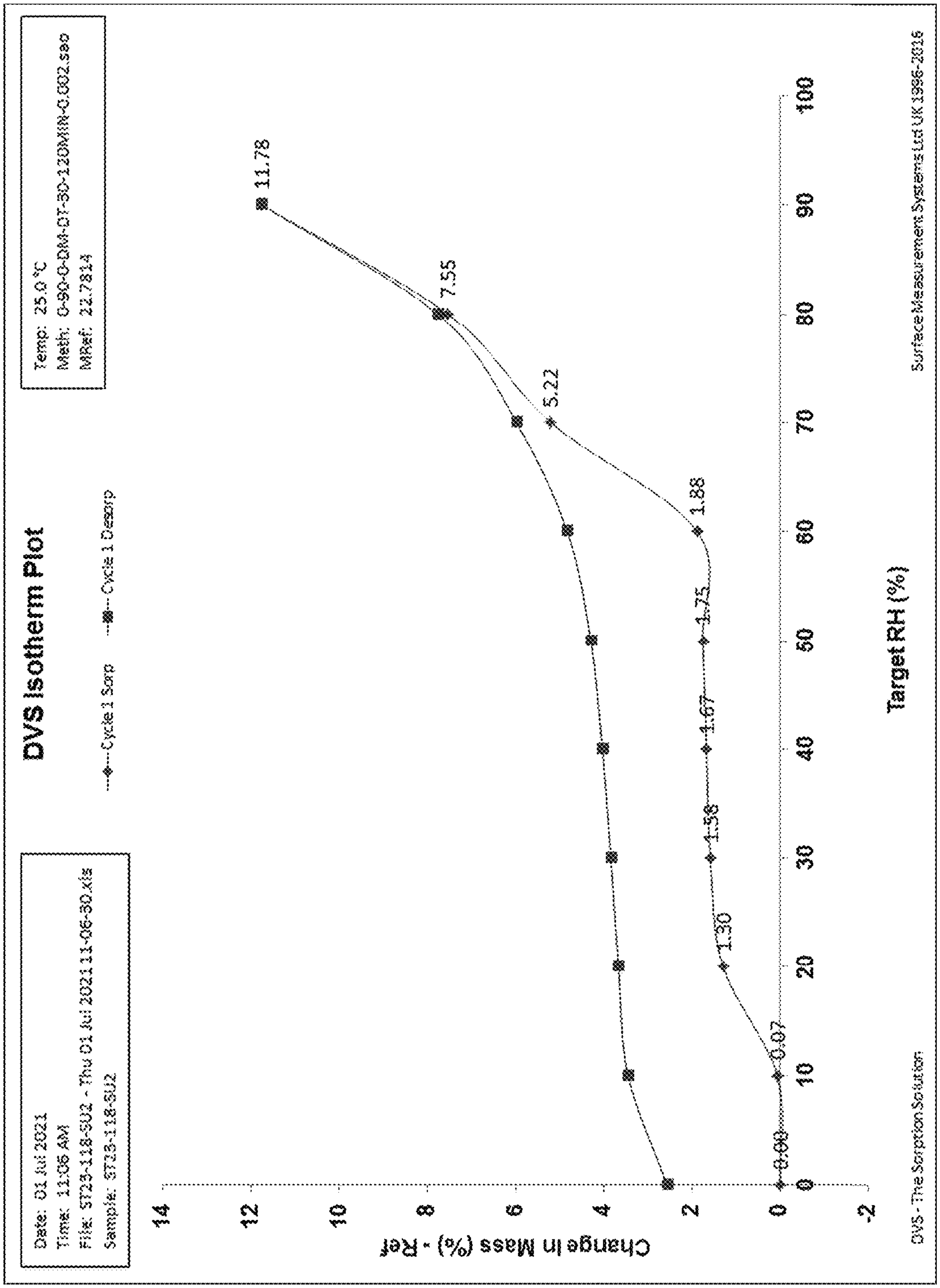

FIG. 17*a* shows a representative X-ray powder diffraction (XRPD) spectrum of crystalline sulfate Form A of Compound 1. FIG. 17*b* shows a representative thermogravimetric analysis (TGA) and differential scanning calorimetry (DSC) analysis of crystalline sulfate Form A of Compound 1. FIG. 17*c* presents a representative dynamic vapor sorption (DVS) analysis of crystalline sulfate Form A of Compound 1.

Figure 18A:
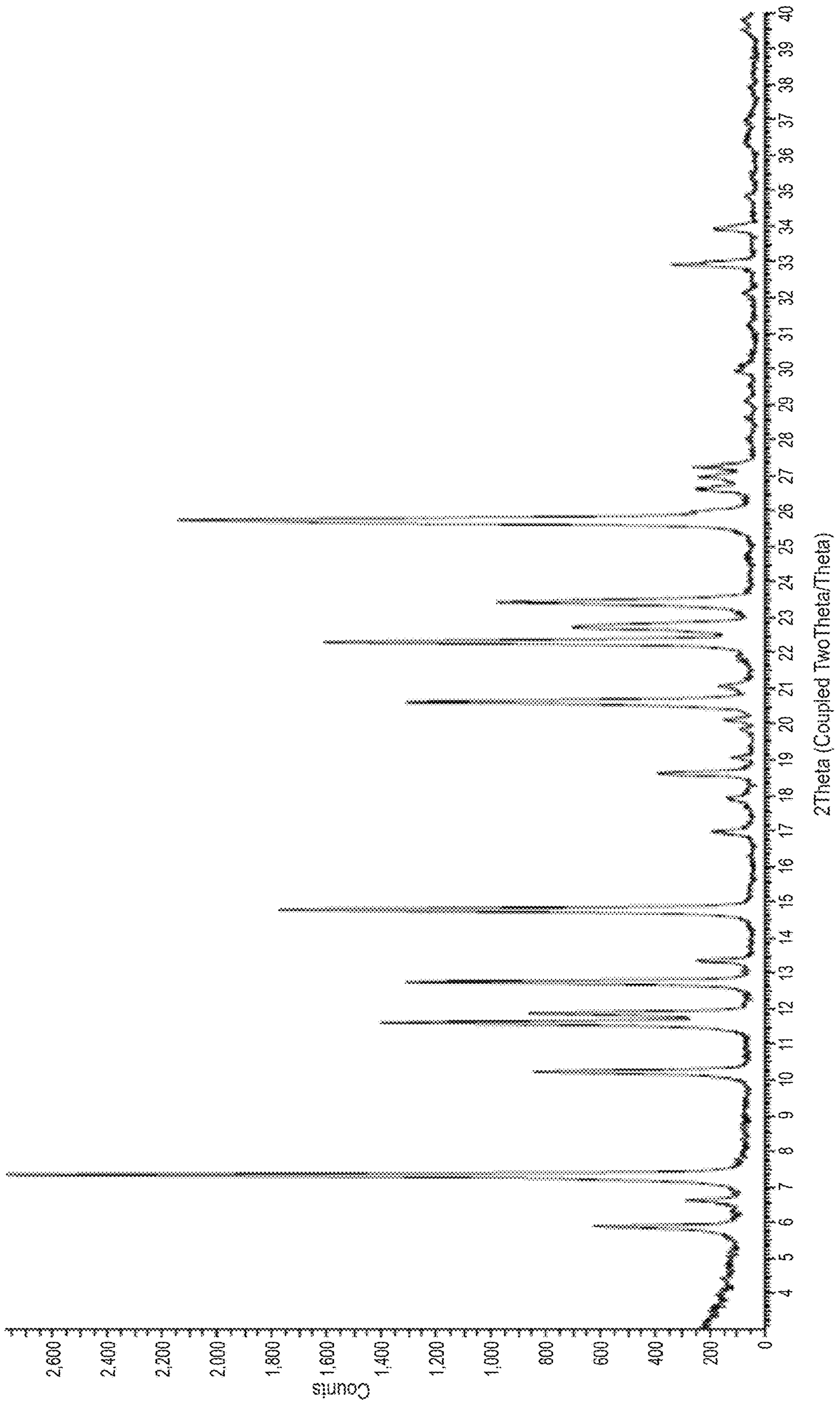
Figure 18B:
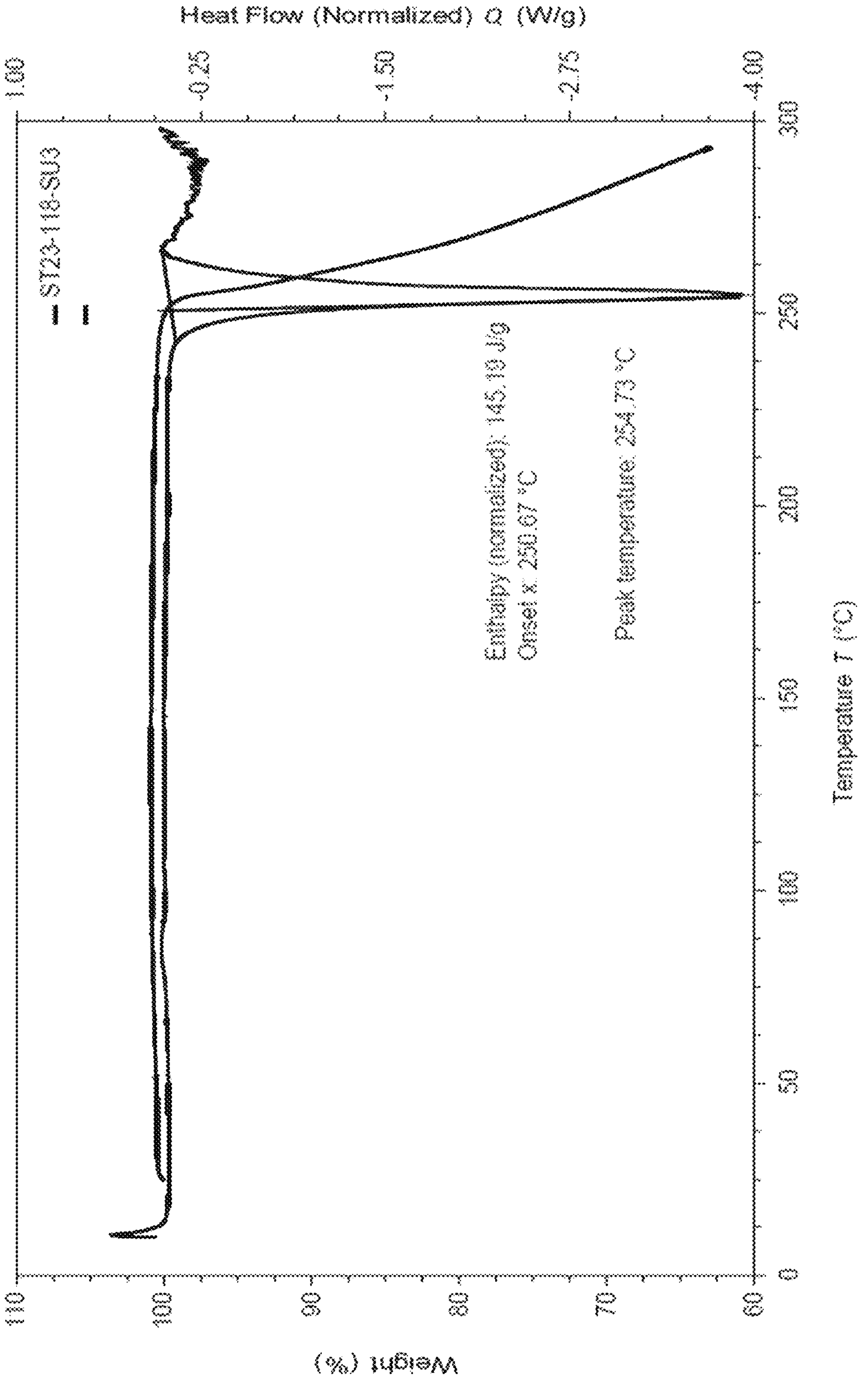
Figure 18C:
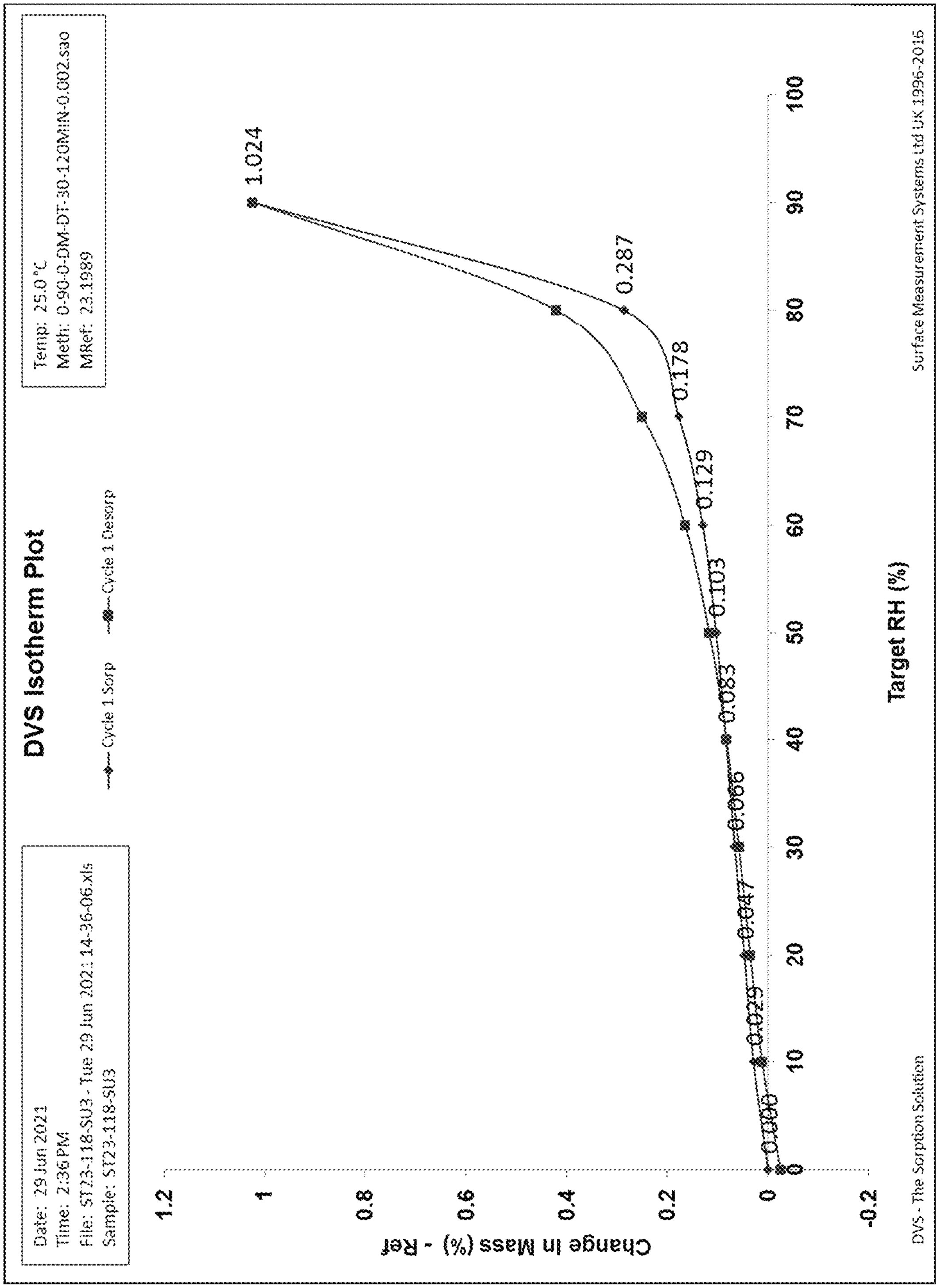

FIG. 18*a* shows a representative X-ray powder diffraction (XRPD) spectrum of crystalline sulfate Form B of Compound 1. FIG. 18*b* shows a representative thermogravimetric analysis (TGA) and differential scanning calorimetry (DSC) analysis of crystalline sulfate Form B of Compound 1. FIG. 18*c* presents a representative dynamic vapor sorption (DVS) analysis of crystalline sulfate Form B of Compound 1.

Figure 19A:
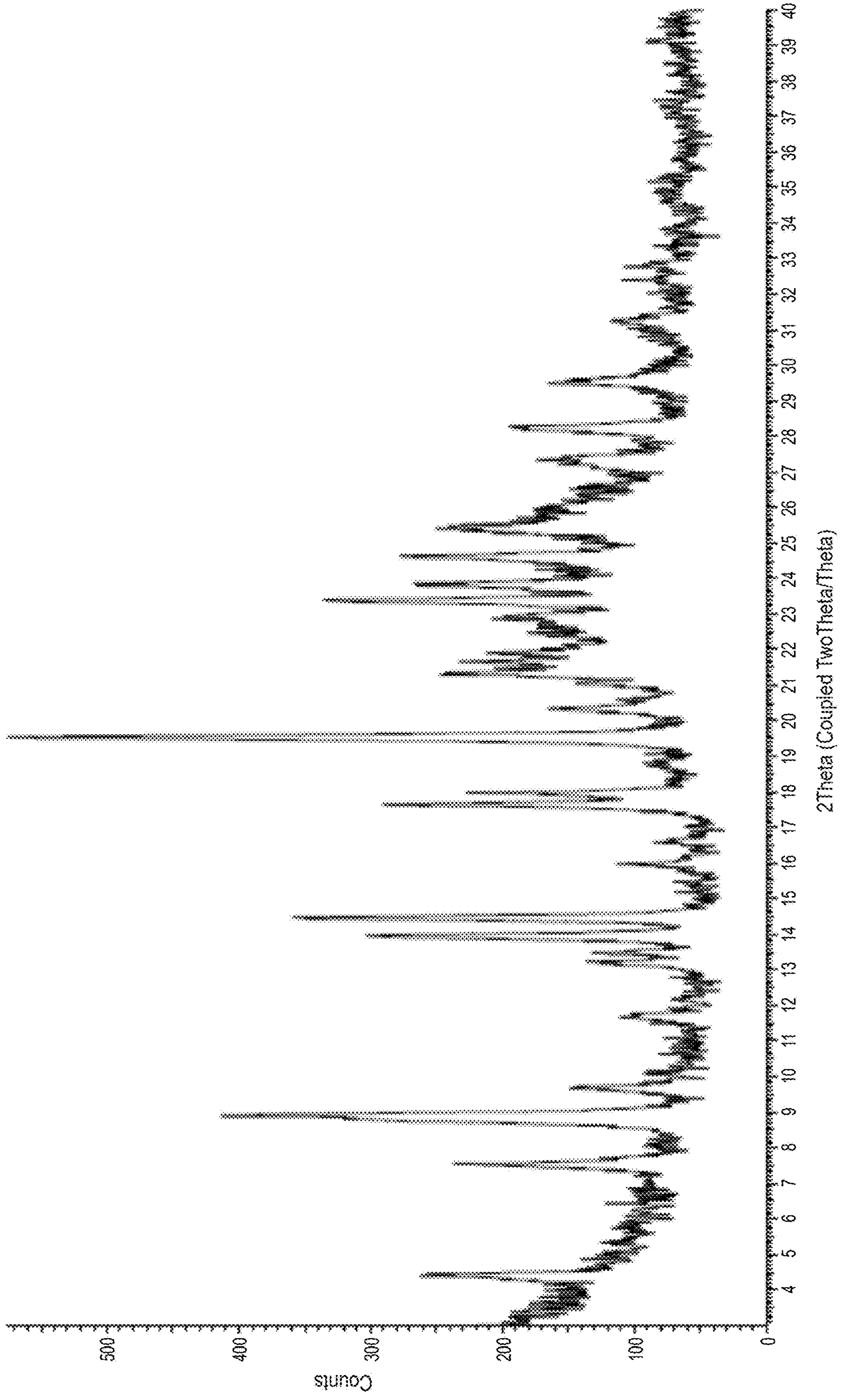
Figure 19B:
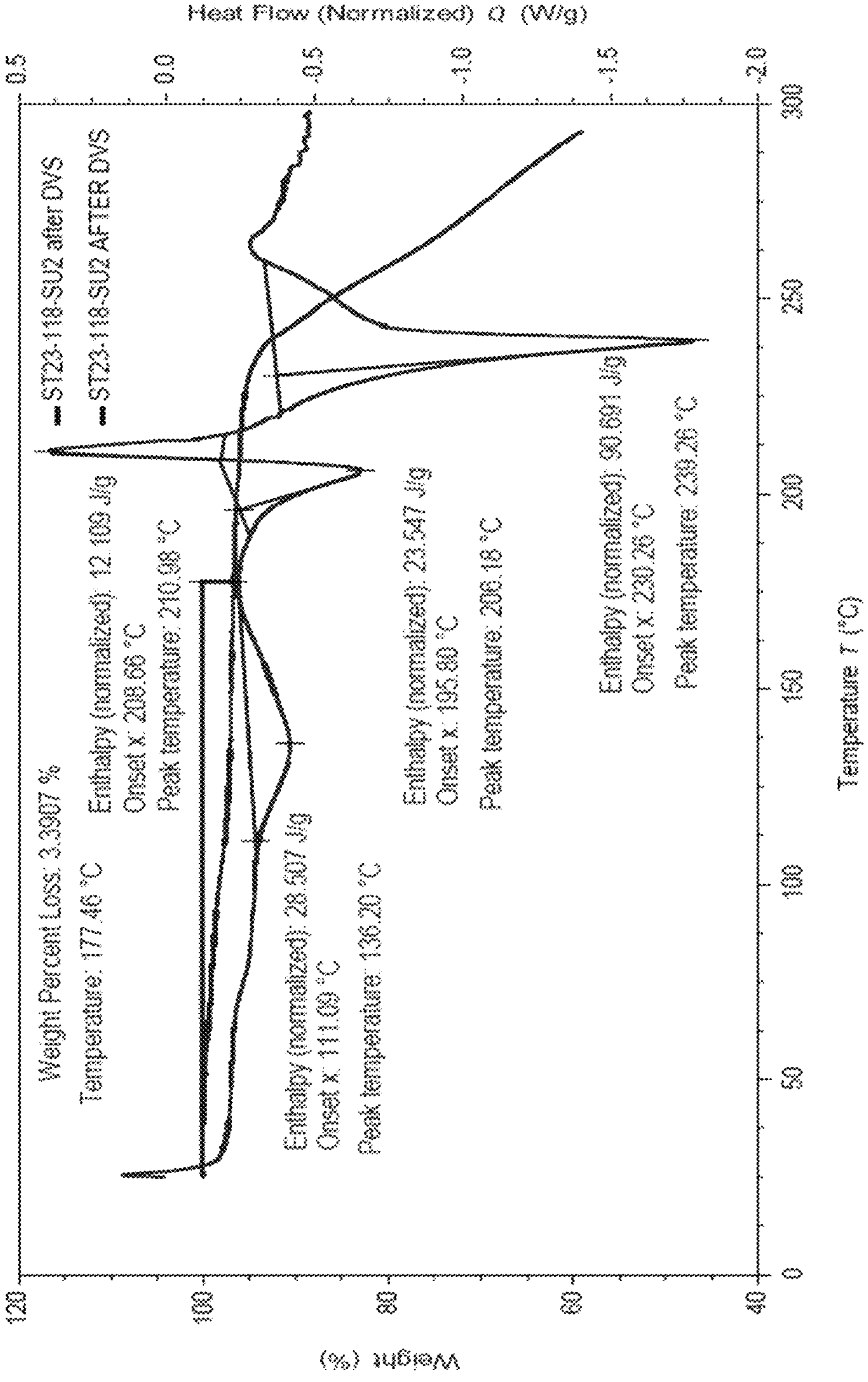

FIG. 19*a* shows a representative X-ray powder diffraction (XRPD) spectrum of crystalline sulfate Form C of Compound 1. FIG. 19*b* shows a representative thermogravimetric analysis (TGA) and differential scanning calorimetry (DSC) analysis of crystalline sulfate Form C of Compound 1.

Figure 20A:
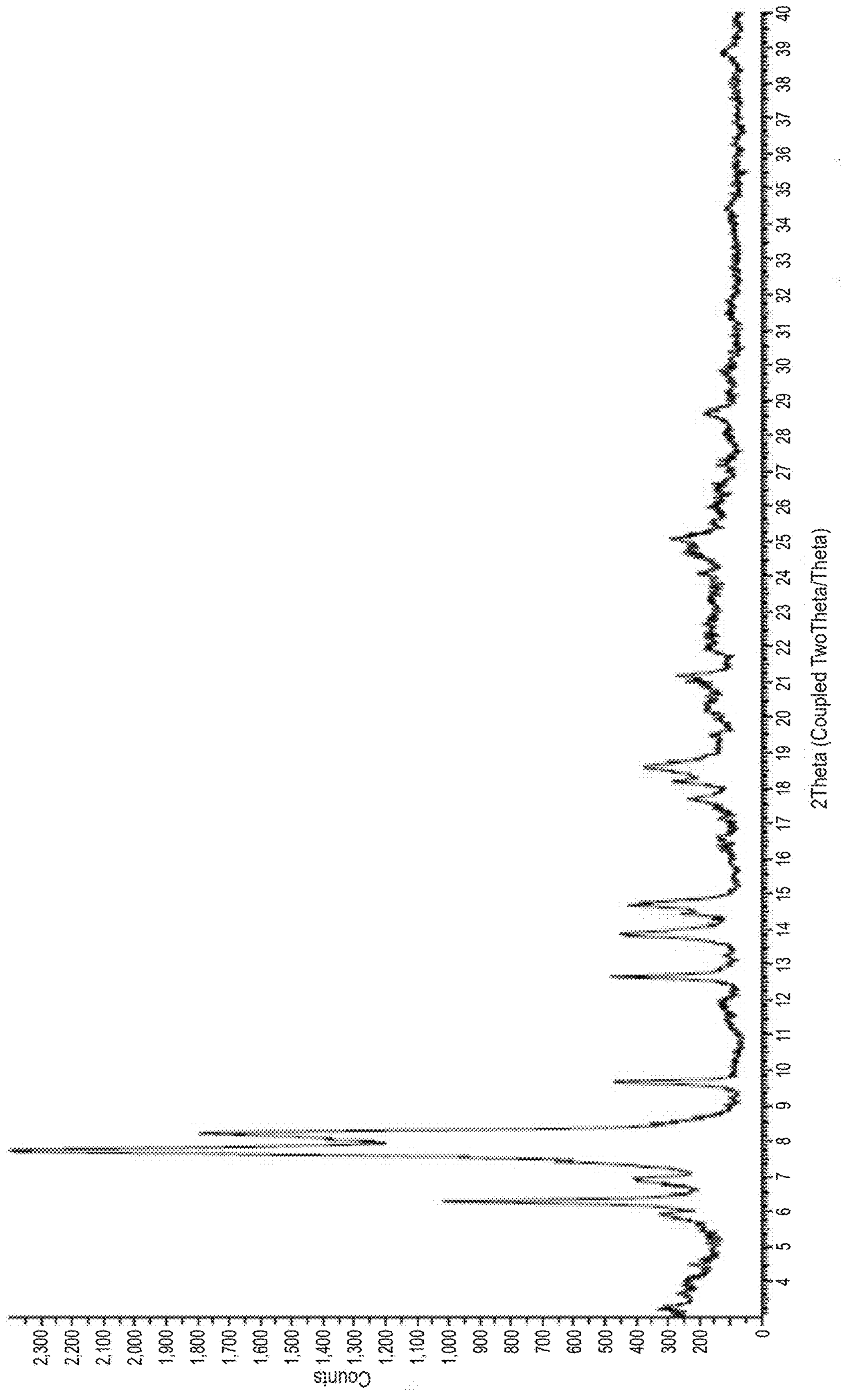
Figure 20B:
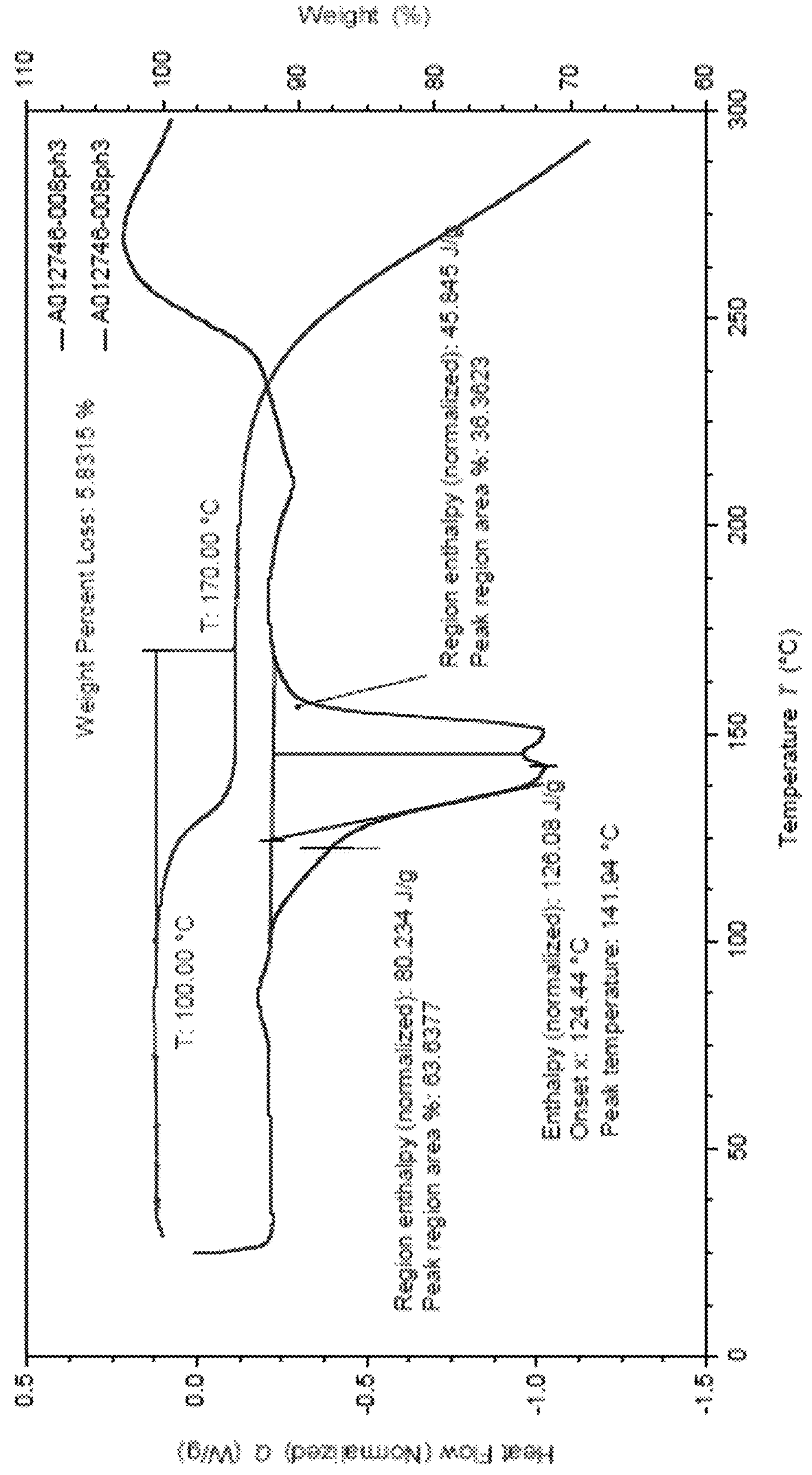

FIG. 20*a* shows a representative X-ray powder diffraction (XRPD) spectrum of crystalline besylate Form D of Compound 1. FIG. 20*b* shows a representative thermogravimetric analysis (TGA) and differential scanning calorimetry (DSC) analysis of crystalline besylate Form D of Compound 1.

Figure 21A:
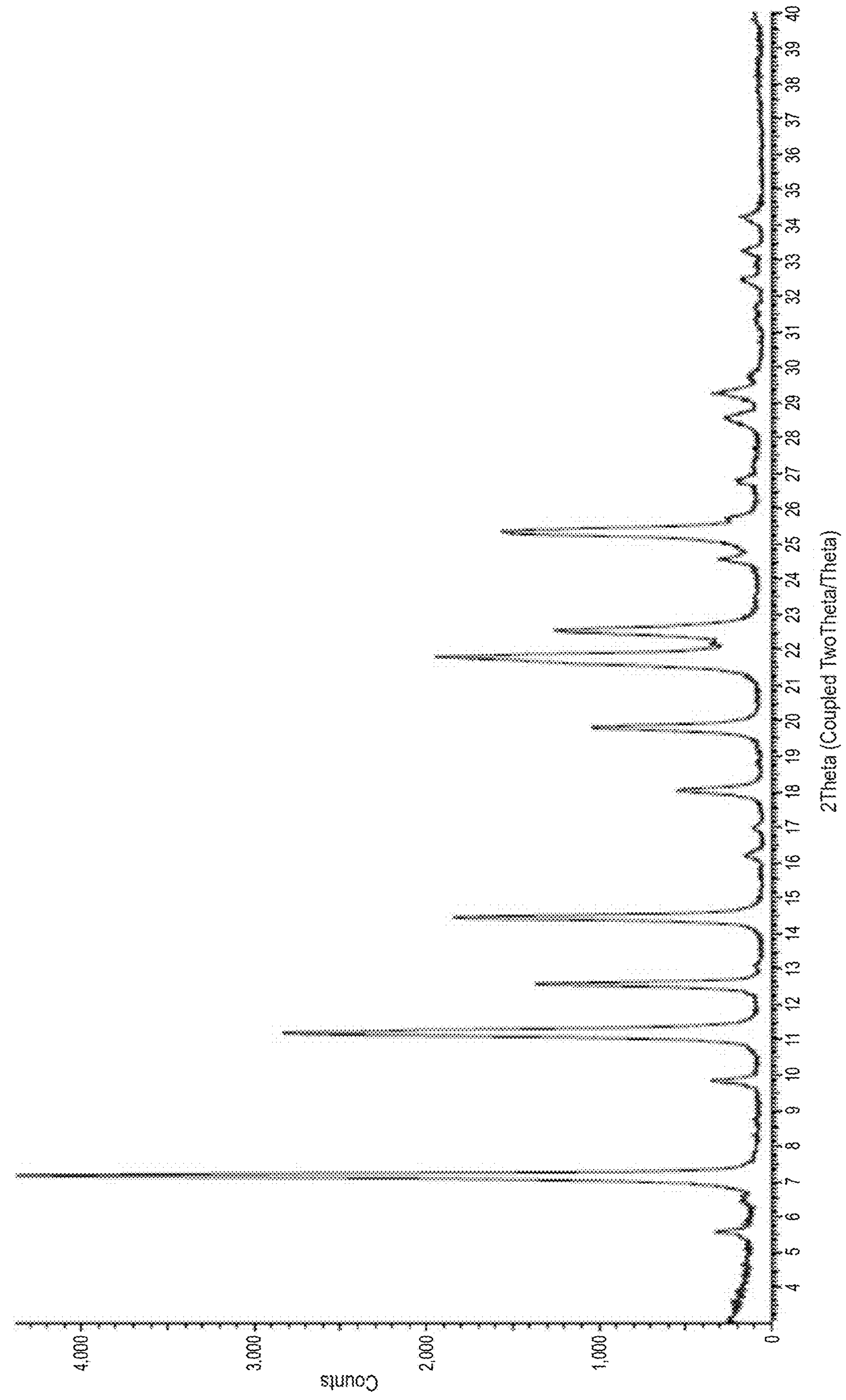
Figure 21B:
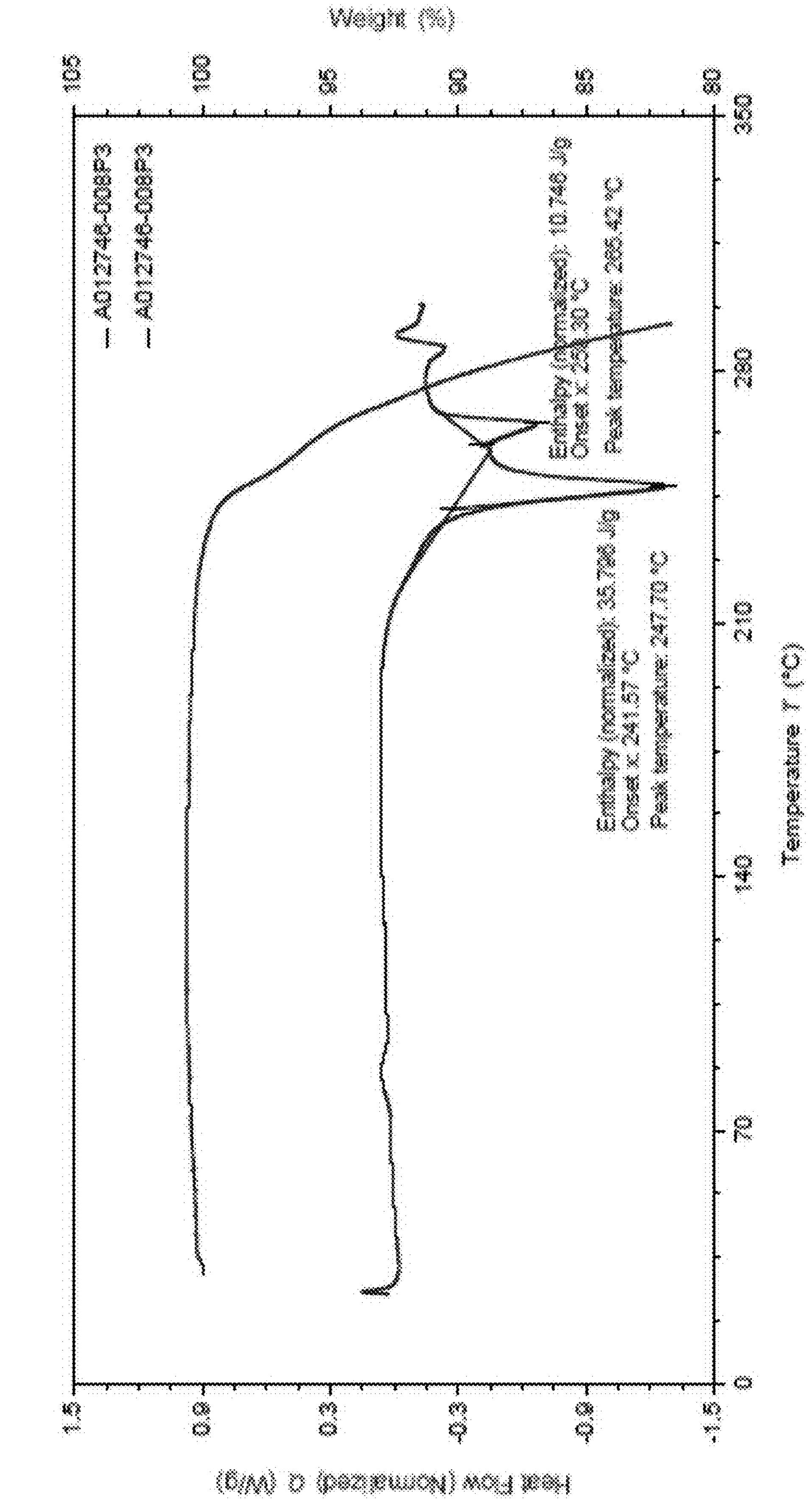
Figure 21C:
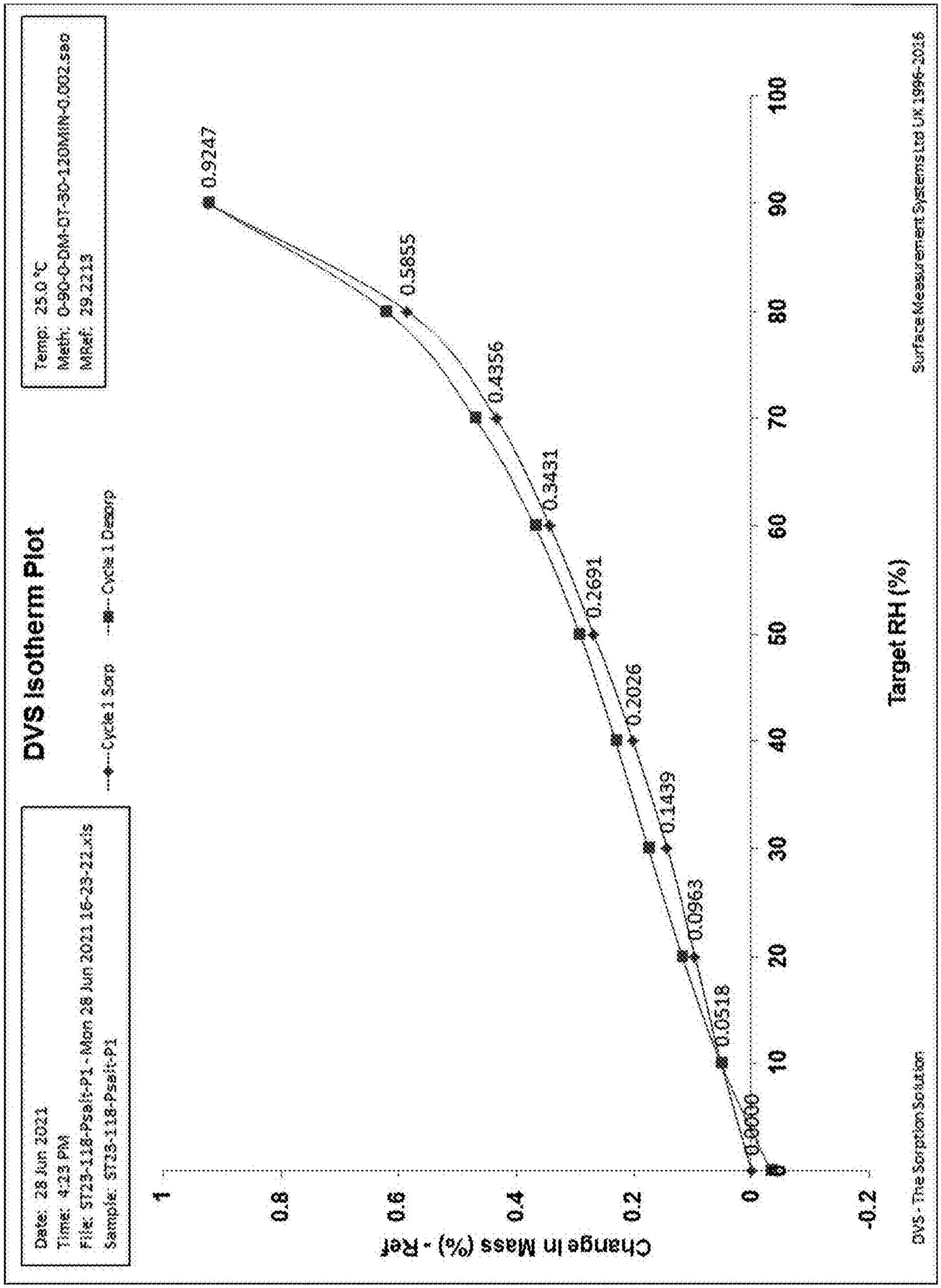

FIG. 21*a* shows a representative X-ray powder diffraction (XRPD) spectrum of crystalline phosphate Form E of Compound 1. FIG. 21*b* shows a representative thermogravimetric analysis (TGA) and differential scanning calorimetry (DSC) analysis of crystalline phosphate Form E of Compound 1. FIG. 21*c* presents a representative dynamic vapor sorption (DVS) analysis of crystalline phosphate Form E of Compound 1.

Figure 22A:
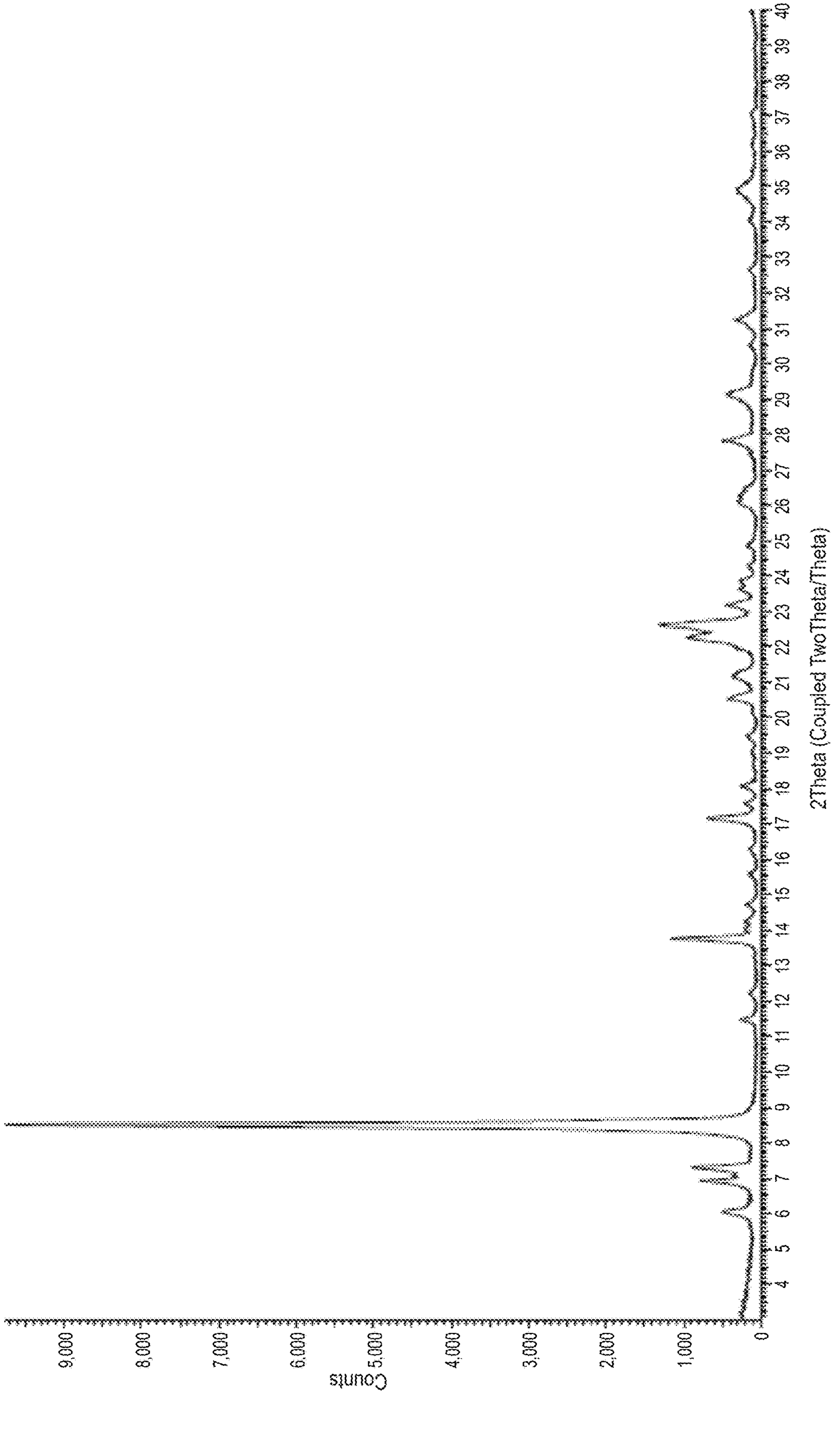
Figure 22B:
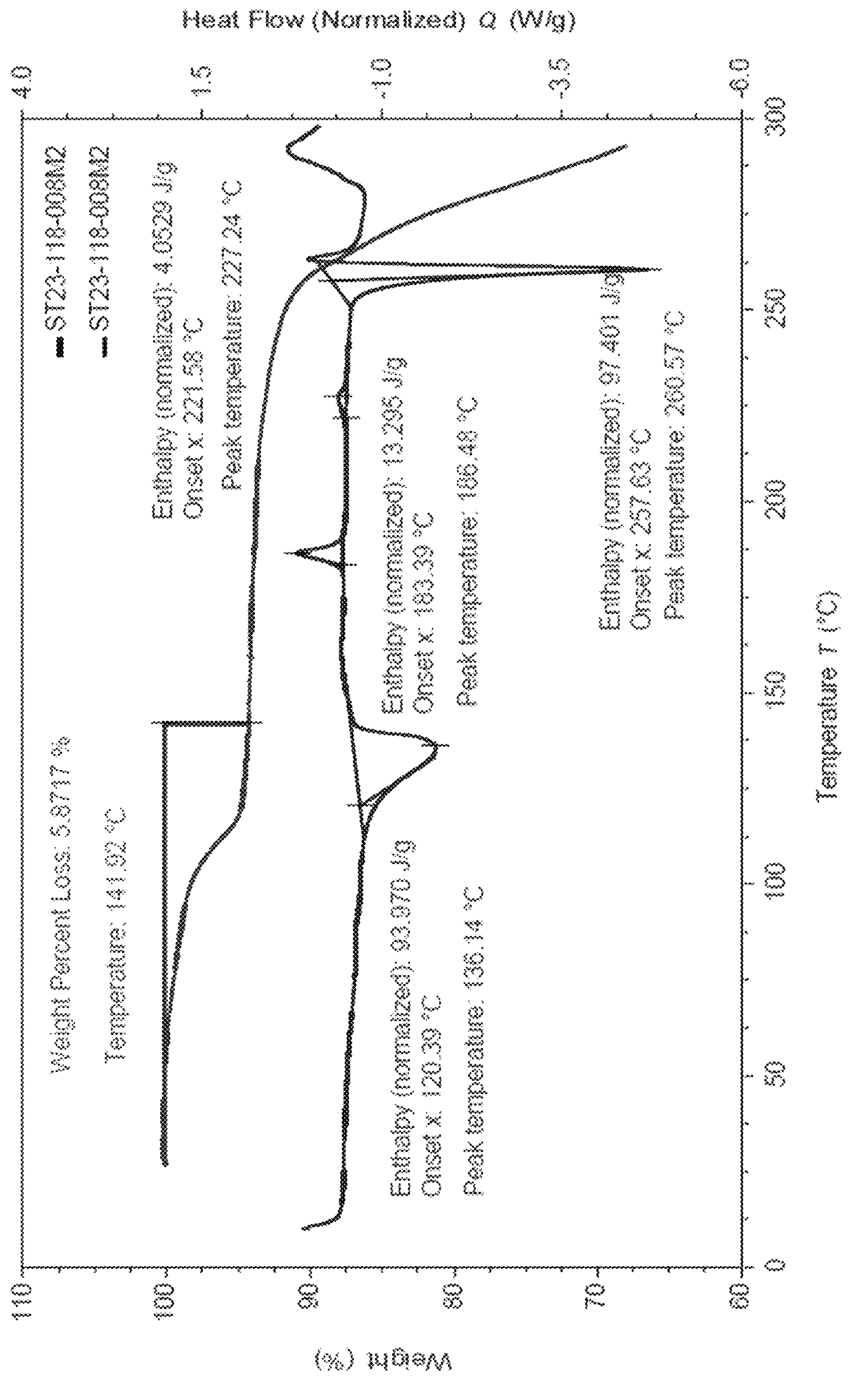

FIG. 22*a* shows a representative X-ray powder diffraction (XRPD) spectrum of crystalline mesylate Form F of Compound 1. FIG. 22*b* shows a representative thermogravimetric analysis (TGA) and differential scanning calorimetry (DSC) analysis of crystalline mesylate Form F of Compound 1.

Figure 23A:
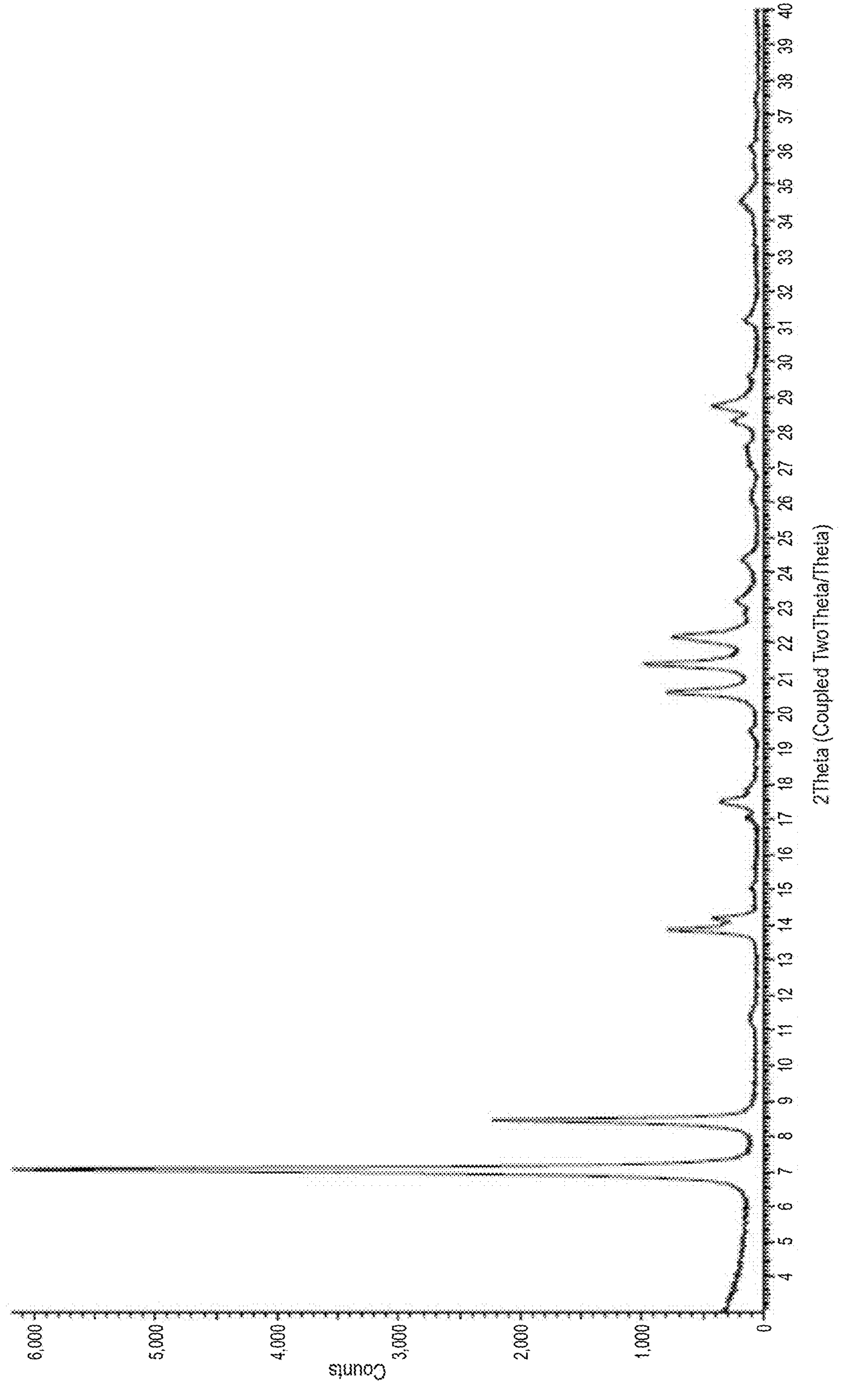
Figure 23B:
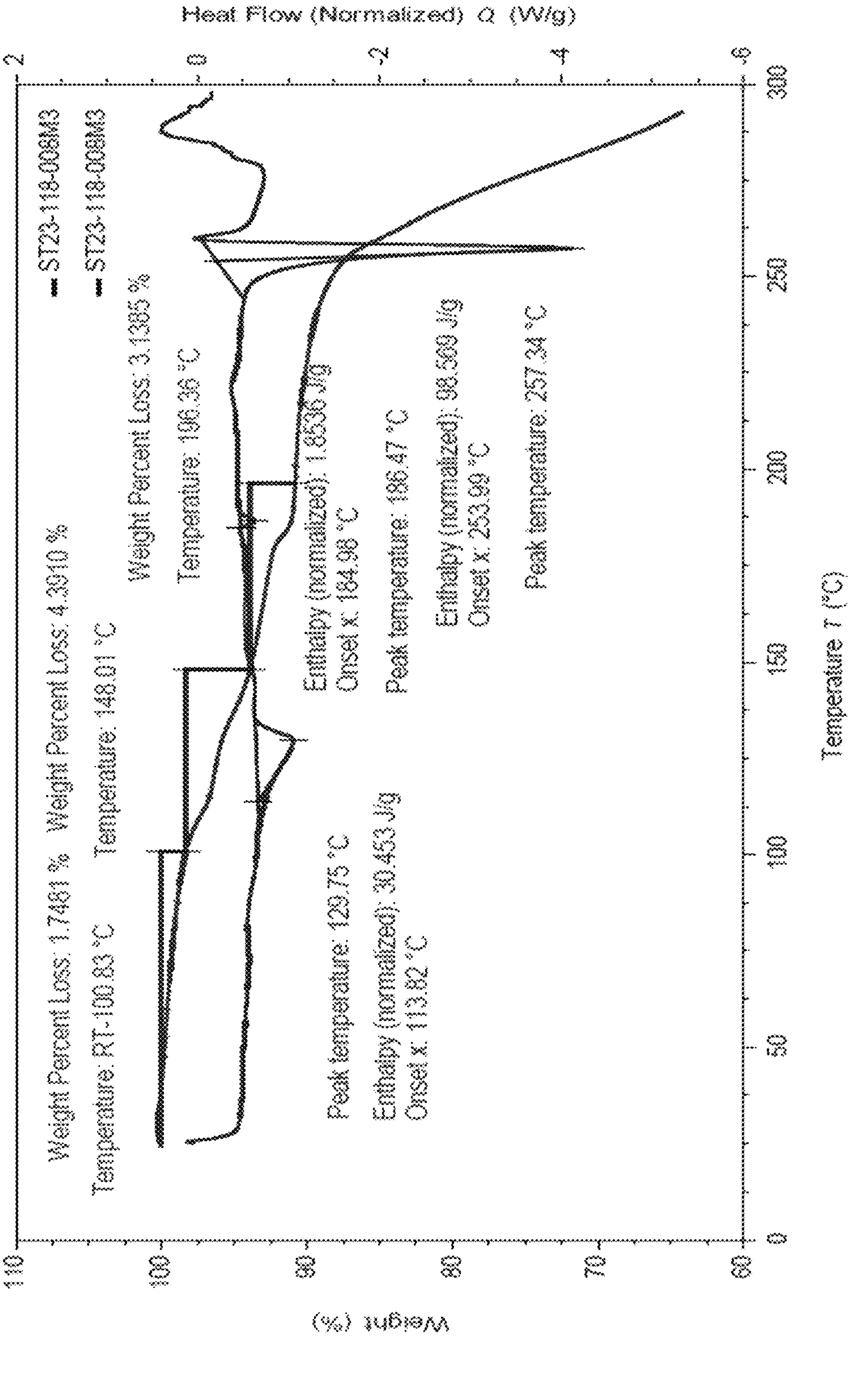
Figure 23C:
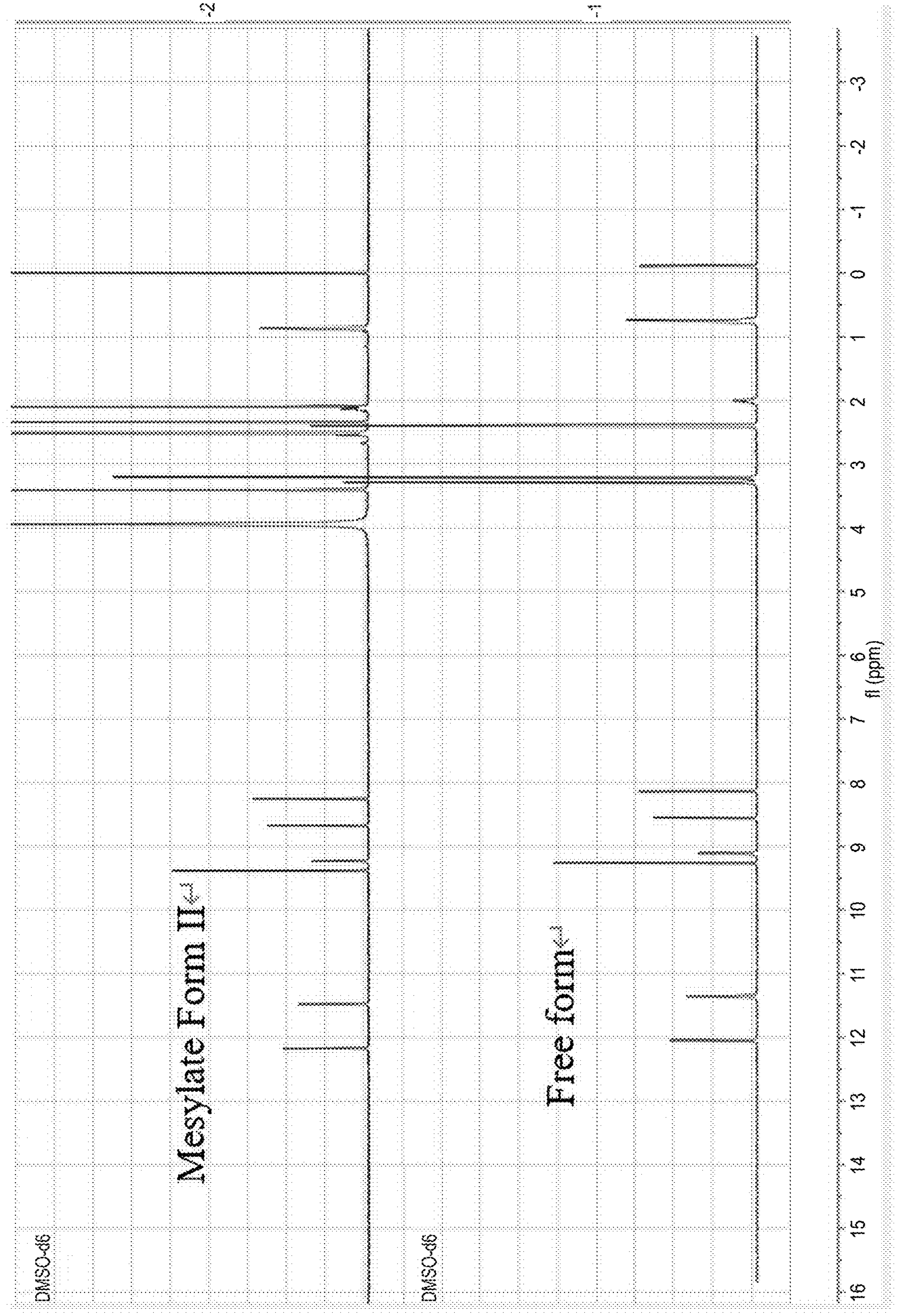

FIG. 23*a* shows a representative X-ray powder diffraction (XRPD) spectrum of crystalline mesylate Form G of Compound 1. FIG. 23*b* shows a representative thermogravimetric analysis (TGA) and differential scanning calorimetry (DSC) analysis of crystalline mesylate Form G of Compound 1. FIG. 23*c* presents a representative $^1$H-NMR spectrum of crystalline mesylate Form G of Compound 1 in comparison with that of its free form.

Figure 24A:
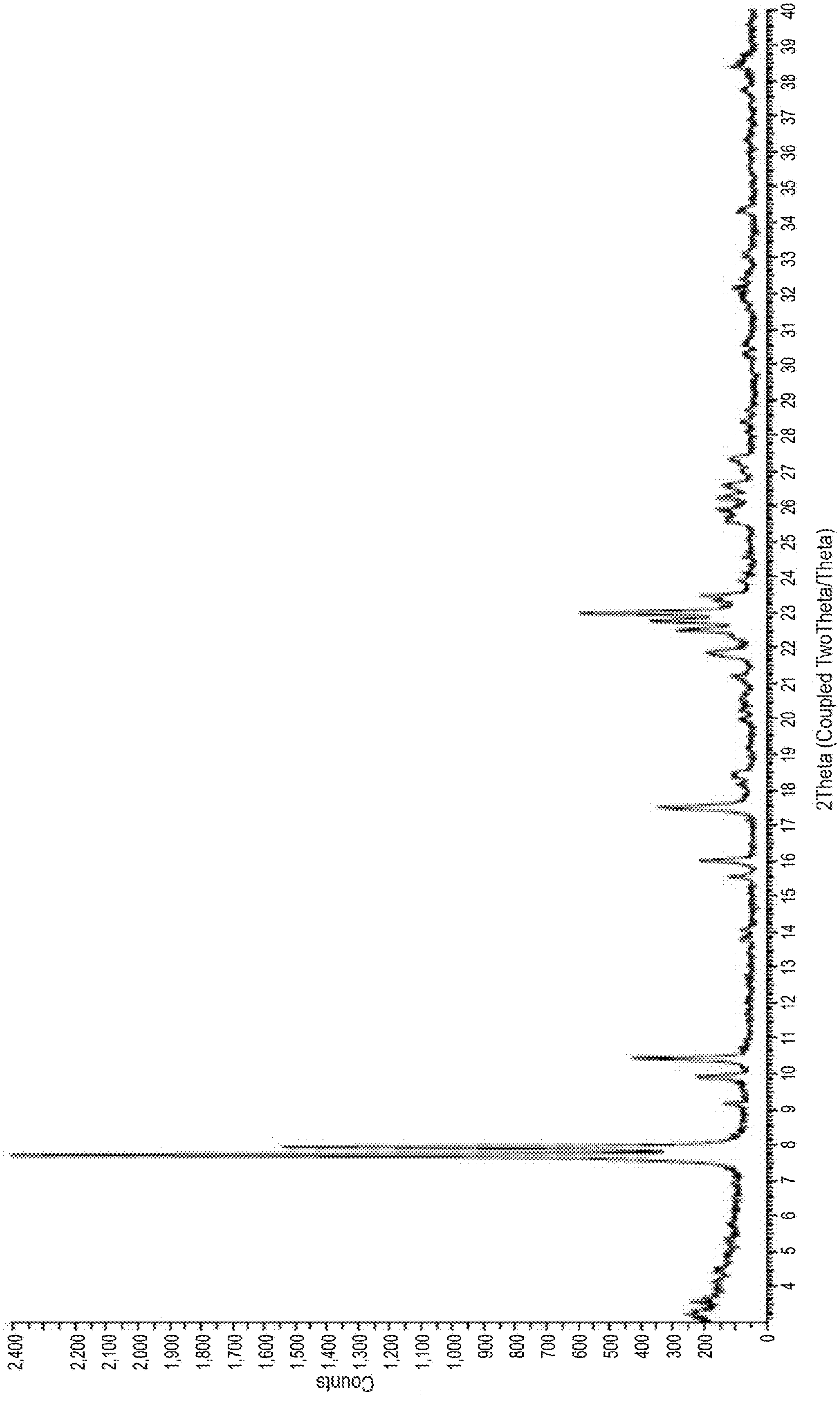
Figure 24B:
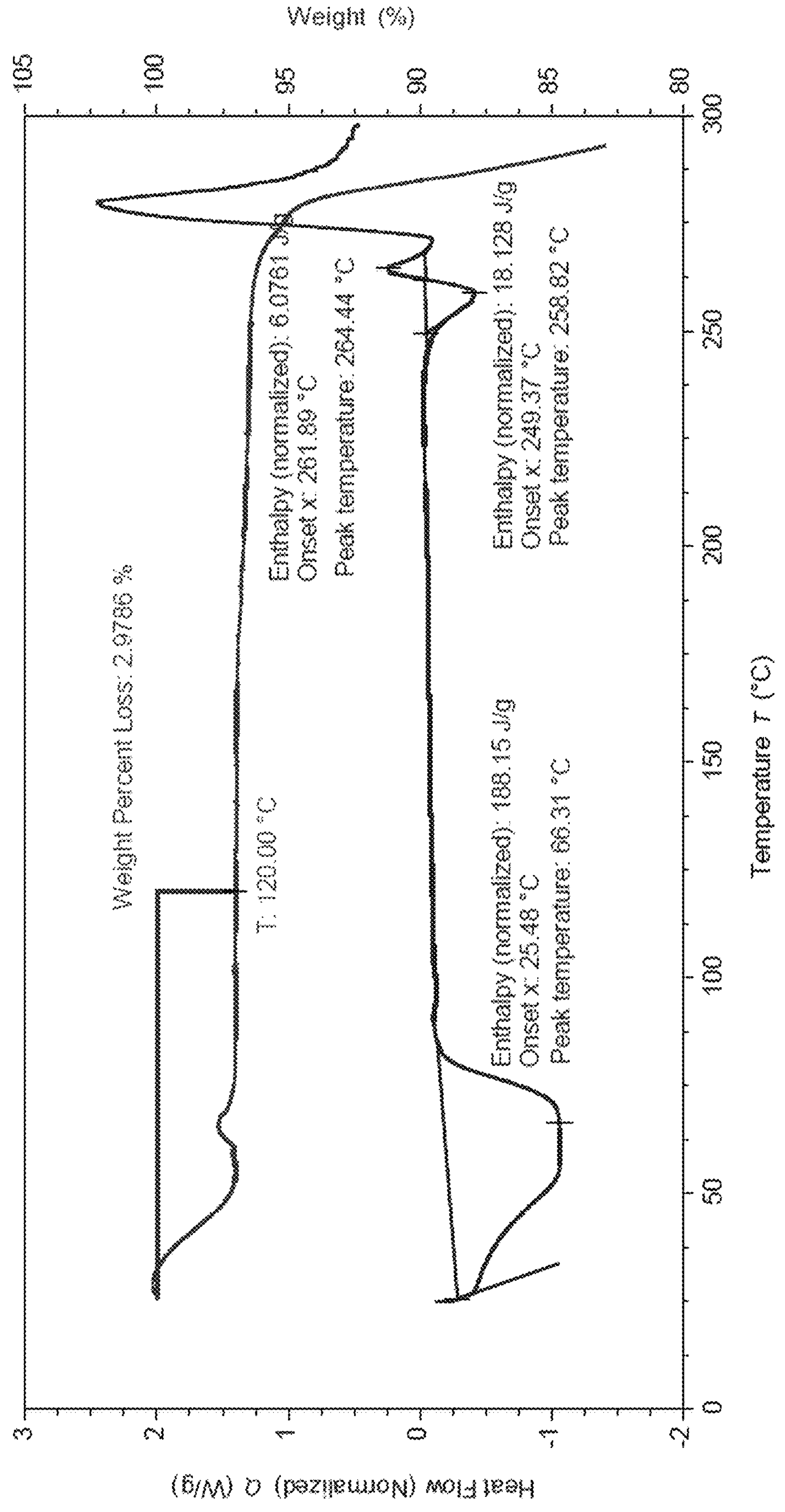

FIG. 24*a* shows a representative X-ray powder diffraction (XRPD) spectrum of crystalline potassium salt Form H of Compound 1. FIG. 24*b* shows a representative thermogravimetric analysis (TGA) and differential scanning calorimetry (DSC) analysis of crystalline potassium salt Form H of Compound 1.

Figure 25A:
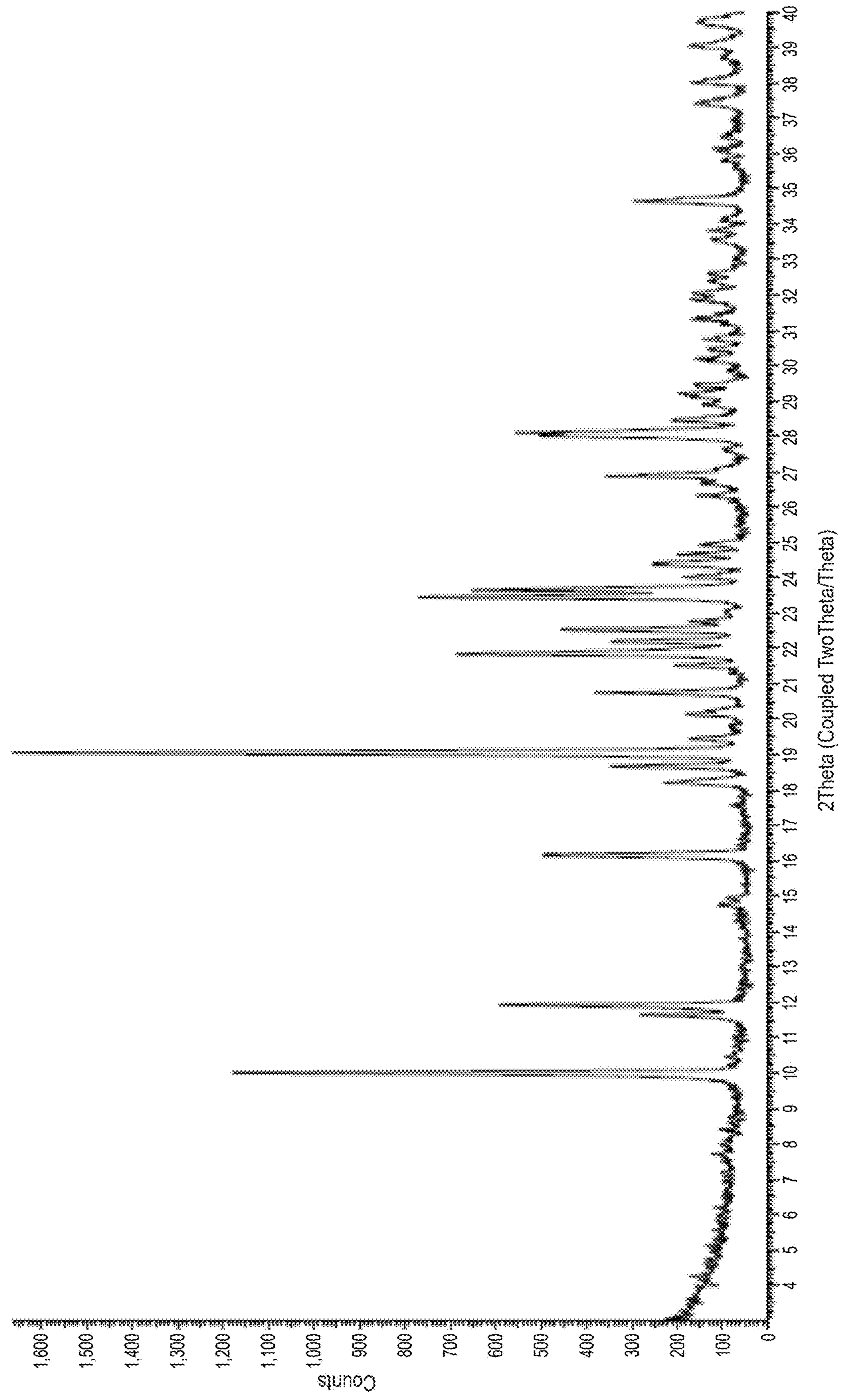
Figure 25B:
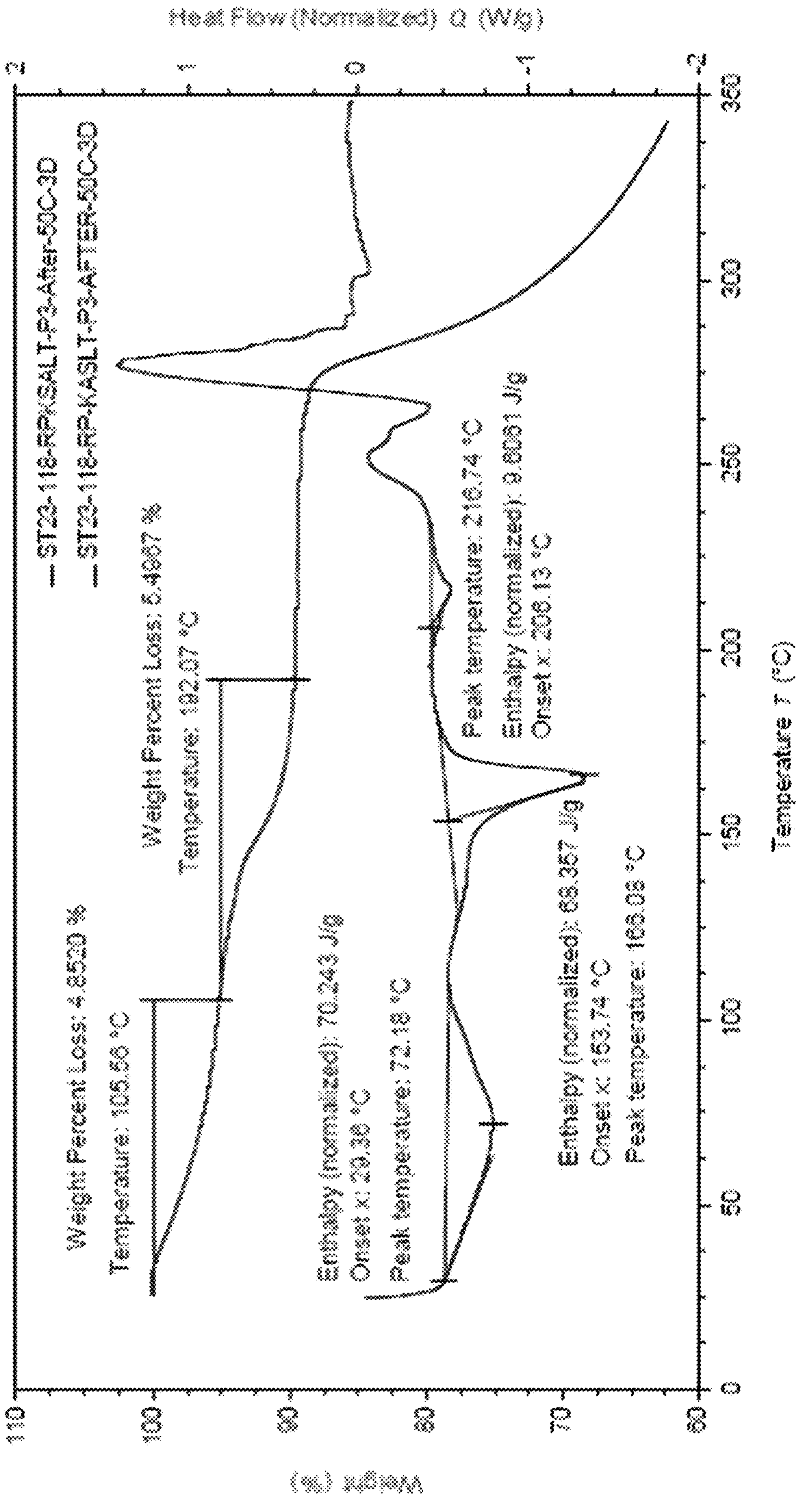

FIG. 25*a* shows a representative X-ray powder diffraction (XRPD) spectrum of crystalline potassium salt Form J of Compound 1. FIG. 25*b* shows a representative thermogravimetric analysis (TGA) and differential scanning calorimetry (DSC) analysis of crystalline potassium salt Form J of Compound 1.

Figure 26A:
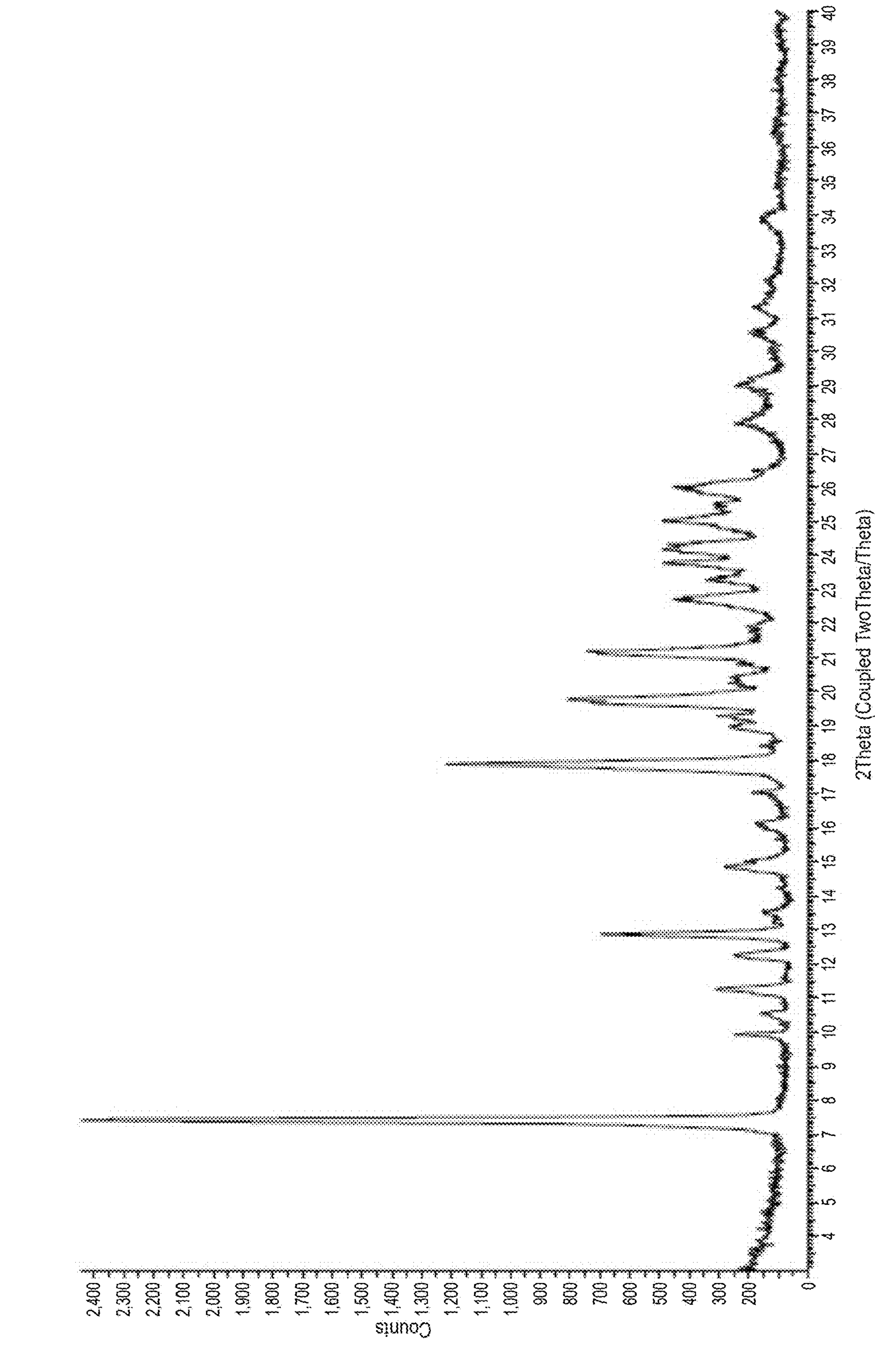
Figure 26B:
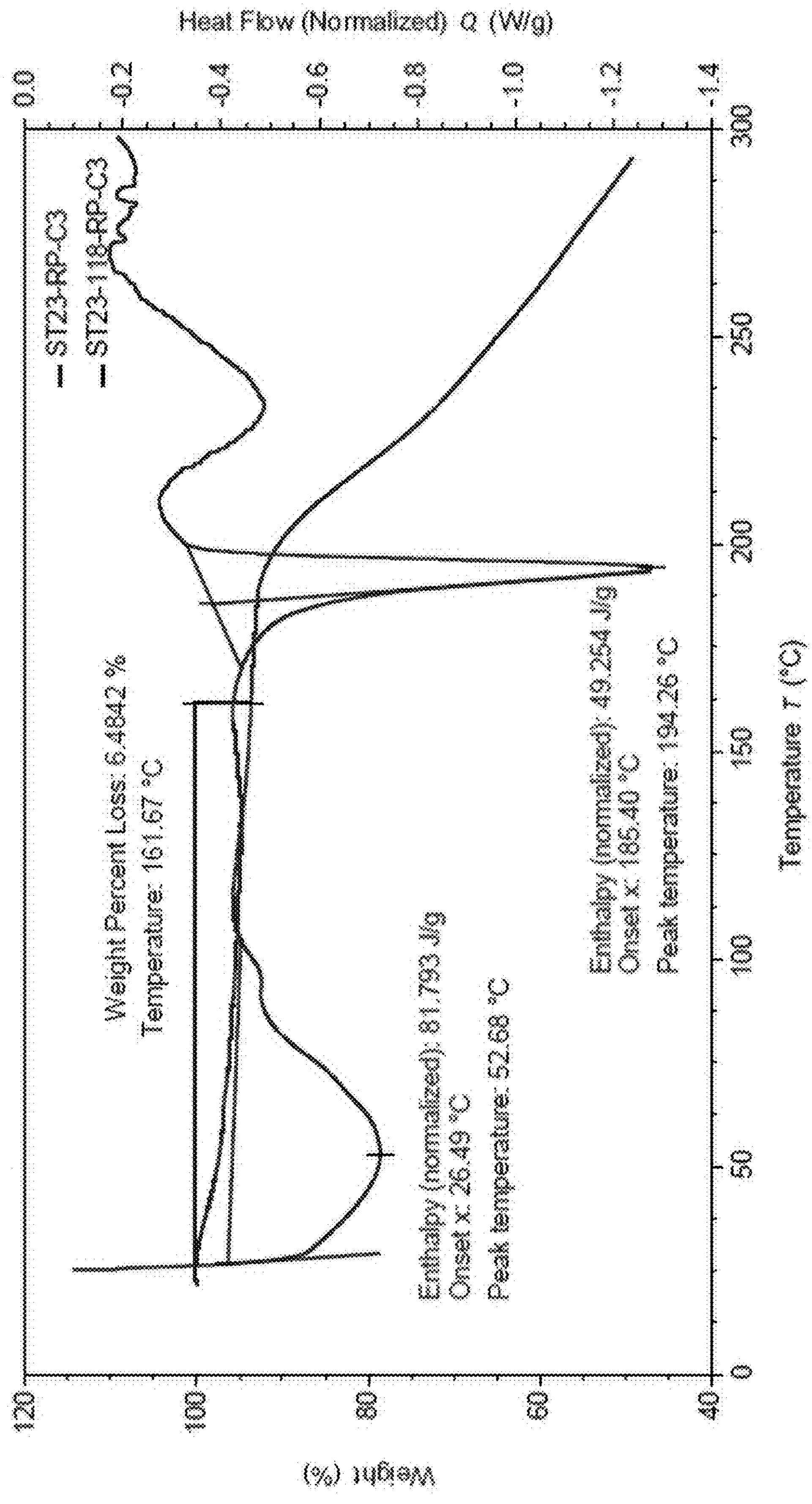
Figure 26C:
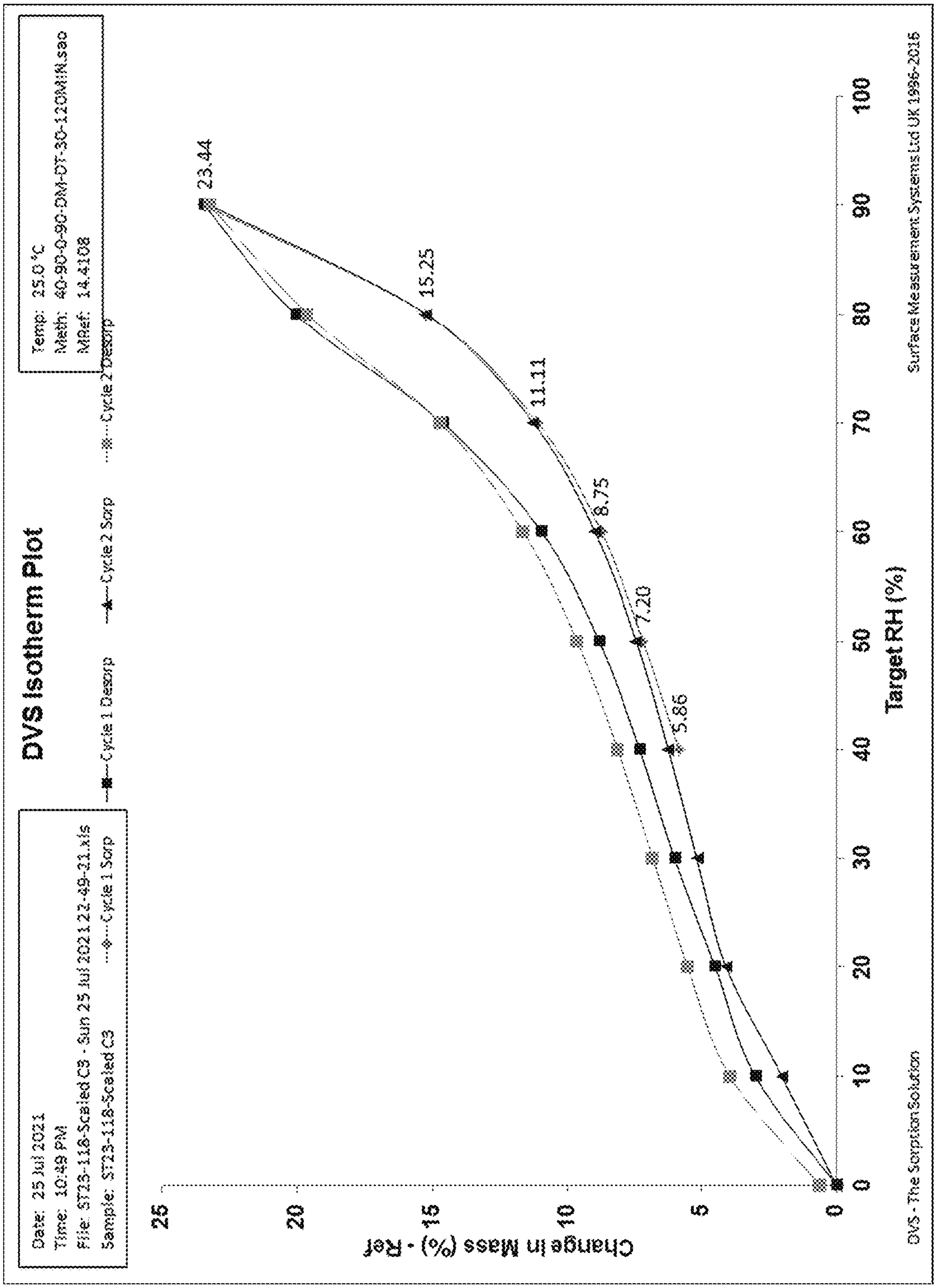

FIG. 26*a* shows a representative X-ray powder diffraction (XRPD) spectrum of crystalline choline salt Form K of Compound 1. FIG. 26*b* shows a representative thermogravimetric analysis (TGA) and differential scanning calorimetry (DSC) analysis of choline salt Form K of Compound 1. FIG. 26*c* presents a representative dynamic vapor sorption (DVS) analysis of crystalline choline salt Form K of Compound 1.

Figure 27A:
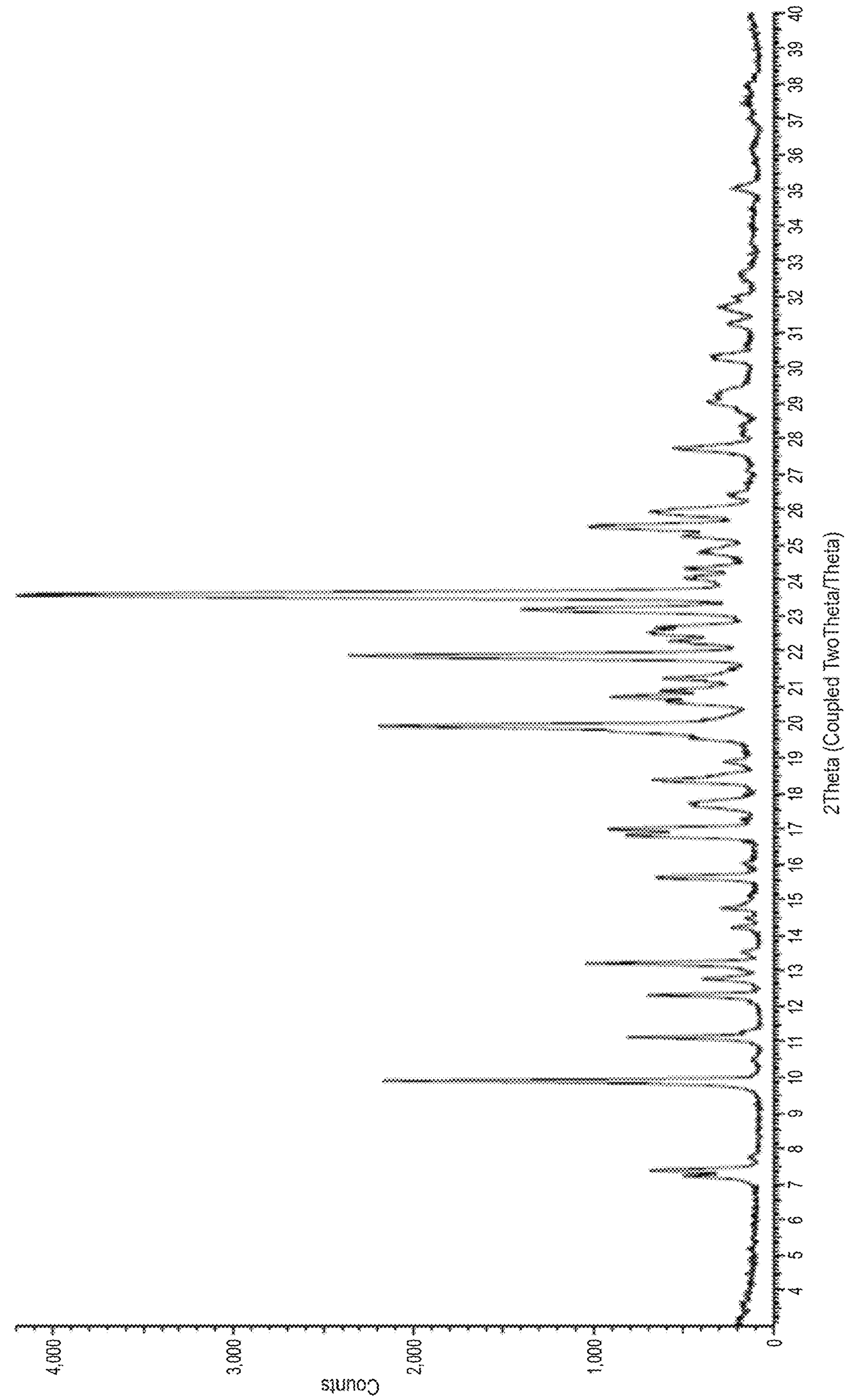
Figure 27B:
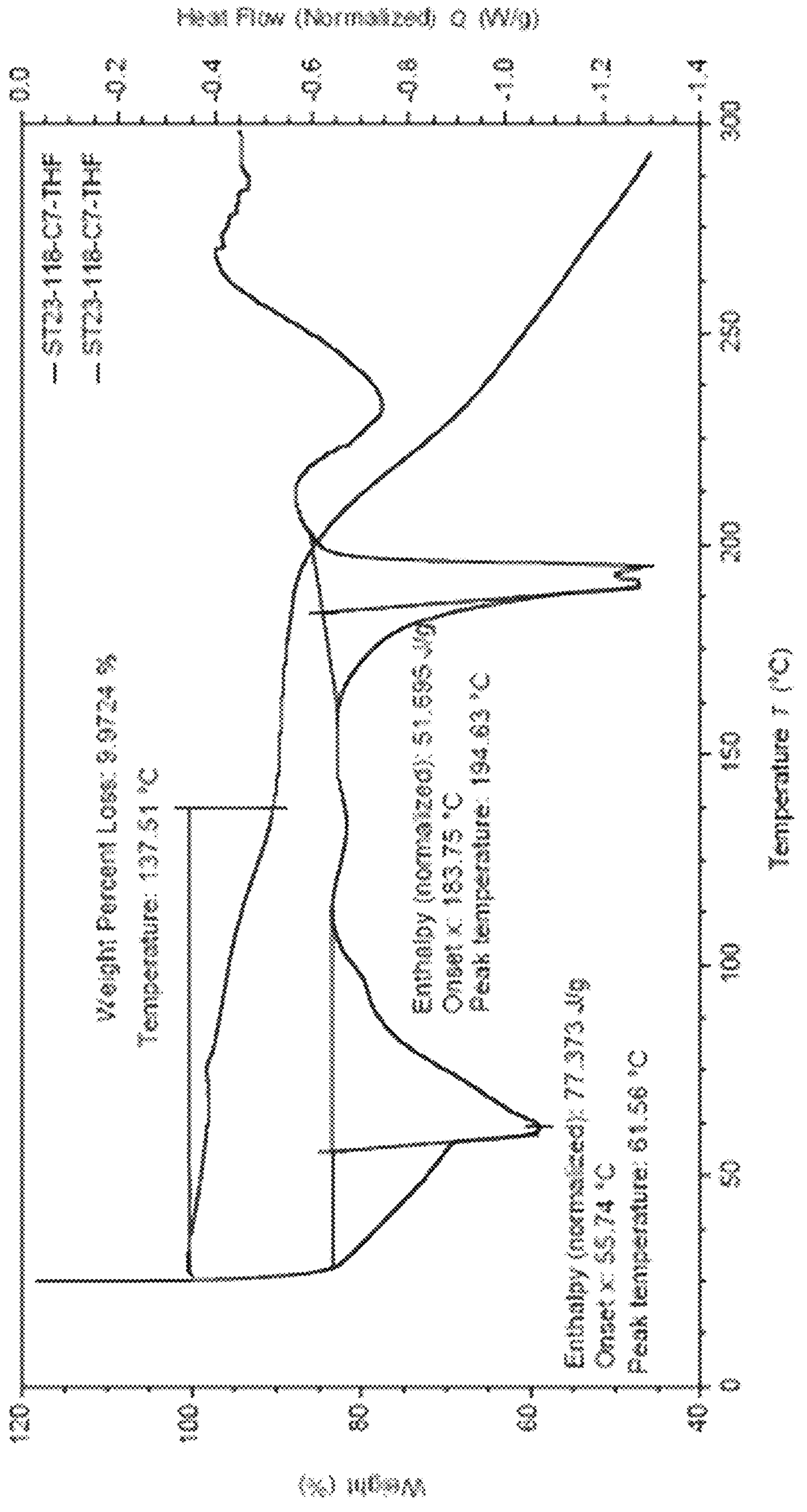
Figure 27C:
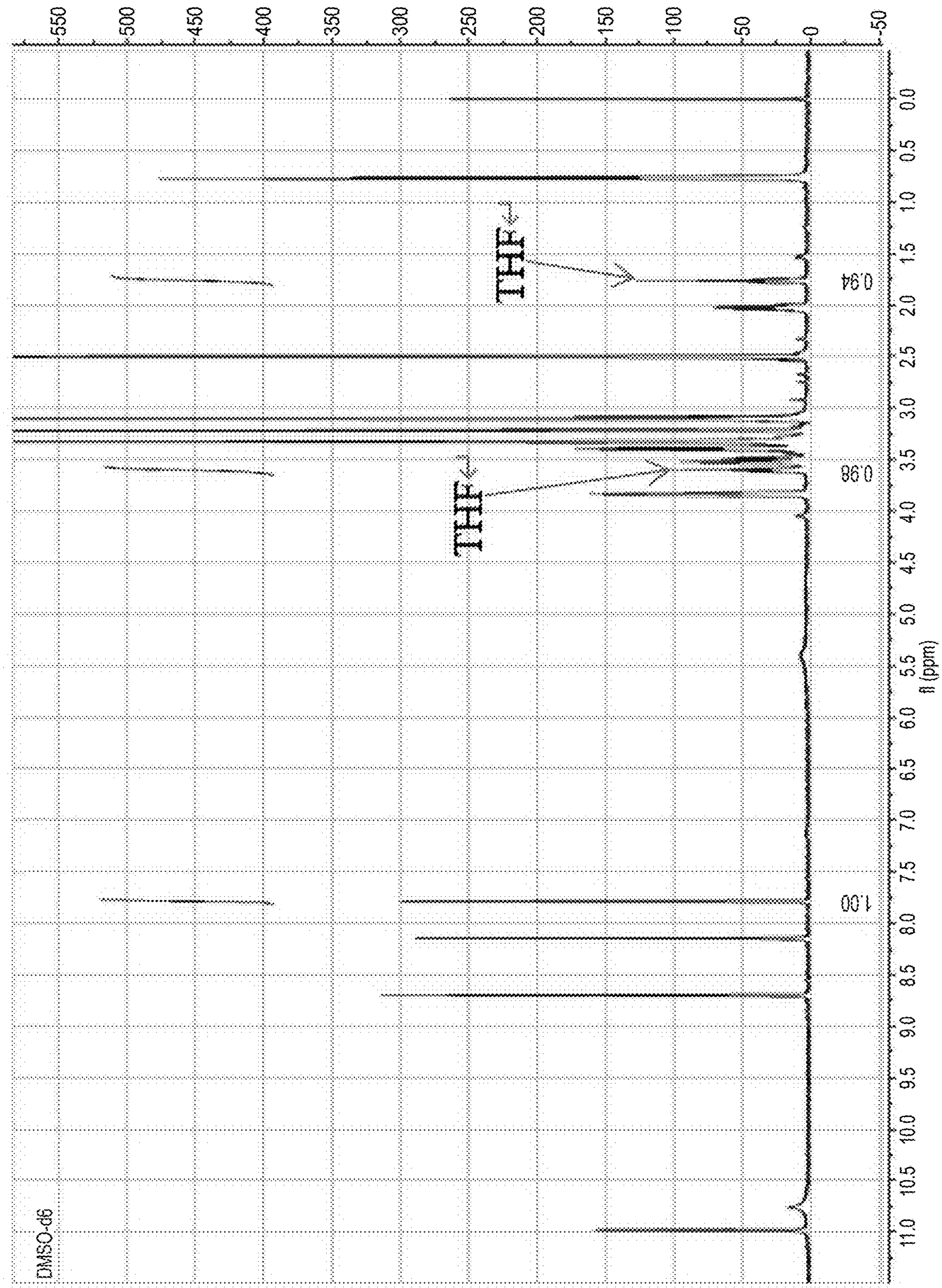

FIG. 27*a* shows a representative X-ray powder diffraction (XRPD) spectrum of crystalline choline salt Form L of Compound 1. FIG. 27*b* shows a representative thermogravimetric analysis (TGA) and differential scanning calorimetry (DSC) analysis of crystalline choline salt Form L of Compound 1. FIG. 27*c* presents a representative $^1$H-NMR spectrum of crystalline choline salt Form L of Compound 1.

DETAILED DESCRIPTION

In various embodiments, the present disclosure is directed to Compound 1 or a pharmaceutically acceptable salt thereof or a hydrate or a solvate of the same, which for example, can be in an isolated form, a substantially pure form, and/or in a solid form. As exemplified in the Examples section, various polymorphic forms of Compound 1 were found. Among these polymorphs, Form III of Compound 1 was found to be stable and can be more suitable for various pharmaceutical uses compared to its other forms. Compound 1 has the following molecular formula:

Compound 1

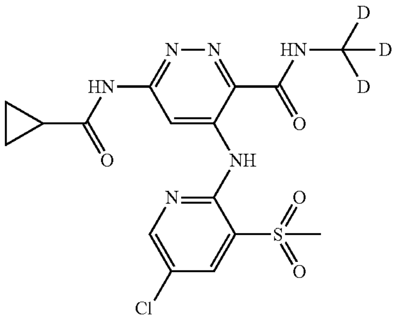 [SMILES: [2H]C([2H])([2H])NC(=O)c1nnc(NC(=O)C2CC2)cc1Nc1ncc(Cl)cc1S(C)(=O)=O]

As described in International Application No. PCT/CN2021/140271, filed on Dec. 22, 2021, the content of which is incorporated herein by reference in its entirety, Compound 1 has, as tested in above application, an HEK blue IL23 $IC_{50}$ value of 2.5 nM, and is advantageous in terms of, for example, human liver microsomal stability, rat pharmacokinetic profiles and selectivity of TYK2 over JAK1, and thus can be useful for treating various diseases or disorders, such as those described herein, e.g., an autoimmune and/or inflammatory disease, such as multiple sclerosis, rheumatoid arthritis, inflammatory bowel disease, systemic lupus erythematosus, psoriasis, psoriatic arthritis, Crohn's Disease, Sjogren's syndrome and/or scleroderma.

Compound 1

In some embodiments, the present disclosure is directed to Compound 1 or a pharmaceutically acceptable salt thereof or a hydrate or a solvate of the same. Compound 1 should be understood as in its free form to distinguish it from a salt formed with an external acid or base. Unless obvious from context, Compound 1 should be understood as in its free form as discussed.

Compound 1 can be synthesized by the method as described in International Application No. PCT/CN2021/140271, filed on Dec. 22, 2021, the content of which is incorporated herein by reference in its entirety. The present disclosure provides a modified method for producing Compound 1, comprising the following steps:

Step 1: Compound 1-1 is reacted with (2,4-dimethoxyphenyl) methaneamine to produce Compound 1-2;

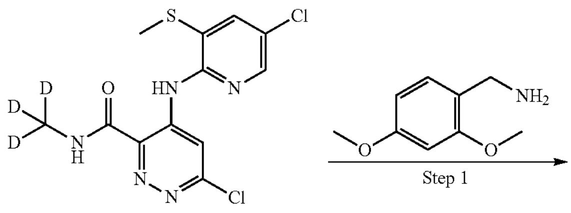

1-1

-continued

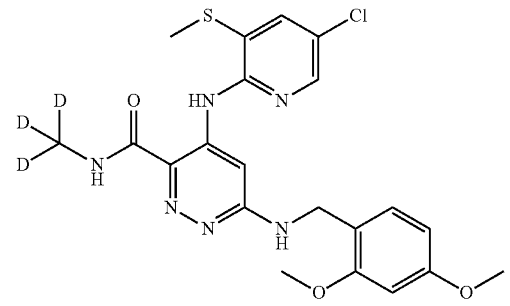

1-2

Step 2: Compound 1-2 is reacted with cyclopropanecarbonyl chloride to produce Compound 1-3;

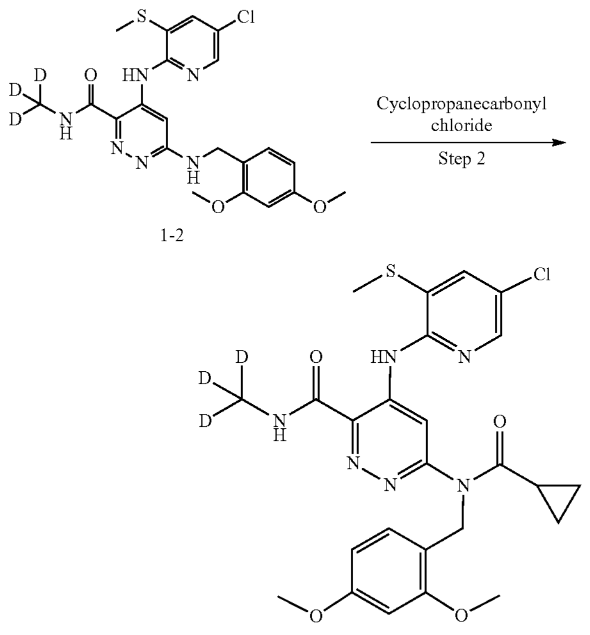

1-2

1-3

Step 3: Compound 1-3 is oxidized to produce Compound 1-4;

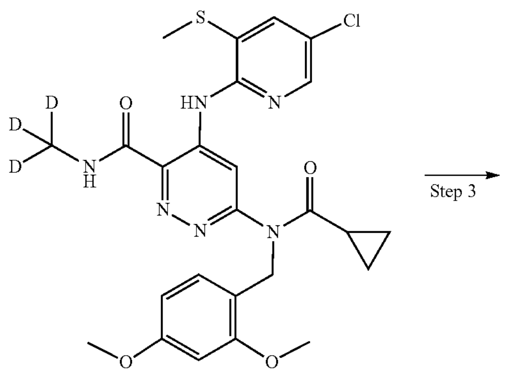

1-3

-continued

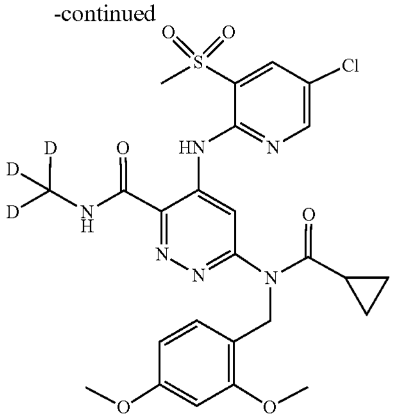

1-4

Step 4: Compound 1-4 is reacted by removing (2,4-dimethoxyphenyl)methylene group to produce Compound 1;

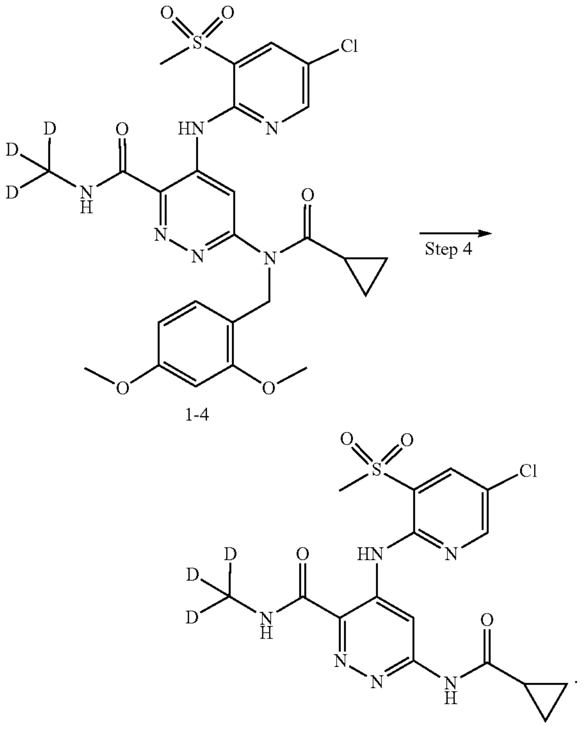

1-4

1

Each step in above synthetic method is easy to be carried out and achieves a high yield, thus leading to a total high yield. The resulting product has a high purity of more than 99%, with few impurities. Accordingly, the new synthetic method is suitable for scale-up production.

In some embodiments, Step 1 can be carried out by using cesium fluoride in N-methylpyrrolidone. In some embodiments, Step 2 can be carried out at a temperature of 50-80° C., preferably 60-70° C., and more preferably at 65° C., In some embodiments, Step 3 can be performed by using potassium peroxymonosulfate as an oxidizing agent. In some embodiments, Step 4 can be performed by using an acid, such as trifluoroacetic acid.

In some embodiments, Compound 1 can be in a solid form, such as an amorphous form, a crystalline form, or a combination thereof. In some embodiments, Compound 1 can be an amorphous form. In some embodiments, Compound 1 can be in a crystalline form (e.g., in any one or more crystalline forms I, II, III, IV, V, VI, VII, VIII, IX, X, XI, XII, XIII, XIV, XV, XVI, or XVII as described herein). As used herein, when Compound 1 is said to exist or be in one particular solid form (e.g., a crystalline form), it should be understood that in some embodiments, the compound can exist predominantly in that particular form. However, in some embodiments, the compound can also exist in the particular form, in a mixture with one or more other solid forms, including amorphous form. For example, when Compound 1 is said to exist or be in Form III, Compound 1 can exist predominantly in Form III, such as more than 80% by weight, more than 90% by weight, or more than 95% by weight of Compound 1 are in Form III, or no other solid form can be identified, for example, by XRPD; or in some embodiments, Compound 1 can exist in Form III, in a mixture with one or more solid forms such as an amorphous form.

Compound 1 herein is typically in a substantially pure form. For example, in some embodiments, Compound 1 can have a purity of greater than 70%, preferably greater than 90% (e.g., greater than 95%, greater than 97%, greater than 98%, greater than 98.5%), by weight, by HPLC area, or both. In some embodiments, the Compound 1 can be characterized by a purity by weight and/or by HPLC area of about 70%, about 75%, about 80%, about 85%, about 90%, about 95%, about 97%, about 99%, or any ranges between the specified values. For example, in some embodiments, the Compound 1 can be characterized by a purity by HPLC area of about 70%, about 75%, about 80%, about 85%, about 90%, about 95%, about 97%, about 99%, or any ranges between the specified values. The substantially pure Compound 1 can be in a solid form (e.g., a crystalline pure or salt form described herein, amorphous form, or a combination thereof) or in a solution, suspension, or another form. In some embodiments, the substantially pure Compound 1 can be in crystalline Form III. For the avoidance of doubt, a composition comprising the substantially pure Compound 1 herein and one or more other ingredients should be understood as a mixture of the substantially pure Compound 1 herein and the one or more other ingredients, for example, such composition can be obtained directly or indirectly from mixing the substantially pure Compound 1 with the one or more other ingredients, such as solvent, pharmaceutically acceptable excipients, etc.

In some embodiments, the Compound 1 is in a crystalline form. In some embodiments, the Compound 1 is in a crystalline Form I, Characteristics of Form I include any of those described herein. In some embodiments, crystalline Form I can be characterized by (1) an X-ray powder diffraction (XRPD) pattern having one or more (e.g., 2, 4, 6, 8, or 10) of the following peaks: 7.5°, 11.7°, 20.9°, 22.3°, 23.6°, 24.8°, 25.3°, 26.5°, 27.0° and 30.2° (2 theta, ±0.2°); (2) an XRPD pattern substantially the same as shown in FIG. 1*a*; (3) a Differential Scanning Calorimetry (DSC) profile substantially the same as shown in FIG. 1*b*; or any combination thereof (e.g., (1) and (3), or (2) and (3)). In some embodiments, the crystalline Form I can be characterized by an XRPD pattern having the characteristic peaks (e.g., peaks with relative intensity of 5% or above, 10% or above, 15% or above, 20% or above, 30% or above, 40% or above, 50% or above, 60% or above, 70% or above, 80% or above, or 90% or above) of FIG. 1*a* or as shown in Table 1 (2 theta, ±0.2°). To be clear, when it is said that the XRPD pattern of Form I has the characteristic peaks of FIG. 1*a* or Table 1 or is substantially the same as FIG. 1*a*, it does not require that the XRPD pattern have the same relative intensities for the corresponding peaks as shown in FIG. 1*a* or Table 1, as applicable. It suffices that the XRPD pattern includes the peaks at the respective diffraction angels (2 theta, ±0.2°) corresponding to the peaks as shown in FIG. 1*a* or Table 1, as applicable, regardless of their relative intensities. Similar expressions as to other crystalline forms herein should be understood similarly.

In some embodiments, the Compound 1 is in a crystalline Form II, characterized by (1) an X-ray powder diffraction (XRPD) pattern having one or more (e.g., 2, 4, 6, 8, or 10) of the following peaks: 7.1°, 7.7°, 11.1°, 12.3°, 20.4°, 21.7°, 22.7°, 24.7°, 26.9° and 27.5° (2 theta, ±0.2°); (2) an XRPD pattern substantially the same as shown in FIG. 2*a*; (3) a Differential Scanning Calorimetry (DSC) pattern substantially the same as shown in FIG. 2*b*; or any combination thereof (e.g., (1) and (3), or (2) and (3)).

In some embodiments, the Compound 1 is in a crystalline Form III, characterized by (1) an X-ray powder diffraction (XRPD) pattern having one or more (e.g., 2, 4, 6, 8, or 10) of the following peaks: 7.0° 9.7°, 14.1°, 14.5°, 17.2°, 18.2°, 19.6°, 21.3°, 24.1°, and 27.0° (2 theta, ±0.2°); (2) an XRPD pattern substantially the same as shown in FIG. 3*a*; (3) a Differential Scanning Calorimetry (DSC) pattern substantially the same as shown in FIG. 3*b*; or any combination thereof (e.g., (1) and (3), or (2) and (3)).

In some embodiments, the crystalline Form III of Compound 1 may be obtained by slurrying the crystalline Form I in acetone, preferably in acetone at 35-75° C. for 1 hour to 2 days. Alternatively, the crystalline Form III of Compound 1 can be obtained by first slurrying Compound 1 in tetrahydrofuran, and then slurrying in ethanol and water. Preferably, the crystalline Form III is obtained by first slurrying in tetrahydrofuran at 55-75° C. for 0.5 to 5 hours, and then in ethanol and water at 60-80° C. for 6 to 48 h.

In some embodiments, the Compound 1 is in a crystalline Form IV, characterized by (1) an X-ray powder diffraction (XRPD) pattern having one or more (e.g., 2, 4, 6, 8, or 9) of the following peaks: 5.6°, 7.6°, 11.3°, 15.2°, 21.0°, 21.7°, 22.8°, 24.0° and 26.8° (2 theta, ±0.2°); (2) an XRPD pattern substantially the same as shown in FIG. 4*a*; (3) a Differential Scanning Calorimetry (DSC) pattern substantially the same as shown in FIG. 4*b*; or any combination thereof (e.g., (1) and (3), or (2) and (3)).

In some embodiments, the Compound 1 is in a crystalline Form V, characterized by (1) an X-ray powder diffraction (XRPD) pattern having one or more (e.g., 2, 4, 6, 8, or 10) of the following peaks: 4.8°, 8.7°, 9.7°, 12.6°, 14.7°, 17.6°, 20.8°, 24.6°, 25.5° and 27.6° (2 theta, ±0.2°); (2) an XRPD pattern substantially the same as shown in FIG. 5*a*; (3) a Differential Scanning Calorimetry (DSC) pattern substantially the same as shown in FIG. 5*b*; or any combination thereof (e.g., (1) and (3), or (2) and (3)).

In some embodiments, the Compound 1 is in a crystalline Form VI, characterized by (1) an X-ray powder diffraction (XRPD) pattern having one or more (e.g., 2, 4, 6, 8, or 10) of the following peaks: 7.2°, 13.3°, 14.5°, 17.8°, 21.9°, 22.2°, 24.6°, 25.0°, 27.1°, and 27.4° (2 theta, ±0.2°); (2) an XRPD pattern substantially the same as shown in FIG. 6*a*; (3) a Differential Scanning Calorimetry (DSC) pattern substantially the same as shown in FIG. 6*b*; or any combination thereof (e.g., (1) and (3), or (2) and (3)).

In some embodiments, the Compound 1 is in a crystalline Form VII, characterized by (1) an X-ray powder diffraction (XRPD) pattern having one or more (e.g., 2, 4, 6, 8, or 10) of the following peaks: 6.1°, 6.6°, 6.9°, 7.5°, 9.4°, 13.9°, 18.7°, 20.9°, 22.7°, and 27.6° (2 theta, 0.2°); (2) an XRPD pattern substantially the same as shown in FIG. 7*a*; (3) a Differential Scanning Calorimetry (DSC) pattern substantially the same as shown in FIG. 7*b*; or any combination thereof (e.g., (1) and (3), or (2) and (3)).

In some embodiments, the Compound 1 is in a crystalline Form VIII, characterized by (1) an X-ray powder diffraction (XRPD) pattern having one or more (e.g., 2, 4, 6, 8, or 10) of the following peaks: 6.7°, 7.4°, 9.4°, 13.6°, 18.7°, 19.0°, 20.8°, 21.9°, 23.6° and 35.7° (2 theta, ±0.20); (2) an XRPD pattern substantially the same as shown in FIG. 8*a*; (3) a Differential Scanning Calorimetry (DSC) pattern substantially the same as shown in FIG. 8*b*; or any combination thereof (e.g., (1) and (3), or (2) and (3)).

In some embodiments, the Compound 1 is in a crystalline Form IX, characterized by (1) an X-ray powder diffraction (XRPD) pattern having one or more (e.g., 2, 4, 6, 7, or 8) of the following peaks: 6.2°, 7.2°, 12.6°, 18.9°, 19.2°, 21.2°, 22.0°, and 23.1° (2 theta, 0.2°); (2) an XRPD pattern substantially the same as shown in FIG. 9*a*; (3) a Differential Scanning Calorimetry (DSC) pattern substantially the same as shown in FIG. 9*b*; or any combination thereof (e.g., (1) and (3), or (2) and (3)).

In some embodiments, the Compound 1 is in a crystalline Form X, characterized by (1) an X-ray powder diffraction (XRPD) pattern having one or more (e.g., 2, 4, 6, 8, or 9) of the following peaks: 7.4°, 7.9°, 9.4°, 11.7°, 20.7°, 22.0°, 22.6°, 23.6° and 26.4° (2 theta, ±0.2°); (2) an XRPD pattern substantially the same as shown in FIG. 10*a*; (3) a Differential Scanning Calorimetry (DSC) pattern substantially the same as shown in FIG. 10*b*; or any combination thereof (e.g., (1) and (3), or (2) and (3)).

In some embodiments, the Compound 1 is in a crystalline Form XI, characterized by (1) an X-ray powder diffraction (XRPD) pattern having one or more (e.g., 2, 4, 6, 8, or 10) of the following peaks: 5.6°, 6.0°, 6.4°, 7.5°, 11.3°, 12.2°, 19.0°, 22.7°, 24.3° and 25.0° (2 theta, ±0.2°); (2) an XRPD pattern substantially the same as shown in FIG. 11*a*; (3) a Differential Scanning Calorimetry (DSC) pattern substantially the same as shown in FIG. 11*b*; or any combination thereof (e.g., (1) and (3), or (2) and (3)).

In some embodiments, the Compound 1 is in a crystalline Form XII, characterized by (1) an X-ray powder diffraction (XRPD) pattern having one or more (e.g., 2, 4, 6, 8, or 10) of the following peaks: 5.9°, 6.4°, 8.7°, 11.0°, 11.9°, 13.5°, 19.3°, 19.5°, 24.0°, and 24.9° (2 theta, 0.2°; (2) an XRPD pattern substantially the same as shown in FIG. 12*a*; (3) a Differential Scanning Calorimetry (DSC) pattern substantially the same as shown in FIG. 12*b*; or any combination thereof (e.g., (1) and (3), or (2) and (3)).

In some embodiments, the Compound 1 is in a crystalline Form XIII, characterized by (1) an X-ray powder diffraction (XRPD) pattern having one or more (e.g., 2, 3, 4, 5, 6 or 7) of the following peaks: 7.4°, 7.8°, 9.7°, 15.6°, 20.8°, 22.2° and 22.6° (2 theta, ±0.2°); (2) an XRPD pattern substantially the same as shown in FIG. 13*a*; (3) a Differential Scanning Calorimetry (DSC) pattern substantially the same as shown in FIG. 13*b*; or any combination thereof (e.g., (1) and (3), or (2) and (3)).

In some embodiments, the Compound 1 is in a crystalline Form XIV, characterized by (1) an X-ray powder diffraction (XRPD) pattern having one or more (e.g., 2, 4, 6, 8, or 10) of the following peaks: 5.5°, 8.6°, 10.3°, 11.1°, 15.6°, 17.5°, 19.8°, 20.8°, 23.1° and 26.4° (2 theta, ±0.2°); (2) an XRPD pattern substantially the same as shown in FIG. 14*a*; (3) a Differential Scanning Calorimetry (DSC) pattern substantially the same as shown in FIG. 14*b*; or any combination thereof (e.g., (1) and (3), or (2) and (3)).

In some embodiments, the Compound 1 is in a crystalline Form XV, characterized by (1) an X-ray powder diffraction (XRPD) pattern having one or more (e.g., 2, 3, 4, 5, or 6) of the following peaks: 7.5°, 7.8°, 93°, 20.5°, 21.5° and 22.4° (2 theta, ±0.2°); (2) an XRPD pattern substantially the same as shown in FIG. 15*a*; (3) a Differential Scanning Calorimetry (DSC) pattern substantially the same as shown in FIG. 15*b*; or any combination thereof (e.g., (1) and (3), or (2) and (3)).

In some embodiments, the Compound 1 is in a crystalline Form XVI, characterized by (1) an X-ray powder diffraction (XRPD) pattern having one or more (e.g., 2, 4, 6, 8, or 10) of the following peaks: 6.9°, 7.2°, 7.9°, 9.4°, 15.9°, 16.7°, 20.4°, 21.1°, 22.5° and 26.0° (2 theta, ±0.2°); (2) an XRPD pattern substantially the same as shown in FIG. 16*a*; (3) a Differential Scanning Calorimetry (DSC) pattern substantially the same as shown in FIG. 16*b*; or any combination thereof (e.g., (1) and (3), or (2) and (3)).

In some embodiments, the Compound 1 is in a crystalline Form XVII, characterized by (1) an X-ray powder diffraction (XRPD) pattern having one or more (e.g., 2, 4, 6, 8, or 10) of the following peaks: 6.1°, 8.8°, 12.0°, 14.7°, 17.7°, 19.1°, 19.5°, 20.9°, 22.7° and 24.3° (2 theta, ±0.2°); (2) an XRPD pattern substantially the same as shown in FIG. 16B-a; (3) a Differential Scanning Calorimetry (DSC) pattern substantially the same as shown in FIG. 16B-b; or any combination thereof (e.g., (1) and (3), or (2) and (3)).

In some embodiments, the Compound 1 is in a crystalline salt form. Representative salts of Compound 1 include, but are not limited to, e.g., water-soluble and water-insoluble salts, such as the acetate, benzenesulfonate, benzoate, bicarbonate, bisulfate, bitartrate, bromide, butyrate, calcium, chloride, choline, citrate, edisylate (camphorsulfonate), fumarate, gluconate, glucuronate, glutamate, hydrobromide, hydrochloride, lauryl sulfate, malate, maleate, mandelate, mesylate, palmitate, pantothenate, phosphate, potassium, propionate, p-toluenesulfonate, salicylate, sodium, stearate, succinate, and sulfate salts.

In some embodiments, the Compound 1 is in a crystalline sulfate Form A, characterized by (1) an X-ray powder diffraction (XRPD) pattern having one or more (e.g., 2, 3, 4, 5, 6, or 7) of the following peaks: 7.2°, 18.9°, 21.2°, 22.0°, 23.0°, 25.3° and 26.7° (2 theta, 0.2°); (2) an XRPD pattern substantially the same as shown in FIG. 17*a*; (3) a Differential Scanning Calorimetry (DSC) pattern substantially the same as shown in FIG. 17*b*; or any combination thereof (e.g., (1) and (3), or (2) and (3)).

In some embodiments, the Compound 1 is in a crystalline sulfate Form B, characterized by (1) an X-ray powder diffraction (XRPD) pattern having one or more (e.g., 2, 4, 6, 8, or 10) of the following peaks: 7.3°, 10.2°, 11.6°, 12.8°, 14.8°, 20.6°, 22.3°, 22.7°, 23.4°, and 25.8° (2 theta, ±0.2°); (2) an XRPD pattern substantially the same as shown in FIG. 18*a*; (3) a Differential Scanning Calorimetry (DSC) pattern substantially the same as shown in FIG. 18*b*; or any combination thereof (e.g., (1) and (3), or (2) and (3)).

In some embodiments, the Compound 1 is in a crystalline sulfate Form C, characterized by (1) an X-ray powder diffraction (XRPD) pattern having one or more (e.g., 2, 4, 6, 8, or 10) of the following peaks: 7.5°, 8.9°, 14.0°, 14.5°, 17.6°, 18.0°, 19.5°, 21.7°, 23.4° and 24.6° (2 theta, ±0.2°); (2) an XRPD pattern substantially the same as shown in FIG. 19*a*; (3) a Differential Scanning Calorimetry (DSC) pattern substantially the same as shown in FIG. 19*b*; or any combination thereof (e.g., (1) and (3), or (2) and (3)).

In some embodiments, the Compound 1 is in a crystalline besylate Form D, characterized by (1) an X-ray powder diffraction (XRPD) pattern having one or more (e.g., 2, 4, 6, 8, or 10) of the following peaks: 6.3°, 6.9°, 7.7°, 8.2°, 9.7°, 12.7°, 13.9°, 143°, 18.6° and 21.2° (2 theta, ±0.2°); (2) an XRPD pattern substantially the same as shown in FIG. 20*a*; (3) a Differential Scanning Calorimetry (DSC) pattern substantially the same as shown in FIG. 20*b*; or any combination thereof (e.g., (1) and (3), or (2) and (3)).

In some embodiments, the Compound 1 is in a crystalline phosphate Form E, characterized by (1) an X-ray powder diffraction (XRPD) pattern having one or more (e.g., 2, 4, 6, 8, or 10) of the following peaks: 7.2°, 9.8°, 11.2°, 12.6°, 14.5°, 18.0°, 19.8°, 21.8°, 22.50, and 25.3° (2 theta, ±0.20); (2) an XRPD pattern substantially the same as shown in FIG. 21*a*; (3) a Differential Scanning Calorimetry (DSC) pattern substantially the same as shown in FIG. 21*b*; or any combination thereof (e.g., (1) and (3), or (2) and (3)).

In some embodiments, the Compound 1 is in a crystalline mesylate Form F, characterized by (1) an X-ray powder diffraction n (XRPD) pattern having one or more (e.g., 2, 4, 6, 7, or 8) of the following peaks: 69°, 7.3°, 8.5°, 13.8°, 17.2°, 22.3°, 22.6° and 27.8° (2 theta, ±0.2°); (2) an XRPD pattern substantially the same as shown in FIG. 22*a*; (3) a Differential Scanning Calorimetry (DSC) pattern substantially the same as shown in FIG. 22*b*; or any combination thereof (e.g., (1) and (3), or (2) and (3)).

In some embodiments, the Compound 1 is in a crystalline mesylate Form G, characterized by (1) an X-ray powder diffraction (XRPD) pattern having one or more (e.g., 2, 4, 6, 8, or 9) of the following peaks: 7.1°, 8.5°, 13.9°, 14.1°, 17.5° 20.6°, 21.4°, 22.2° and 28.7° (2 theta, ±0.2°); (2) an XRPD pattern substantially the same as shown in FIG. 23*a*; (3) a Differential Scanning Calorimetry (DSC) pattern substantially the same as shown in FIG. 23*b*; or any combination thereof (e.g., (1) and (3), or (2) and (3)).

In some embodiments, the Compound 1 is in a crystalline potassium salt Form H, characterized by (1) an X-ray powder diffraction (XRPD) pattern having one or more (e.g., 2, 4, 6, 8, or 10) of the following peaks: 7.7°, 7.9°, 10.4°, 16.0°, 17.5°, 21.9°, 22.5°, 22.8°, 23.0° and 23.4° (2 theta, ±0.20); (2) an XRPD pattern substantially the same as shown in FIG. 24*a*; (3) a Differential Scanning Calorimetry (DSC) pattern substantially the same as shown in FIG. 24*b*; or any combination thereof (e.g., (1) and (3), or (2) and (3)).

In some embodiments, the Compound 1 is in a crystalline potassium salt Form J, characterized by (1) an X-ray powder diffraction (XRPD) pattern having one or more (e.g., 2, 4, 6, 8, or 9) of the following peaks: 10.0°, 11.9°, 16.2°, 19.1°, 20.8°, 21.9°, 22.5°, 23.5° and 26.9° (2 theta, ±0.20); (2) an XRPD pattern substantially the same as shown in FIG. 25*a*; (3) a Differential Scanning Calorimetry (DSC) pattern substantially the same as shown in FIG. 25*b*; or any combination thereof (e.g., (1) and (3), or (2) and (3)).

In some embodiments, the Compound 1 is in a crystalline choline salt Form K, characterized by (1) an X-ray powder diffraction (XRPD) pattern having one or more (e.g., 2, 4, 6, 8, or 10) of the following peaks: 7.4°, 11.3°, 12.9°, 17.9°, 19.8°, 21.2°, 22.7°, 23.8°, 24.2°, 25.0°, and 26.0° (2 theta, ±0.2°); (2) an XRPD pattern substantially the same as shown in FIG. 26*a*; (3) a Differential Scanning Calorimetry (DSC) pattern substantially the same as shown in FIG. 26*b*; or any combination thereof (e.g., (1) and (3), or (2) and (3)).

In some embodiments, the Compound 1 is in a crystalline choline salt Form L, characterized by (1) an X-ray powder diffraction (XRPD) pattern having one or more (e.g., 2, 4, 6, 8, or 10) of the following peaks: 7.2°, 9.9°, 11.1°, 13.2°, 16.8°, 19.9°, 21.9°, 23.2°, 23.6°, and 25.5° (2 theta, ±0.2°); (2) an XRPD pattern substantially the same as shown in FIG. 27*a*; (3) a Differential Scanning Calorimetry (DSC) pattern substantially the same as shown in FIG. 27*b*; or any combination thereof (e.g., (1) and (3), or (2) and (3)).

In some embodiments, the present disclosure also provides a solid form of Compound 1 that can be produced by any of the applicable methods described in the Examples section.

In some embodiments, the present disclosure is also directed to any products produced by any of the methods herein, and methods of using such products.

Pharmaceutical Compositions

In various embodiments, the present disclosure also provides pharmaceutical compositions comprising a compound of the present disclosure, such as Compound 1 in crystalline Form I, II, III, IV, V, VI, VII, VIII, IX, X, XI, XII, XIII, XIV, XV, XVI, or XVII, or in salt Form A, B, C, D, E, F, G, H, J, K, or L described herein, and optionally a pharmaceutically acceptable excipient, Non-limiting suitable excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. See also Remington's The Science and Practice of Pharmacy, 21st Edition, A. R. Gennaro (Lippincott, Williams & Wilkins, Baltimore, Md., 2005; incorporated herein by reference), which discloses various excipients used in formulating pharmaceutical compositions and known techniques for the preparation thereof.

In some embodiments, the present disclosure provides a pharmaceutical composition comprising one or more of the compounds of the present disclosure (e.g., Compound 1 in crystalline Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof), e.g., in a therapeutically effective amount. In any of the embodiments described herein, the pharmaceutical composition can comprise a therapeutically effective amount of a compound selected from Compound 1 in crystalline Form I, I, II, IV, V, VI, VII, VIII, IX, X, XI, XII, XIII, XIV, XV, XVI, or XVII, or in salt Form A, B, C, D, E, F, G, H, J, K, or L.

The pharmaceutical composition can also be formulated for delivery via any of the known routes of delivery, which include but are not limited to oral, parenteral, inhalation, etc.

In some embodiments, the pharmaceutical composition can be formulated for oral administration. The oral formulations can be presented in discrete units, such as capsules, pills, cachets, lozenges, or tablets, each containing a predetermined amount of the active compound; as a powder or granules; as a solution or a suspension in an aqueous or non-aqueous liquid; or as an oil-in-water or water-in-oil emulsion. Excipients for the preparation of compositions for oral administration are known in the art. Non-limiting suitable excipients include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof.

In some embodiments, the pharmaceutical composition is formulated for parenteral administration (such as intravenous injection or infusion, subcutaneous or intramuscular injection). The parenteral formulations can be, for example, an aqueous solution, a suspension, or an emulsion. Excipients for the preparation of parenteral formulations are known in the art. Non-limiting suitable excipients include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof.

In some embodiments, the pharmaceutical composition is formulated for inhalation. The inhalable formulations can be, for example, formulated as a nasal spray, dry powder, or an aerosol administrable through a metered-dose inhaler. Excipients for preparing formulations for inhalation are known in the art. Non-limiting suitable excipients include, for example, lactose, talc, silicic acid, aluminum hydroxide, calcium silicates and polyamide powder, and mixtures of these substances. Sprays can additionally contain propellants, such as chlorofluorohydrocarbons and volatile unsubstituted hydrocarbons, such as butane and propane.

The pharmaceutical composition can include various amounts of the compounds of the present disclosure, depending on various factors such as the intended use and potency and selectivity of the compounds. In some embodiments, the pharmaceutical composition comprises a therapeutically effective amount of a compound of the present disclosure (e.g., Compound 1 in crystalline Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof). In some embodiments, the pharmaceutical composition comprises a therapeutically effective amount of the compound of the present disclosure and a pharmaceutically acceptable excipient. As used herein, a therapeutically effective amount of a compound of the present disclosure is an amount effective to treat a disease or disorder as described herein, such as multiple sclerosis, rheumatoid arthritis, inflammatory bowel disease, systemic lupus erythematosus, psoriasis, psoriatic arthritis, Crohn's Disease, Sjogren's syndrome and/or scleroderma, which can depend on the recipient of the treatment, the disease or disorder being treated and the severity thereof, the composition containing the compound, the time of administration, the route of administration, the duration of treatment, the compound potency, its rate of clearance and whether or not another drug is co-administered.

For veterinary use, a compound of the present disclosure can be administered as a suitably acceptable formulation in accordance with normal veterinary practice. The veterinarian can readily determine the dosing regimen and route of administration that is most appropriate for a particular animal.

In some embodiments, all the necessary components for the treatment of a disease or disorder mediated by IL-12, IL-23 and/or Interferon-alpha (INF-alpha), using a compound of the present disclosure either alone or in combination with another agent or intervention traditionally used for the treatment of such disease can be packaged into a kit, Specifically, in some embodiments, the present invention provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound of the present disclosure, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet, Methods of Treatment Compounds of the present disclosure are useful for treating conditions associated with the modulation of the function of IL-23, IL-12 and/or IFN-alpha. Such conditions include IL-23, IL-12-, and/or or IFN-alpha-associated diseases in which pathogenic mechanisms are mediated by these cytokines, which include any of those known in the art and those described herein.

In some embodiments, the present disclosure provides a method of inhibiting the function of IL-23, IL-12 and/or IFN-alpha in a subject in need thereof, the method comprising administering to the subject an effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof).

In some embodiments, the present disclosure provides a method of treating or preventing a disease or disorder associated with IL-23, IL-12 and/or IFN-alpha in a subject in need thereof, the method comprising administering to the subject an effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof). Suitable diseases or disorders associated with IL-23, IL-12 and/or IFN-alpha that can be treated with the methods herein include any of those known in the art. Exemplary diseases or disorders associated with IL-23, IL-12 and/or IFN-alpha that can be treated with the methods herein also include but not limited to those proliferative, metabolic, allergic, autoimmune and/or inflammatory diseases or disorders described herein.

In some embodiments, the present disclosure provides a method of treating or preventing a proliferative, metabolic, allergic, autoimmune and/or inflammatory disease or disorder, e.g., described herein, in a subject in need thereof, the method comprising administering to the subject an effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof).

In some embodiments, the present disclosure provides a method of treating or preventing an autoimmune and/or inflammatory disease or disorder, e.g., described herein, in a subject in need thereof, the method comprising administering to the subject an effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof).

In some embodiments, the present disclosure provides a method of treating or preventing a metabolic disease or disorder, e.g., described herein, such as type 2 diabetes or atherosclerosis, in a subject in need thereof, the method comprising administering to the subject an effective amount of one or more compounds of the present disclosure (e.g., Compound 1 in Form I, H, III, IV, V, VI, VII, VIII, IX, X, XI, XII, XIII, XIV, XV, XVI, or XVII, or in salt Form A, B, C, D, E, F, G, H, J, K, or L, or in any combination thereof).

In some embodiments, the present disclosure provides a method of treating or preventing cancer in a subject in need thereof, the method comprising administering to the subject an effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof).

In some embodiments, the present disclosure provides a method of treating or preventing a disease or disorder in a subject in need thereof, the method comprising administering to the subject an effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof), wherein the disease or disorder can be one or more diseases or disorders selected from: inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, cutaneous lupus, lupus nephritis, discoid lupus erythematosus, psoriasis; auto-inflammatory diseases including CAPS, TRAPS, FMF, adult onset still's disease (AOSD), systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

In some embodiments, the present disclosure provides a method of treating or preventing a disease or disorder in a subject in need thereof, the method comprising administering to the subject an effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof), wherein the disease or disorder that may be treated with the method include, without limitation, pancreatitis (acute or chronic), asthma, allergies, adult respiratory distress syndrome, chronic obstructive pulmonary disease, glomerulonephritis, rheumatoid arthritis, systemic lupus erythematosis, cutaneous lupus, lupus nephritis, discoid lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic b-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoper oxidase syndase-2, and pemphigus vulgaris.

In some preferred embodiments, the present disclosure provides a method of treating or preventing a disease or disorder in a subject in need thereof, the method comprising administering to the subject an effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof), wherein the disease or disorder is one or more diseases or disorders selected from Crohn's disease, ulcerative colitis, allograft rejection, rheumatoid arthritis, psoriasis, ankylosing spondylitis, psoriatic arthritis, and pemphigus vulgaris.

In some preferred embodiments, the present disclosure provides a method of treating or preventing a disease or disorder in a subject in need thereof, the method comprising administering to the subject an effective amount of one or more compounds of the present disclosure (e.g., Compound 1 in Form I, II, II, IV, V, VI, VII, VIII, IX, X, XI, XII, XIII, XIV, XV, XVI, or XVII, or in salt Form A, B, C, D, E, F, G, H, J, K, or L, or in any combination thereof), wherein the disease or disorder is ischemia reperfusion injury, including cerebral ischemia reperfusions injure) arising from stroke and cardiac ischemia reperfusion injury arising from myocardial infarction.

In some preferred embodiments, the present disclosure provides a method of treating or preventing multiple myeloma in a subject in need thereof, the method comprising administering to the subject an effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof).

In some preferred embodiments, the present disclosure provides a method of treating or preventing a disease or disorder in a subject in need thereof, the method comprising administering to the subject an effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof), wherein the disease or disorder is one or more disease or disorder selected from multiple sclerosis, rheumatoid arthritis, inflammatory bowel disease, systemic lupus erythematosus, psoriasis, psoriatic arthritis, Crohn's Disease, Sjogren's syndrome and scleroderma.

In some preferred embodiments, the present disclosure provides a method of treating multiple sclerosis in a subject in need thereof, the method comprising administering to the subject a therapeutically effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof).

In some preferred embodiments, the present disclosure provides a method of treating rheumatoid arthritis in a subject in need thereof, the method comprising administering to the subject a therapeutically effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof).

In some preferred embodiments, the present disclosure provides a method of treating inflammatory bowel disease in a subject in need thereof, the method comprising administering to the subject a therapeutically effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof).

In some preferred embodiments, the present disclosure provides a method of treating systemic lupus erythematosus in a subject in need thereof, the method comprising administering to the subject a therapeutically effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof).

In some preferred embodiments, the present disclosure provides a method of treating psoriasis in a subject in need thereof, the method comprising administering to the subject a therapeutically effective amount of one or more compounds of the present disclosure (e.g., Compound 1 in Form I, II, II, IV, V, VI, VII, VIII, IX, X, XI, XII, XIII, XIV, XV, XVI, or XVII, or in salt Form A, B, C, D, E, F, G, H, J, K, or L, or in any combination thereof).

In some preferred embodiments, the present disclosure provides a method of treating psoriatic arthritis in a subject in need thereof, the method comprising administering to the subject a therapeutically effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof).

In some preferred embodiments, the present disclosure provides a method of treating Crohn's Disease in a subject in need thereof, the method comprising administering to the subject a therapeutically effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof).

In some preferred embodiments, the present disclosure provides a method of treating Sjogren's syndrome in a subject in need thereof, the method comprising administering to the subject a therapeutically effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof).

In some preferred embodiments, the present disclosure provides a method of treating scleroderma in a subject in need thereof, the method comprising administering to the subject a therapeutically effective amount of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof).

In some embodiments, the present disclosure also provides a use of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof) for the treatment or prevention of any of the diseases or disorders described herein, such as multiple sclerosis, rheumatoid arthritis, inflammatory bowel disease, systemic lupus erythematosus, psoriasis, psoriatic arthritis, Crohn's Disease, Sjogren's syndrome and/or scleroderma.

In some embodiments, the present disclosure also provides a use of one or more compounds of the present disclosure (e.g., Compound 1 in Form I, II, III, IV, V, VI, VII, VIII, IX, X, XI, XII, XIII, XIV, XV, XVI, or XVII, or in salt Form A, B, C, D, E, F, G, H, J, K, or L, or in any combination thereof) in the manufacture of a medicament for the treatment or prevention of any of the diseases or disorders described herein, such as multiple sclerosis, rheumatoid arthritis, inflammatory bowel disease, systemic lupus erythematosus, psoriasis, psoriatic arthritis, Crohn's Disease, Sjogren's syndrome and/or scleroderma.

Compounds of the present disclosure can be used as a monotherapy or in a combination therapy. In some embodiments, the methods of treating IL-23-, IL-12 and/or IFNα-associated diseases or disorders can comprise administering compounds of the present disclosure alone or in combination with each other and/or other suitable therapeutic agents useful in treating such conditions, Exemplary of such other suitable therapeutic agents include corticosteroids, rolipram, calphostin, cytokine-suppressive anti-inflammatory drugs (CSAIDs), interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The administering herein is not limited to any particular route of administration. For example, in some embodiments, the administering can be orally, nasally, transdermally, pulmonary, inhalationally, buccally, sublingually, intraperitoneally, subcutaneously, intramuscularly, intravenously, rectally, intrapleurally, intrathecally and parenterally. In some embodiments, the administering is orally.

Dosing regimen including doses can vary and can be adjusted, which can depend on the recipient of the treatment, the disease or disorder being treated and the severity thereof, the composition containing the compound, the time of administration, the route of administration, the duration of treatment, the compound potency, its rate of clearance and whether or not another drug is co-administered.

Definitions

"Compound(s) of the present disclosure" as used herein refers to Compound 1 or a pharmaceutically acceptable salt thereof or a hydrate or a solvate of the same, an isolated form thereof, a substantially pure form thereof, a solid form thereof including crystalline forms, amorphous forms, hydrates and/or solvates.

As used herein, the term "about" modifying an amount related to the invention refers to variation in the numerical quantity that can occur, for example, through routine testing and handling; through inadvertent error in such testing and handling; through differences in the manufacture, source, or purity of ingredients employed in the invention; and the like. As used herein, "about" a specific value also includes the specific value, for example, about 10% includes 10%. Whether or not modified by the term "about", the claims include equivalents of the recited quantities. In one embodiment, the term "about" means within 20% of the reported numerical value.

As used herein, the terms "treat", "treating", "treatment" and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat", "treating", "treatment" and the like may include "prophylactic treatment" which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the present disclosure to a subject in need of such treatment.

The term "therapeutically effective amount" as used herein, refers to that amount of a therapeutic agent (e.g., any one or more of the Compounds of the present disclosure) sufficient to result in amelioration of one or more symptoms of a disorder or condition (e.g., those proliferative, metabolic, allergic, autoimmune and/or inflammatory diseases or disorders described herein), or prevent appearance or advancement of a disorder or condition, or cause regression of or cure from the disorder or condition.

The term "subject" (alternatively referred to herein as "patient") as used herein, refers to an animal, preferably a mammal, most preferably a human, who has been the object of treatment, observation or experiment. In any of the embodiments described herein, the subject can be a human.

EXAMPLES

General Methods

Materials: the starting materials, reagents, solvents, etc. are generally available through commercial sources.

$^1$H-Nuclear Magnetic Resonance spectroscopy ($^1$H NMR): $^1$H NMR was performed using Bruker Advance 400 equipped with automated sampler (B-ACS 120).

Power X-ray Diffraction (XRPD) Analysis: The solid samples were examined using X-ray diffractometer (Bruker D8 advance). The system is equipped with LynxEye detector. The X-ray wavelength is 1.5418 Å. The samples were scanned from 3 to 400 (2θ), at a step size 0.020 (2θ). The tube voltage and current were 40 KV and 40 mA, respectively.

Thermo Gravimetric Analysis (TGA): TGA was carried out on a Discovery TGA 55 (TA Instruments, US). The sample was placed into an open tared aluminum pan, automatically weighed, and inserted into the TGA furnace. The sample was heated at a rate of 10° C./min from room temperature (RT) to the final temperature.

Differential Scanning Calorimeter (DSC): DSC was performed using a Discovery DSC 250 (TA Instruments, US). The sample was placed into an aluminum pin-hole hermetic pan and the weight was accurately recorded. The sample was heated at a rate of 10° C./min from 25° C. to the final temperature.

Dynamic Vapor Sorption (DVS) Analysis: Moisture sorption/desorption data was collected on a DVS Intrinsic PLUS (SMS, UK). The sample was placed into a tared sample chamber and automatically weighed. The sample was dried at 40° C. until the dm/dt was less than 0.002% and cooled to 25° C.

High Performance Liquid Chromatography (HPLC): a representative HPLC method is shown below, which can be used, for example, to analyze the purity, solubility, and stability of Compound 1 herein.

| | |
|---|---|
| Instrument | Agilent 1260 series |
| Column | Agilent Zorbax SB C18, 150*4.6 mm, 3.5 μm |
| Column temperature | 30° C. |
| Mobile phase | A: 0.05% TFA in water<br>B: 0.05% TFA in ACN |
| Gradient condition (% of B) | 0 min: 5%<br>13 min: 95%<br>15 min: 95%<br>15.1 min: 5%<br>20 min: 5% |
| Flow rate | 1.0 mL/min |
| Injection volume | 10 μL |
| UV wavelength | 260 nm |
| Run time | 20 min |
| Diluent | ACN:DMSO (v:v = 9:1) |

Preparation and Solid State Characterization of Compound 1

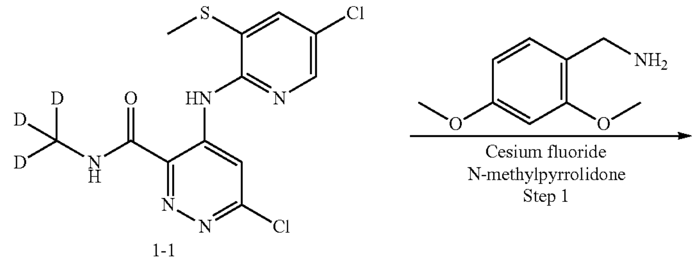

1-1

-continued

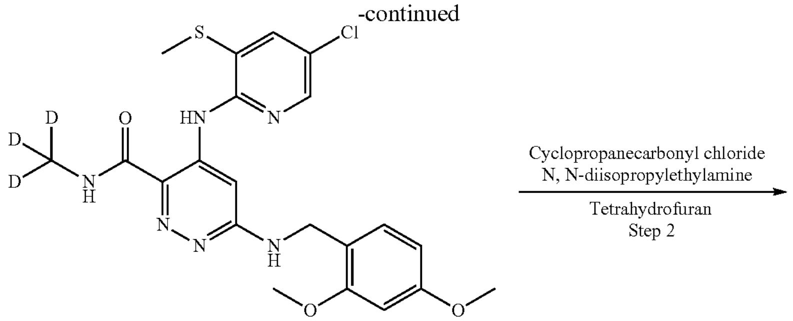

1-2

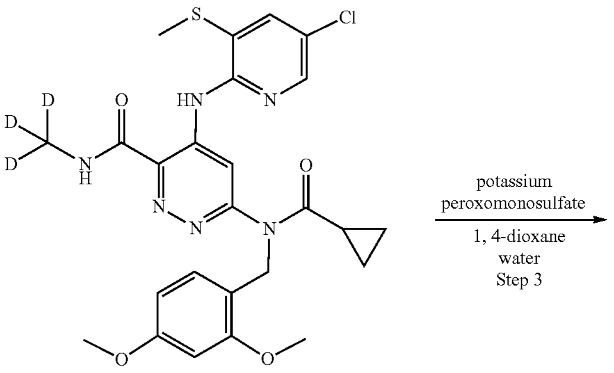

1-3

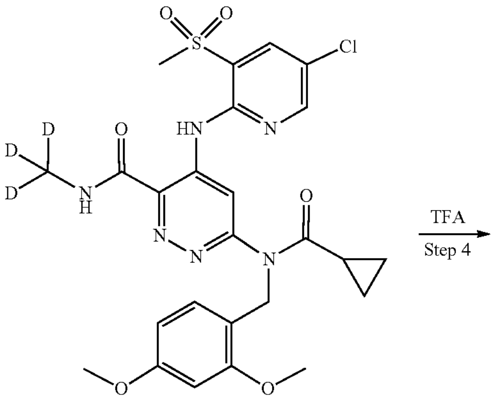

1-4

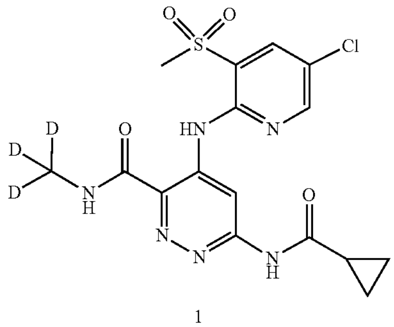

1

Compound 1-1 was prepared from 2-amino-5-chloropyridine over several steps by following the known procedure described in International Application No. PCT/CN2021/140271, filed on Dec. 22, 2021, the content of which is incorporated herein by reference in its entirety.

Step 1: Under nitrogen, Compound 1-1 (200 g), (2,4-dimethoxyphenyl) methaneamine (290 g) and cesium fluoride (88 g) were added to N-methylpyrrolidone (1000 mL) to react at 120° C. for 3 hours. The reaction mixture was then cooled to RT, quenched with water and filtered. The filter cake was rinsed with water and collected. At a temperature of 65° C., the crude product was slurried with a mixed solvent of tetrahydrofuran and isopropanol (V/V, 1/1) to give Compound 1-2 (a white solid, 251 g with a yield of 91%). LCMS: 478.1 $[M+1]^+$.

Step 2: Under nitrogen, Compound 1-2 (200 g) and N, N-diisopropylethylamine (81 g) were added to tetrahydrofuran (1200 mL), and heated to 65° C. A solution of cyclopropanecarbonyl chloride (52.6 g) in THF (500 mL) was added dropwise to react for 2 hours. The reaction mixture was cooled to 25° C., quenched with water, and extracted with dichloromethane. The organic phase is washed with water, concentrated under reduced pressure, and slurried by adding isopropanol at 80° C. for 1 hour to give Compound 1-3 (a pale yellow solid, 196 g with a yield of 87%). LCMS: 546.2 $[M+1]^+$; H NMR: (400 MHz, $CDCl_3$); δ: 12.20 (s, 1H), 9.08 (s, 1H), 8.45 (s, 1H), 8.06, (d, 1H, J=4.0 Hz), 7.62 (d, 1H, J=4.0 Hz), 7.27 (d, 1H, J=12.0 Hz), 6.43 (dd, 1H, J=4.0, 12.0 Hz), 6.36 (d, 1H, J=4.0 Hz), 5.24 (s, 2H), 3.77 (s, 3H), 3.62 (s, 3H), 2.55 (s, 3H), 1.80-1.71 (m, 1H), 1.20-1.16 (m, 2H), 0.84-0.78 (m, 2H).

Step 3: Under nitrogen, Compound 1-3 (160 g) was added to 1,4-dioxane (1600 mL). At a temperature below 30° C., a solution of potassium peroxymonosulfate (325 g) in water (700 mL) was added to react at 30° C. for 24 hours. The reaction mixture was filtered and washed with dichloromethane. The filtrate was washed with 5% sodium sulfite aqueous solution and water, respectively, After the organic phase is concentrated, methanol is added to slurry at 65° C. for 1 hour to give Compound 1-4 (a white solid, 121 g with a yield of 72%). $^1H$ NMR: (400 MHz, DMSO-$d_6$); δ: 12.25 (s, 1H), 9.45 (s, 1H), 8.75 (d, 1H, J=4.8 Hz), 8.58, (d, 1H, J=2.4 Hz), 8.25 (d, 1H, J=2.4 Hz), 7.10 (d, 1H, J=8.0 Hz), 6.48-6.44 (m, 2H), 5.04 (s, 2H), 3.72 (s, 3H), 3.60 (s, 3H), 3.41 (s, 3H), 1.80-1.74 (m, 1H), 0.96-0.91 (m, 2H), 0.81-0.76 (m, 2H).

Step 4: Under nitrogen, Compound 12 (105 g) was added to trifluoroacetic acid (TFA, 330 mL) to react at 35° C. for 6 hours. The reaction mixture was cooled to RT and filtered. The filtrate was added to absolute ethanol, stirred for 30 minutes, and then filtered. The filter cake was first slurried in tetrahydrofuran at 65° C. for 1 h and then slurried in ethanol and water at 70° C. for 12 h to give Compound 1 (a white solid, 67 g with a yield of 86%). LCMS: 428.2 [M+1]t $^1H$ NMR: (400 MHz, DMSO-$d_6$); δ: 12.14 (s, 1H), 11.44 (s, 1H), 9.36 (s, 1H), 9.19, (s, 1H), 8.65 (d, 1H, J=2.4 Hz), 8.23 (d, 1H, J=2.4 Hz), 3.38 (s, 3H), 2.12-2.09 (m, 1H), 0.86-0.84 (m, 4H).

Example 1. Preparation and Characterization of Crystalline Form I of Compound 1

33 g of Compound 1 was added to 900 mL of DMSO, heated to 110° C. to dissolve it, cooled to 80-90° C., and filtered directly. 1500 mL of pure water was added to the filtrate while stirring for another 1 hour. The mixture was filtered, and filter cake was rinsed with 500 mL of pure water. The filter cake was added to 1000 mL of pure water, heated to 60-70° C., stirred for 1 hour, cooled to 40-50° C. and filtered. New filter cake was rinsed with 500 mL of pure water, collected, and dried at 60° C. for 30 h.

The resulting solids were characterized by means of XRPD, DSC, and TGA, with XRPD spectrum shown in FIG. 1*a*, and its main diffraction peaks and their relative intensities shown in Table 1. DSC and TGA profiles are shown in FIG. 1*b*. The DSC profile shows a small exothermic peak at 250° C. and a strong endothermic peak at 319° C. The TGA profile shows that there is no apparent weight loss in crystalline Form I at a temperature range from RT to 220° C.

TABLE 1

XRPD peak table for Form I of Compound 1.

| 2θ (°) | Rel. intensity (%) |
|---|---|
| 7.5 | 100.0 |
| 11.3 | 2.3 |
| 11.7 | 10.9 |
| 13.7 | 0.7 |
| 14.9 | 4.4 |
| 15.3 | 3.4 |
| 18.1 | 4.4 |
| 18.9 | 4.5 |
| 20.3 | 2.0 |
| 20.9 | 35.5 |
| 21.4 | 2.7 |
| 22.3 | 18.4 |
| 22.8 | 4.6 |
| 23.6 | 16.0 |
| 24.8 | 15.2 |
| 25.3 | 9.7 |
| 26.5 | 21.4 |
| 27.0 | 5.1 |
| 27.8 | 2.0 |
| 28.9 | 1.7 |
| 30.2 | 5.5 |
| 31.0 | 3.0 |
| 32.8 | 1.6 |
| 35.0 | 2.6 |
| 36.7 | 2.2 |

Example 2. Preparation and Characterization of Crystalline Form II of Compound 1

Crystalline Form I was weighed into a sample vial, and 50 V of isopropanol was then added to slurry at 50° C. for 1 day. Solids were filtered, collected and dried at 50° C. overnight.

The resulting solids were characterized by means of XRPD, DSC, and TGA, with XRPD spectrum shown in FIG. 2*a*, and its main diffraction peaks and their relative intensities shown in Table 2. DSC and TGA profiles are shown in FIG. 2*b*. The DSC profile shows relatively strong endothermic peaks at 310° C. and 317° C., The TGA profile shows that there is no apparent weight loss in crystalline Form II at a temperature range from RT to 275° C.

TABLE 2

XRPD peak table for Form II of Compound 1.

| 2θ (°) | Rel. intensity (%) |
|---|---|
| 6.3 | 2.1 |
| 7.1 | 100.0 |
| 7.7 | 48.9 |
| 11.1 | 7.1 |
| 12.3 | 15.4 |
| 14.4 | 4.0 |
| 15.6 | 4.2 |
| 17.8 | 2.3 |
| 19.6 | 4.6 |
| 20.4 | 30.2 |
| 21.1 | 2.8 |
| 21.7 | 5.6 |
| 22.7 | 34.0 |
| 23.6 | 1.4 |
| 24.2 | 3.7 |
| 24.5 | 9.4 |
| 24.7 | 24.6 |
| 26.1 | 0.9 |
| 26.9 | 4.9 |
| 27.5 | 7.6 |
| 28.9 | 1.0 |
| 29.1 | 4.0 |
| 30.5 | 1.8 |

TABLE 2-continued

| XRPD peak table for Form II of Compound 1. | |
|---|---|
| 2θ (°) | Rel. intensity (%) |
| 31.6 | 3.9 |
| 33.9 | 1.7 |
| 34.4 | 1.3 |

Example 3. Preparation and Characterization of Crystalline Form III of Compound 1

Crystalline Form I was weighed into a sample vial, and 50 V of acetone was then added to slurry at 50° C. for 1 day. Solids were filtered, collected and dried at 50° C. overnight. Besides, crystalline Form III can also be directly obtained by following the purification procedure of above synthetic step 4.

The resulting solids were characterized by means of XRPD, DSC, TGA and DVS, with XRPD spectrum shown in FIG. 3*a*, and its main diffraction peaks and their relative intensities shown in Table 3. DSC and TGA profiles are shown in FIG. 3*b*. The DSC profile shows a weak endothermic peak at 272° C. and strong ones at 310° C. and 318° C. The TGA profile shows that there is no apparent weight loss in crystalline Form III at a temperature range from RT to 250° C. DVS results in FIG. 3*c* show that the hygroscopic weight gain of Form III at 90% RH is 0.13%.

TABLE 3

| XRPD peak table for Form III of Compound 1. | |
|---|---|
| 2θ (°) | Rel. intensity (%) |
| 5.9 | 3.8 |
| 7.0 | 84.6 |
| 8.5 | 4.4 |
| 9.7 | 100.0 |
| 14.1 | 32.2 |
| 14.5 | 19.2 |
| 16.0 | 7.4 |
| 17.2 | 17.3 |
| 17.7 | 4.2 |
| 18.2 | 33.1 |
| 19.3 | 4.3 |
| 19.6 | 13.4 |
| 19.9 | 3.9 |
| 20.5 | 2.4 |
| 21.3 | 49.1 |
| 21.6 | 4.9 |
| 22.1 | 5.2 |
| 22.9 | 10.1 |
| 23.2 | 2.5 |
| 23.9 | 5.3 |
| 24.1 | 24.7 |
| 25.3 | 2.9 |
| 25.7 | 3.2 |
| 26.0 | 11.3 |
| 27.0 | 29.3 |
| 28.0 | 1.5 |
| 28.5 | 6.1 |
| 29.0 | 3.2 |
| 29.3 | 9.6 |
| 29.8 | 3.1 |
| 30.8 | 0.9 |
| 31.5 | 1.8 |
| 32.4 | 1.5 |
| 33.8 | 1.7 |
| 34.7 | 1.5 |
| 35.0 | 1.9 |
| 35.7 | 3.1 |
| 36.6 | 2.4 |
| 37.0 | 10.2 |

Example 4. Preparation and Characterization of Crystalline Form IV of Compound 1

Crystalline Form I was weighed into a sample vial, and 50 V of acetonitrile was then added to slurry at 50° C. for 1 day. Solids were filtered, collected and dried at 50° C. under vacuum for 6 hours.

The resulting solids were characterized by means of XRPD, DSC and TGA, with XRPD spectrum shown in FIG. 4*a*, and its main diffraction peaks and their relative intensities shown in Table 4. DSC and TGA profiles are shown in FIG. 4*b*. The DSC profile shows a weak exothermic peak at 216° C. and a strong endothermic peak at 319° C. The TGA profile shows that there is no apparent weight loss in crystalline Form IV at a temperature range from RT to 275° C.

TABLE 4

| XRPD peak table for Form IV of Compound 1. | |
|---|---|
| 2θ (°) | Rel. intensity (%) |
| 5.6 | 100.0 |
| 6.7 | 1.9 |
| 7.6 | 56.1 |
| 10.6 | 1.8 |
| 10.9 | 4.3 |
| 11.3 | 40.4 |
| 14.2 | 1.9 |
| 15.2 | 6.3 |
| 15.7 | 1.9 |
| 18.0 | 4.9 |
| 21.0 | 12.0 |
| 21.7 | 6.1 |
| 22.8 | 32.5 |
| 23.3 | 1.6 |
| 24.0 | 5.4 |
| 25.3 | 3.9 |
| 26.0 | 3.5 |
| 26.8 | 7.4 |
| 27.2 | 2.5 |
| 34.5 | 2.9 |
| 38.0 | 1.9 |

Example 5. Preparation and Characterization of Crystalline Form V of Compound 1

Crystalline Form I was heated to 300° C.,

The resulting solids were characterized by means of XRPD, DSC and TGA, with XRPD spectrum shown in FIG. 5*a*, and its main diffraction peaks and their relative intensities shown in Table 5. DSC and TGA profiles are shown in FIG. 5*b*. The DSC profile shows a strong endothermic peak at 319° C. The TGA profile shows that there is no apparent weight loss in crystalline Form V when heated to 275° C.

TABLE 5

| XRPD peak table for Form V of Compound 1. | |
|---|---|
| 2θ (°) | Rel. intensity (%) |
| 4.8 | 9.9 |
| 7.1 | 2.0 |
| 8.7 | 91.4 |
| 9.7 | 100.0 |
| 10.3 | 3.7 |
| 12.6 | 11.0 |
| 13.6 | 3.0 |
| 14.7 | 11.6 |
| 17.6 | 23.0 |

TABLE 5-continued

| XRPD peak table for Form V of Compound 1. | |
|---|---|
| 2θ (°) | Rel. intensity (%) |
| 17.8 | 4.2 |
| 18.6 | 2.3 |
| 19.6 | 4.0 |
| 20.8 | 57.5 |
| 21.7 | 2.0 |
| 22.1 | 3.6 |
| 22.5 | 3.3 |
| 23.4 | 1.0 |
| 24.6 | 20.5 |
| 24.9 | 4.5 |
| 25.5 | 15.0 |
| 26.5 | 4.4 |
| 27.4 | 7.2 |
| 27.6 | 8.6 |
| 28.1 | 5.8 |
| 29.4 | 1.6 |
| 31.6 | 1.7 |
| 36.0 | 1.1 |
| 36.4 | 1.9 |

Example 6. Preparation and Characterization of Crystalline Form VI of Compound 1

Crystalline Form I was weighed into a sample vial, and 50 V of water was then added to slurry at 50° C. for 1 day. Solids were filtered, collected and dried at RT.

The resulting solids were characterized by means of XRPD, DSC and TGA, with XRPD spectrum shown in FIG. 6*a*, and its main diffraction peaks and their relative intensities shown in Table 6. DSC and TGA profiles are shown in FIG. 6*b*. The DSC profile shows two strong endothermic peaks at 49° C. and 319° C., respectively. The TGA profile shows a weight loss of about 7.3% at a temperature range from 30° C. to 70° C. Form VI may be dihydrate of Compound 1 (a theoretical water content of 7.8%).

TABLE 6

| XRPD peak table for Form VI of Compound 1. | |
|---|---|
| 2θ (°) | Rel. intensity (%) |
| 5.8 | 4.8 |
| 7.2 | 100.0 |
| 11.0 | 7.6 |
| 13.3 | 12.5 |
| 14.5 | 14.1 |
| 17.8 | 6.6 |
| 20.2 | 1.1 |
| 20.8 | 1.6 |
| 21.1 | 0.8 |
| 21.7 | 6.1 |
| 21.9 | 10.3 |
| 22.2 | 41.8 |
| 23.6 | 3.2 |
| 23.9 | 0.7 |
| 24.6 | 8.0 |
| 25.0 | 5.7 |
| 26.1 | 0.7 |
| 26.8 | 5.6 |
| 27.1 | 10.3 |
| 27.4 | 11.2 |
| 28.5 | 1.5 |
| 29.1 | 3.0 |
| 29.4 | 5.2 |
| 32.7 | 2.3 |
| 33.4 | 3.6 |
| 35.0 | 1.5 |
| 35.9 | 0.9 |
| 39.8 | 2.7 |

Example 7. Preparation and Characterization of Crystalline Form VII of Compound 1

Crystalline Form I was weighed into a sample vial, and 50 V of ethyl acetate was then added to slurry at 50° C. for 1 day. Solids were filtered, collected and dried at 50° C. under vacuum overnight.

The resulting solids were characterized by means of XRPD, DSC and TGA, with XRPD spectrum shown in FIG. 7*a*, and its main diffraction peaks and their relative intensities shown in Table 7. DSC and TGA profiles are shown in FIG. 7*b*. The DSC profile shows multiple exo- and endothermic peaks, with an exothermic peak at 135° C. and endothermic peaks at 72° C., 237° C., 283° C. and 318° C. The TGA profile shows a weight loss of about 2.6% at a temperature range from RT to 130° C.

TABLE 7

| XRPD peak table for Form VII of Compound 1. | |
|---|---|
| 2θ (°) | Rel. intensity (%) |
| 6.1 | 100.0 |
| 6.6 | 63.6 |
| 6.9 | 47.2 |
| 7.5 | 22.8 |
| 9.4 | 22.0 |
| 12.2 | 7.9 |
| 13.5 | 7.0 |
| 13.9 | 16.7 |
| 16.5 | 7.5 |
| 16.9 | 7.1 |
| 17.3 | 6.4 |
| 18.1 | 9.6 |
| 18.7 | 15.8 |
| 19.6 | 3.9 |
| 20.9 | 15.4 |
| 22.0 | 12.6 |
| 22.7 | 26.4 |
| 23.1 | 7.8 |
| 23.7 | 13.2 |
| 24.6 | 4.4 |
| 26.4 | 11.3 |
| 27.3 | 11.5 |
| 27.6 | 22.0 |
| 28.2 | 5.4 |
| 30.0 | 6.9 |
| 31.0 | 3.7 |
| 31.7 | 3.3 |
| 35.4 | 4.8 |

Example 8. Preparation and Characterization of Crystalline Form VIII of Compound 1

Crystalline Form VII was heated to 200° C.

The resulting solids were characterized by means of XRPD, DSC and TGA, with XRPD spectrum shown in FIG. 8*a*, and its main diffraction peaks and their relative intensities shown in Table 8. DSC and TGA profiles are shown in FIG. 8*b*. The DSC profile shows an exothermic peak at 303° C. and a strong endothermic peak at 319° C. The TGA profile shows that there is no apparent weight loss at a temperature range from RT to 130° C.

TABLE 8

| XRPD peak table for Form VIII of Compound 1. | |
|---|---|
| 2θ (°) | Rel. intensity (%) |
| 6.7 | 100.0 |
| 7.4 | 22.8 |
| 9.4 | 67.6 |

TABLE 8-continued

| XRPD peak table for Form VIII of Compound 1. | |
|---|---|
| 2θ (°) | Rel. intensity (%) |
| 13.6 | 22.4 |
| 14.3 | 4.6 |
| 15.4 | 3.7 |
| 17.3 | 5.3 |
| 18.7 | 6.3 |
| 19.0 | 5.8 |
| 20.8 | 20.4 |
| 21.9 | 6.0 |
| 23.6 | 9.2 |
| 35.7 | 5.6 |

Example 9. Preparation and Characterization of Crystalline Form IX of Compound 1

About 40 mg of crystalline Form I was weighed, and dimethyl sulfoxide (DMSO) was added to dissolve it at 50° C. The solution was filtered and placed at room temperature for cooling crystallization. Solids were filtered, collected and dried at 50° C. under vacuum for 6 hours.

The resulting solids were characterized by means of XRPD, DSC and TGA, with XRPD spectrum shown in FIG. 9*a*, and its main diffraction peaks and their relative intensities shown in Table 9. DSC and TGA profiles are shown in FIG. 9*b*. The DSC profile shows two endothermic peaks at 138° C. and 319° C., respectively. The TGA profile shows a weight loss of about 15.2% at a temperature range from 50° C. to 170° C. The crystalline Form IX should be a mono-DMSO solvate of Compound 1 (a theoretical DMSO content of 15.4%).

TABLE 9

| XRPD peak table for Form IX of Compound 1. | |
|---|---|
| 2θ (°) | Rel. intensity (%) |
| 6.2 | 5.1 |
| 7.2 | 100.0 |
| 9.5 | 3.0 |
| 11.4 | 1.4 |
| 12.6 | 6.0 |
| 14.5 | 0.6 |
| 16.7 | 3.1 |
| 17.2 | 0.5 |
| 18.9 | 8.9 |
| 19.2 | 5.0 |
| 19.9 | 1.4 |
| 21.2 | 11.4 |
| 22.0 | 17.8 |
| 22.2 | 2.8 |
| 23.1 | 11.1 |
| 24.7 | 0.9 |
| 25.4 | 4.5 |
| 25.7 | 1.5 |
| 26.6 | 1.7 |
| 29.0 | 1.0 |
| 30.8 | 2.6 |
| 31.9 | 1.1 |
| 37.3 | 2.2 |

Example 10. Preparation and Characterization of Crystalline Form X of Compound 1

Crystalline Form IX was heated to 200° C.,

The resulting solids were characterized by means of XRPD, DSC and TGA, with XRPD spectrum shown in FIG. 10*a*, and its main diffraction peaks and their relative intensities shown in Table 10. DSC and TGA profiles are shown in FIG. 10*b*. The DSC profile shows endothermic peaks at 300° C. and 319° C. The TGA profile shows that there is no apparent weight loss when heated to 250° C.

TABLE 10

| XRPD peak table for Form X of Compound 1. | |
|---|---|
| 2θ (°) | Rel. intensity (%) |
| 7.4 | 100.0 |
| 7.9 | 42.6 |
| 9.4 | 6.7 |
| 11.7 | 16.3 |
| 20.7 | 16.6 |
| 22.0 | 4.9 |
| 22.6 | 6.1 |
| 23.6 | 13.7 |
| 26.4 | 6.4 |

Example 11. Preparation and Characterization of Crystalline Form XI of Compound 1

About 20 mg of crystalline Form I was dissolved in 1 mL of dimethyl formamide at 50° C. 4 ml, of isopropanol was gradually added until solids were precipitated. The solids were slurried at 50° C. overnight, and then filtered, collected and dried at 50° C. under vacuum overnight.

The resulting solids were characterized by means of XRPD, DSC and TGA, with XRPD spectrum shown in FIG. 11*a*, and its main diffraction peaks and their relative intensities shown in Table 11. DSC and TGA profiles are shown in FIG. 11*b*. The DSC profile shows an exothermic peak at 211° C. and endothermic ones at 104° C. and 319° C. The TGA profile shows a weight loss of about 4.1% when heated to 140° C.

TABLE 11

| XRPD peak table for Form XI of Compound 1. | |
|---|---|
| 2θ (°) | Rel. intensity (%) |
| 5.6 | 59.3 |
| 6.0 | 89.4 |
| 6.4 | 56.6 |
| 7.5 | 100.0 |
| 7.7 | 79.6 |
| 9.8 | 7.7 |
| 10.9 | 4.6 |
| 11.3 | 38.5 |
| 12.1 | 41.4 |
| 12.2 | 60.1 |
| 12.8 | 8.3 |
| 14.2 | 4.1 |
| 15.1 | 15.3 |
| 15.6 | 13.2 |
| 17.1 | 4.0 |
| 17.8 | 19.5 |
| 18.0 | 8.3 |
| 19.0 | 49.9 |
| 20.4 | 2.9 |
| 21.0 | 13.3 |
| 21.6 | 14.9 |
| 22.5 | 7.2 |
| 22.7 | 46.2 |
| 23.2 | 6.8 |
| 23.6 | 16.9 |
| 24.0 | 11.3 |
| 24.3 | 26.3 |
| 25.0 | 37.6 |
| 25.5 | 12.9 |

TABLE 11-continued

| XRPD peak table for Form XI of Compound 1. | |
|---|---|
| 2θ (°) | Rel. intensity (%) |
| 26.0 | 10.7 |
| 26.7 | 20.7 |
| 27.2 | 5.3 |
| 28.9 | 6.3 |
| 31.6 | 5.0 |
| 34.4 | 5.6 |
| 38.0 | 5.0 |

Example 12. Preparation and Characterization of Crystalline Form XII of Compound 1

About 20 mg of crystalline Form I was dissolved in 1 mL of dimethyl formamide at 50° C. 4 mL of acetone was gradually added until solids were precipitated. The solids were slurried at 50° C. overnight, and then filtered, collected and dried at 50° C. under vacuum overnight.

The resulting solids were characterized by means of XRPD, DSC and TGA with XRPD spectrum shown in FIG. 12*a*, and its main diffraction peaks and their relative intensities shown in Table 12. DSC and TGA profiles are shown in FIG. 12*b*. The DSC profile shows an exothermic peak at 205° C. and endothermic ones at 124° C. and 319° C. The TGA profile shows a weight loss of about 4.1% when heated to 120° C. and a further weight loss of about 2.1% at a temperature range from more than 120° C. to 230° C.,

TABLE 12

| XRPD peak table for Form XII of Compound 1. | |
|---|---|
| 2θ (°) | Rel. intensity (%) |
| 5.9 | 100.0 |
| 6.4 | 83.7 |
| 7.0 | 21.7 |
| 8.7 | 33.3 |
| 9.3 | 3.2 |
| 11.0 | 23.7 |
| 11.9 | 26.8 |
| 12.8 | 5.5 |
| 13.5 | 23.6 |
| 14.1 | 7.4 |
| 15.6 | 12.8 |
| 16.2 | 21.7 |
| 19.3 | 46.8 |
| 19.5 | 62.9 |
| 20.2 | 21.8 |
| 21.3 | 12.0 |
| 22.2 | 7.8 |
| 23.2 | 7.4 |
| 24.0 | 32.0 |
| 24.5 | 18.5 |
| 24.9 | 24.8 |
| 26.1 | 9.6 |
| 27.4 | 7.5 |
| 28.1 | 7.7 |
| 32.9 | 3.7 |
| 34.7 | 4.2 |

Example 13. Preparation and Characterization of Crystalline Form XIII of Compound 1

Crystalline Form I was weighed into a sample vial, and 50 V of methanol was then added to slurry at RT for 3 days. Solids were filtered, collected and dried.

The resulting solids were characterized by means of XRPD, DSC and TGA, with XRPD spectrum shown in FIG. 13*a*, and its main diffraction peaks and their relative intensities shown in Table 13, DSC and TGA profiles are shown in FIG. 13*b*. The DSC profile shows an endothermic peak at 319° C. The TGA profile shows that there is no apparent weight loss when heated to 250° C.

TABLE 13

| XRPD peak table for Form XIII of Compound 1. | |
|---|---|
| 2θ (°) | Rel. intensity (%) |
| 5.5 | 2.8 |
| 7.4 | 11.9 |
| 7.8 | 100.0 |
| 8.7 | 4.4 |
| 9.7 | 12.5 |
| 11.2 | 6.8 |
| 12.6 | 1.5 |
| 15.6 | 14.9 |
| 18.7 | 3.1 |
| 20.8 | 7.2 |
| 22.2 | 9.4 |
| 22.6 | 5.7 |
| 25.6 | 2.3 |
| 26.2 | 1.7 |
| 27.2 | 0.9 |
| 30.3 | 1.4 |
| 31.7 | 2.1 |

Example 14. Preparation and Characterization of Crystalline Form XIV of Compound 1

Crystalline Form I was weighed into a sample vial, and 50 V of isopropanol was then added to slurry at RT for 3 days. Solids were filtered, collected and dried.

The resulting solids were characterized by means of XRPD, DSC and TGA, with XRPD spectrum shown in FIG. 14*a*, and its main diffraction peaks and their relative intensities shown in Table 14. DSC and TGA profiles are shown in FIG. 14*b*, The DSC profile shows two endothermic peaks at 237° C. and 319° C., The TGA profile shows that there is no apparent weight loss when heated to 250° C.

TABLE 14

| XRPD peak table for Form XIV of Compound 1. | |
|---|---|
| 2θ (°) | Rel. intensity (%) |
| 5.5 | 29.1 |
| 8.6 | 25.5 |
| 10.3 | 9.1 |
| 11.1 | 36.1 |
| 12.4 | 4.4 |
| 15.6 | 8.5 |
| 16.9 | 3.5 |
| 17.5 | 16.4 |
| 19.8 | 8.1 |
| 20.8 | 100.0 |
| 23.1 | 5.9 |
| 23.4 | 4.2 |
| 25.1 | 2.7 |
| 26.4 | 9.6 |
| 27.9 | 3.3 |
| 30.8 | 2.6 |
| 31.5 | 4.6 |
| 33.1 | 4.9 |

Example 15. Preparation and Characterization of Crystalline Form XV of Compound 1

Crystalline Form I was weighed into a sample vial, and 50 V of tetrahydrofuran was then added to slurry at RT for 3 days. Solids were filtered, collected and dried.

The resulting solids were characterized by means of XRPD, DSC and TGA, with XRPD spectrum shown in FIG. 15*a*, and its main diffraction peaks and their relative intensities shown in Table 15. DSC and TGA profiles are shown in FIG. 15*b*. The DSC profile shows a weak exothermic peak at 253° C. and endothermic ones at 285° C. and 319° C. The TGA profile shows a weight loss of about 0.7% when heated to 250° C.

TABLE 15

XRPD peak table for Form XV of Compound 1.

| 2θ (°) | Rel. intensity (%) |
|---|---|
| 6.6 | 2.8 |
| 7.5 | 13.8 |
| 7.8 | 100.0 |
| 9.3 | 14.1 |
| 11.2 | 1.7 |
| 12.9 | 3.2 |
| 15.1 | 1.1 |
| 15.8 | 2.6 |
| 16.2 | 1.5 |
| 17.6 | 1.4 |
| 19.8 | 3.6 |
| 20.5 | 6.2 |
| 21.5 | 11.1 |
| 22.4 | 14.8 |
| 24.3 | 2.6 |
| 26.5 | 3.1 |
| 35.8 | 2.2 |

Example 16. Preparation and Characterization of Crystalline Form XVI of Compound 1

Crystalline Form IV was heated to 230° C.

The resulting solids were characterized by means of XRPD, DSC and TGA, with XRPD spectrum shown in FIG. 16*a*, and its main diffraction peaks and their relative intensities shown in Table 16. DSC and TGA profiles are shown in FIG. 16*b*. The DSC profile shows a weak exothermic peak at 137° C. and endothermic ones at 259° C. and 319° C., The TGA profile shows that there is no apparent weight loss when heated to 250° C.

TABLE 16

XRPD peak table for Form XVI of Compound 1.

| 2θ (°) | Rel. intensity (%) |
|---|---|
| 6.9 | 9.6 |
| 7.2 | 16.4 |
| 7.9 | 100.0 |
| 9.4 | 32.5 |
| 11.8 | 4.7 |
| 12.1 | 4.5 |
| 14.0 | 2.7 |
| 14.4 | 1.5 |
| 15.9 | 8.4 |
| 16.7 | 15.8 |
| 20.4 | 7.2 |
| 21.1 | 12.3 |
| 21.5 | 5.1 |
| 21.9 | 3.7 |
| 22.5 | 5.8 |
| 24.0 | 4.8 |
| 24.6 | 4.4 |
| 26.0 | 39.9 |
| 31.5 | 2.3 |
| 32.2 | 3.0 |
| 32.7 | 3.7 |
| 36.2 | 2.7 |

Example 16B. Preparation and Characterization of Crystalline Form XVII of Compound 1

15 mg of crystalline Form III was dissolved in 1 mL DCM containing 10% acetic acid. The suspensions were kept shaking at RT for 24 h. The solids were centrifuged and dried at 60° C. in oven for 3 h.

The resulting solids were characterized by means of XRPD, DSC, TGA and $^{1}$H-NMR, with XRPD spectrum shown in FIG. 16B-a, and its main diffraction peaks and their relative intensities shown in Table 16B, DSC and TGA profiles are shown in FIG. 16B-b. The DSC profile shows an obvious endothermic peak at 156.6° C. The TGA profile shows that there is around 12.0% weight loss from RT to 180° C. $^{1}$H-NMR spectrum in FIG. 16B-c exhibits the molar ratio of Compound 1 to acetic acid is about 1:1. As the theoretical content of acetic acid in the mono-acetic acid solvate is 12.3%, crystalline Form XVII can be mono-acetic acid solvate of Compound 1.

TABLE 16B

XRPD peak table for Form XVII of Compound 1.

| 2θ (°) | Rel. intensity (%) |
|---|---|
| 6.1 | 40.3 |
| 7.3 | 22.0 |
| 8.8 | 33.1 |
| 10.4 | 18.2 |
| 12.0 | 97.4 |
| 14.7 | 24.1 |
| 15.5 | 4.8 |
| 16.4 | 16.0 |
| 17.7 | 25.2 |
| 18.4 | 10.0 |
| 19.1 | 26.6 |
| 19.5 | 24.3 |
| 19.9 | 7.2 |
| 20.9 | 38.2 |
| 22.2 | 21.1 |
| 22.7 | 100.0 |
| 23.6 | 7.4 |
| 24.3 | 37.1 |
| 24.6 | 21.3 |
| 25.2 | 14.6 |
| 25.6 | 22.0 |
| 26.7 | 23.9 |
| 27.9 | 6.8 |
| 28.7 | 3.2 |
| 29.9 | 12.1 |
| 30.5 | 8.1 |

Example 17. Preparation and Characterization of Sulfate Form a of Compound 1

Crystalline Form I was weighed into a sample vial, and 120 V of ethanol and 1 eq of sulfuric acid were added to slurry at RT for 1 day. Solids were filtered, collected and dried.

The resulting solids were characterized by means of XRPD, DSC, TGA, IC and DVS, with XRPD spectrum shown in FIG. 17*a*, and its main diffraction peaks and their relative intensities shown in Table 17. DSC and TGA profiles are shown in FIG. 17*b*. The DSC profile shows two endothermic peaks at 198° C. and 226° C., respectively. The TGA profile shows a weight loss of about 1.6% when heated to 176° C. The results of ion chromatography (IC) show a sulfate content of 16.7%. The DVS results shown in FIG. 17*c* indicate that sulfate Form A was hygroscopic with about 10% water uptake at 90% RH. It is supposed that the sulfate Form A has a molar ratio of Compound 1 and sulfuric acid of 1:1.

TABLE 17

| XRPD peak table for sulfate Form A of Compound 1. | |
|---|---|
| 2θ (°) | Rel. intensity (%) |
| 6.2 | 3.4 |
| 7.2 | 100.0 |
| 9.5 | 3.3 |
| 11.4 | 2.2 |
| 12.5 | 3.9 |
| 14.6 | 1.3 |
| 16.7 | 3.4 |
| 17.2 | 1.2 |
| 18.4 | 0.5 |
| 18.9 | 9.2 |
| 19.2 | 7.1 |
| 19.9 | 1.2 |
| 21.2 | 16.2 |
| 22.0 | 26.9 |
| 22.2 | 3.6 |
| 23.0 | 18.6 |
| 24.7 | 2.2 |
| 25.0 | 1.7 |
| 25.3 | 4.6 |
| 25.7 | 2.5 |
| 26.7 | 4.9 |
| 27.5 | 0.8 |
| 28.3 | 0.9 |
| 28.8 | 1.3 |
| 29.0 | 1.6 |
| 30.4 | 1.2 |
| 30.8 | 3.8 |
| 31.3 | 1.0 |
| 31.9 | 2.1 |
| 32.8 | 0.7 |
| 33.8 | 0.7 |
| 34.1 | 1.0 |
| 34.8 | 0.9 |
| 37.3 | 3.3 |
| 37.7 | 1.4 |

Example 18. Preparation and Characterization of Sulfate Form B of Compound 1

Crystalline Form I was weighed into a sample vial, and 120 V of acetone was added to form a suspension. 1 eq of sulfuric acid was added to slurry at RT for 3 days. Solids were filtered, collected and dried at 50° C. under vacuum.

The resulting solids were characterized by means of XRPD, DSC, TG A, IC and DVS, with XRPD spectrum shown in FIG. 18*a*, and its main diffraction peaks and their relative intensities shown in Table 18. DSC and TGA profiles are shown in Figure (% b. The DSC profile shows a strong endothermic peak around 250° C., The TGA profile shows that there is no apparent weight loss when heated to 200° C. The IC results show a sulfate content of 18.7%. The DVS results shown in FIG. 18*c* indicate that sulfate Form B was hygroscopic with about 1.0% water uptake at 90% RH. It is supposed that the sulfate Form B has a molar ratio of Compound 1 and sulfuric acid of 1:1.

TABLE 18

| XRPD peak table for sulfate Form B of Compound 1. | |
|---|---|
| 2θ (°) | Rel. intensity (%) |
| 5.9 | 18.0 |
| 6.6 | 7.5 |
| 7.3 | 100.0 |
| 10.2 | 30.0 |
| 11.6 | 52.4 |
| 11.9 | 31.5 |
| 12.8 | 49.5 |
| 13.4 | 7.0 |
| 14.8 | 69.9 |
| 17.0 | 6.1 |
| 17.9 | 3.3 |
| 18.6 | 12.7 |
| 19.1 | 3.1 |
| 19.9 | 1.9 |
| 20.1 | 4.0 |
| 20.6 | 52.2 |
| 21.1 | 4.7 |
| 22.3 | 65.7 |
| 22.7 | 24.7 |
| 23.4 | 38.2 |
| 25.8 | 74.1 |
| 26.6 | 7.8 |
| 27.0 | 8.8 |
| 27.2 | 10.2 |
| 28.6 | 1.3 |
| 29.1 | 1.4 |
| 29.5 | 0.8 |
| 30.0 | 2.4 |
| 31.2 | 1.3 |
| 32.1 | 2.4 |
| 32.9 | 14.4 |
| 33.9 | 6.8 |
| 34.9 | 1.4 |
| 36.4 | 1.5 |
| 37.0 | 1.1 |
| 39.5 | 2.2 |

Example 19. Preparation and Characterization of Sulfate Form C of Compound 1

The sample was collected after DVS test of sulfate Form A.

The resulting solids were characterized by means of XRPD, DSC and TG A, with XRPD spectrum shown in FIG. 19*a*, and its main diffraction peaks and their relative intensifies shown in Table 19. DSC and TGA profiles are shown in FIG. 19*b*. The DSC profile shows endothermic peaks at 111° C., 196° C. and 230° C. and an exothermic peak at 209° C. The TGA profile shows a weight loss of about 3.3% when heated to 177° C. It is supposed that the sulfate Form C has a molar ratio of Compound 1 and sulfuric acid of 1:1.

TABLE 19

| XRPD peak table for sulfate Form C of Compound 1. | |
|---|---|
| 2θ (°) | Rel. intensity (%) |
| 4.4 | 18.5 |
| 7.5 | 27.3 |
| 8.9 | 55.5 |
| 9.7 | 12.8 |
| 11.7 | 11.0 |
| 13.2 | 14.4 |
| 13.5 | 15.5 |
| 14.0 | 47.7 |
| 14.5 | 54.2 |
| 16.0 | 12.7 |
| 16.6 | 7.9 |
| 17.6 | 44.1 |
| 18.0 | 31.9 |
| 18.8 | 5.6 |
| 19.5 | 100.0 |
| 20.3 | 18.8 |
| 21.3 | 29.8 |
| 21.7 | 31.2 |
| 21.9 | 25.1 |

TABLE 19-continued

| XRPD peak table for sulfate Form C of Compound 1. | |
|---|---|
| 2θ (°) | Rel. intensity (%) |
| 22.8 | 26.9 |
| 23.4 | 43.6 |
| 23.8 | 22.8 |
| 24.6 | 34.5 |
| 25.4 | 25.7 |
| 27.3 | 17.5 |
| 28.2 | 21.4 |
| 29.5 | 20.0 |
| 31.2 | 9.4 |
| 32.4 | 9.8 |
| 32.8 | 6.0 |

Example 20. Preparation and Characterization of Besylate Form D of Compound 1

Crystalline Form I was weighed into a sample vial, and 120 V of acetone was added to form a suspension. 1 eq of benzenesulfonic acid was added to slurry at RT for 20 hours, Solids were filtered, collected and dried at 50° C. under vacuum.

The resulting solids were characterized by means of XRPD, DSC and TGA, with XRPD spectrum shown in FIG. 20*a*, and its main diffraction peaks and their relative intensities shown in Table 20. DSC and TGA profiles are shown in FIG. 20*b*. The DSC profile shows two strong endothermic peaks within a range of 124-142° C. The TGA profile shows a weight loss of about 5.8% when heated to 170° C. It is supposed that the besylate Form D has a molar ratio of Compound 1 and benzenesulfonic acid of 1:1.

TABLE 20

| XRPD peak table for besylate Form D of Compound 1. | |
|---|---|
| 2θ (°) | Rel. intensity (%) |
| 5.9 | 7.3 |
| 6.3 | 38.5 |
| 6.9 | 11.2 |
| 7.7 | 100.0 |
| 8.2 | 79.1 |
| 9.7 | 18.7 |
| 12.7 | 18.8 |
| 13.9 | 16.0 |
| 14.7 | 17.4 |
| 16.6 | 2.7 |
| 17.7 | 6.3 |
| 18.3 | 4.7 |
| 18.6 | 12.7 |
| 19.5 | 1.8 |
| 20.3 | 2.5 |
| 21.2 | 8.3 |
| 24.1 | 1.8 |
| 24.8 | 5.2 |
| 25.1 | 6.7 |
| 26.0 | 2.6 |
| 26.5 | 1.9 |
| 28.6 | 4.2 |
| 38.9 | 2.2 |

Example 21. Preparation and Characterization of Phosphate Form E of Compound 1

Crystalline Form I was weighed into a sample vial, and 120 V of acetone was added to form a suspension. 1 eq of phosphoric acid was added to slurry at RT for 20 hours, Solids were filtered, collected and dried at 50° C. under vacuum.

The resulting solids were characterized by means of XRPD, DSC, TGA and DVS, with XRPD spectrum shown in FIG. 21*a*, and its main diffraction peaks and their relative intensities shown in Table 21. DSC and TGA profiles are shown in FIG. 21*b*. The DSC profile shows two endothermic peaks at 241° C. and 259° C., respectively. The TGA profile shows that there is no apparent weight loss when heated to 210° C. The DVS results shown in FIG. 21*e* indicate that phosphate Form E was hygroscopic with about 0.92% water uptake at 90% RH, It is supposed that the phosphate Form E has a molar ratio of Compound 1 and phosphoric acid of 1:1.

TABLE 21

| XRPD peak table for phosphate Form E of Compound 1. | |
|---|---|
| 2θ (°) | Rel. intensity (%) |
| 5.6 | 4.3 |
| 6.5 | 1.0 |
| 7.2 | 100.0 |
| 9.8 | 6.4 |
| 11.2 | 66.1 |
| 12.6 | 32.1 |
| 13.1 | 0.8 |
| 14.5 | 43.7 |
| 16.2 | 2.2 |
| 17.0 | 1.3 |
| 18.0 | 12.2 |
| 19.8 | 24.1 |
| 21.8 | 46.3 |
| 22.5 | 27.1 |
| 24.6 | 5.7 |
| 25.3 | 34.7 |
| 25.7 | 4.2 |
| 26.8 | 1.9 |
| 28.5 | 4.3 |
| 29.2 | 6.0 |
| 29.7 | 1.0 |
| 32.4 | 2.3 |
| 33.3 | 2.8 |
| 34.2 | 2.6 |

Example 22. Preparation and Characterization of Mesylate Form F of Compound 1

Crystalline Form I was weighed into a sample vial, and 120 V of ethanol was added to form a suspension. 1 eq of methane sulfuric acid was added to slurry at RT for 20 hours. Solids were filtered, collected and dried at 50° C. under vacuum.

The resulting solids were characterized by means of XRPD, DSC and TGA, with XRPD spectrum shown in FIG. 22*a*, and its main diffraction peaks and their relative intensities shown in Table 22. DSC and TGA profiles are shown in FIG. 22*b*. The DSC profile shows two strong endothermic peaks at 120° C. and 257° C., and two weak exothermic peaks at 183° C. and 221° C. The TGA profile shows a weight loss of about 5.9% when heated to 140° C. It is supposed that the mesylate Form F has a molar ratio of Compound 1 and methane sulfuric acid of 1:1.

TABLE 22

| XRPD peak table for mesylate Form F of Compound 1. | |
|---|---|
| 2θ (°) | Rel. intensity (%) |
| 6.1 | 3.4 |
| 6.9 | 6.4 |
| 7.3 | 7.7 |

TABLE 22-continued

XRPD peak table for mesylate Form F of Compound 1.

| 2θ (°) | Rel. intensity (%) |
|---|---|
| 8.5 | 100.0 |
| 11.5 | 2.2 |
| 12.2 | 1.0 |
| 13.8 | 11.4 |
| 14.0 | 1.6 |
| 14.3 | 1.4 |
| 14.7 | 1.6 |
| 15.6 | 1.1 |
| 16.3 | 0.7 |
| 17.2 | 6.4 |
| 17.6 | 1.0 |
| 18.1 | 1.8 |
| 19.5 | 1.4 |
| 20.5 | 3.7 |
| 21.2 | 2.5 |
| 22.3 | 8.4 |
| 22.6 | 12.3 |
| 23.2 | 3.8 |
| 23.6 | 1.9 |
| 23.8 | 1.8 |
| 24.3 | 0.7 |
| 24.9 | 1.1 |
| 26.1 | 2.3 |
| 26.3 | 2.3 |
| 26.5 | 1.9 |
| 27.8 | 4.6 |
| 29.1 | 3.6 |
| 30.5 | 0.6 |
| 31.2 | 3.2 |
| 32.7 | 0.9 |

Example 23. Preparation and Characterization of Mesylate Form G of Compound 1

Crystalline Form was weighed into a sample vial, and 120 V of acetone was added to form a suspension. 1 eq of methane sulfuric acid was added to slurry at RT for 20 hours. Solids were filtered, collected and dried at 50° C. under vacuum.

The resulting solids were characterized by means of XRPD, DSC and TGA, with XRPD spectrum shown in FIG. 23*a*, and its main diffraction peaks and their relative intensities shown in Table 23, DSC and TGA profiles are shown in FIG. 23*b*. The DSC spectrum shows two weak exothermic peaks at 114° C. and 185° C. The TGA spectrum shows a weight loss of about 9.2% when heated to 196° C. The $^{1}$H-NMR spectrum shown in FIG. 23*c* indicates that the molar ratio of methanesulfonic acid to free base is 1:1.

TABLE 23

XRPD peak table for mesylate Form G of Compound 1.

| 2θ (°) | Rel. intensity (%) |
|---|---|
| 7.1 | 100.0 |
| 8.5 | 36.6 |
| 13.9 | 11.7 |
| 14.1 | 4.9 |
| 17.0 | 1.6 |
| 17.5 | 5.0 |
| 19.5 | 0.9 |
| 20.6 | 12.5 |
| 21.4 | 15.3 |
| 22.2 | 11.0 |
| 23.2 | 2.5 |
| 24.3 | 1.9 |
| 27.5 | 0.8 |
| 28.3 | 3.1 |

TABLE 23-continued

XRPD peak table for mesylate Form G of Compound 1.

| 2θ (°) | Rel. intensity (%) |
|---|---|
| 28.7 | 6.3 |
| 31.2 | 1.8 |
| 34.5 | 2.6 |
| 36.1 | 1.1 |

Example 24. Preparation and Characterization of Potassium Salt Form H of Compound 1

Crystalline Form I was weighed into a sample vial, and 120 V of ethanol was added to form a suspension. 1 eq of potassium hydroxide was added to stir at 50° C. for 5 hours. Solids were filtered, collected and dried at 50° C. under vacuum.

The resulting solids were characterized by means of XRPD, DSC and TGA, with XRPD spectrum shown in FIG. 24*a*, and its main diffraction peaks and their relative intensities shown in Table 24. DSC and TGA profiles are shown in FIG. 24*b*. The DSC profile shows two endothermic peaks at 25° C. and 249° C., and an exothermic peak at 260° C. The TGA profile shows a weight loss of about 2.9% when heated to 120° C. It is supposed that the potassium salt Form H has a molar ratio of Compound 1 and potassium hydroxide of 1.1.

TABLE 24

XRPD peak table for potassium salt Form H of Compound 1.

| 2θ (°) | Rel. intensity (%) |
|---|---|
| 7.7 | 100.0 |
| 7.9 | 60.7 |
| 9.1 | 2.8 |
| 9.9 | 6.0 |
| 10.4 | 15.6 |
| 13.8 | 1.5 |
| 14.1 | 1.6 |
| 15.5 | 3.7 |
| 16.0 | 7.3 |
| 17.5 | 13.0 |
| 18.2 | 2.1 |
| 18.5 | 3.0 |
| 20.0 | 1.7 |
| 20.3 | 1.4 |
| 20.6 | 1.0 |
| 21.2 | 1.6 |
| 21.9 | 5.6 |
| 22.3 | 2.1 |
| 22.5 | 10.6 |
| 22.8 | 15.0 |
| 23.0 | 28.2 |
| 23.4 | 6.1 |
| 23.9 | 1.4 |
| 25.6 | 2.7 |
| 25.9 | 4.1 |
| 26.3 | 4.8 |
| 26.6 | 3.8 |
| 27.0 | 1.3 |
| 27.3 | 2.9 |
| 28.4 | 2.2 |
| 30.3 | 1.5 |
| 31.9 | 1.4 |
| 32.2 | 2.8 |
| 33.1 | 1.3 |
| 34.3 | 2.4 |
| 37.7 | 2.5 |
| 38.4 | 3.9 |

Example 25. Preparation and Characterization of Potassium Salt Form J of Compound 1

Crystalline Form I was weighed into a sample vial, and 100 V of DMSO was added to form a suspension. 1 eq of potassium hydroxide was added to slurry at RT for 16 hours. Solids were filtered, collected and dried at 50° C. under vacuum for 3 days.

The resulting solids were characterized by means of XRPD, DSC and TGA, with XRPD spectrum shown in FIG. 25*a*, and its main diffraction peaks and their relative intensities shown in Table 25. DSC and TGA profiles are shown in FIG. 25*b*. The DSC profile shows three endothermic peaks at 29° C., 154° C. and 217° C., respectively. The TGA profile shows a weight loss of about 10.4% when heated to 192° C. It is supposed that the potassium salt Form J has a molar ratio of Compound 1 and potassium hydroxide of 1:1.

TABLE 25

XRPD peak table for potassium salt Form J of Compound 1.

| 2θ (°) | Rel. intensity (%) |
|---|---|
| 10.0 | 65.3 |
| 11.6 | 14.0 |
| 11.9 | 31.5 |
| 14.8 | 3.5 |
| 14.9 | 2.9 |
| 16.2 | 24.1 |
| 18.2 | 9.8 |
| 18.7 | 17.5 |
| 19.1 | 100.0 |
| 19.5 | 6.2 |
| 20.2 | 6.6 |
| 20.8 | 22.0 |
| 21.5 | 8.6 |
| 21.9 | 37.2 |
| 22.2 | 17.3 |
| 22.5 | 25.1 |
| 22.8 | 6.7 |
| 23.5 | 46.1 |
| 23.7 | 40.9 |
| 24.0 | 7.2 |
| 24.4 | 9.8 |
| 24.7 | 9.2 |
| 24.9 | 5.2 |
| 26.3 | 5.7 |
| 26.7 | 3.6 |
| 26.9 | 20.7 |
| 27.6 | 1.7 |
| 28.1 | 27.5 |
| 28.5 | 9.0 |
| 28.9 | 5.1 |
| 29.2 | 6.8 |
| 29.5 | 6.2 |
| 30.2 | 4.3 |
| 30.4 | 4.5 |
| 30.8 | 5.6 |
| 31.3 | 5.1 |
| 31.9 | 6.5 |
| 32.1 | 7.4 |
| 32.4 | 3.9 |
| 32.6 | 4.5 |
| 33.6 | 3.8 |
| 33.8 | 4.5 |
| 34.1 | 3.2 |
| 34.7 | 16.7 |
| 35.8 | 2.7 |
| 36.1 | 3.6 |
| 36.5 | 3.1 |
| 37.4 | 6.9 |
| 38.0 | 7.3 |
| 38.8 | 2.2 |
| 39.1 | 7.6 |
| 39.7 | 4.7 |

Example 26. Preparation and Characterization of Choline Salt Form K of Compound 1

Crystalline Form I was weighed into a sample vial, and 3 ml, of acetone was added to form a suspension, which turned to be a clear solution by adding 1.05 eq of choline, 3 mL of n-heptane was then added to slurry at RT overnight. Solids were filtered, collected and dried at 50° C. under vacuum.

The resulting solids were characterized by means of XRPD, DSC, TGA and DVS, with XRPD spectrum shown in FIG. 26*a*, and its main diffraction peaks and their relative intensities shown in Table 26. DSC and TGA profiles are shown in FIG. 26*b*. The DSC profile shows two strong endothermic peaks at 26° C. and 185° C., respectively. The TGA profile shows a weight loss of about 6.5% when heated to 161° C. The DVS results shown in FIG. 26*c* indicate that choline salt Form K was hygroscopic with about 23% water uptake at 90% RH. It is supposed that the choline salt Form K has a molar ratio of Compound 1 and choline of 1:1.

TABLE 26

XRPD peak table for choline salt Form K of Compound 1.

| 2θ (°) | Rel. intensity (%) |
|---|---|
| 7.4 | 100.0 |
| 9.9 | 8.4 |
| 10.5 | 4.4 |
| 11.3 | 10.5 |
| 12.3 | 7.9 |
| 12.9 | 29.6 |
| 13.5 | 2.3 |
| 14.9 | 9.6 |
| 16.1 | 3.3 |
| 17.0 | 5.3 |
| 17.9 | 53.0 |
| 18.4 | 3.1 |
| 19.0 | 6.5 |
| 19.3 | 9.3 |
| 19.8 | 32.4 |
| 20.4 | 4.7 |
| 21.2 | 25.9 |
| 21.8 | 1.6 |
| 22.7 | 11.8 |
| 23.3 | 8.1 |
| 23.8 | 16.9 |
| 24.2 | 16.7 |
| 25.0 | 17.6 |
| 25.4 | 7.8 |
| 26.0 | 13.5 |
| 26.5 | 3.9 |
| 27.9 | 6.2 |
| 29.0 | 6.1 |
| 30.6 | 3.5 |
| 31.3 | 2.8 |
| 32.0 | 1.4 |
| 33.9 | 2.0 |

Example 27. Preparation and Characterization of Choline Salt Form L of Compound 1

Crystalline Form I was weighed into a sample vial, and 3 mL of tetrahydrofuran was added to form a suspension, which turned to be a clear solution by adding 1.05 eq of choline. 3 mL of n-heptane was then added to slurry at RT overnight. Solids were filtered, collected and dried at 50° C. under vacuum.

The resulting solids were characterized by means of XRPD, DSC, TGA and DVS, with XRPD spectrum shown in FIG. 27*a*, and its main diffraction peaks and their relative intensifies shown in Table 27. DSC and TGA profiles are shown in FIG. 27*b*. The DSC profile shows two strong endothermic peaks at 55° C. and 184° C., respectively. The TGA profile shows a weight loss of about 10% when heated to 138° C., The $^1$H-NMR spectrum shown in FIG. 27*c* indicates that the molar ratio of choline to free base is 1:1. It is supposed that the choline salt Form L has a molar ratio of Compound 1 and choline of 1:1.

TABLE 27

| XRPD peak table for choline salt Form L of Compound 1. | |
|---|---|
| 2θ (°) | Rel. intensity (%) |
| 7.2 | 16.0 |
| 7.4 | 14.4 |
| 7.7 | 1.5 |
| 9.9 | 52.1 |
| 11.1 | 18.9 |
| 12.3 | 15.8 |
| 12.8 | 7.6 |
| 13.2 | 24.8 |
| 13.5 | 2.3 |
| 14.2 | 3.7 |
| 14.8 | 4.6 |
| 15.6 | 13.7 |
| 16.0 | 1.1 |
| 16.8 | 27.4 |
| 17.0 | 20.4 |
| 17.7 | 7.9 |
| 18.4 | 12.6 |
| 18.9 | 3.4 |
| 19.9 | 51.5 |
| 20.6 | 15.0 |
| 20.7 | 19.6 |
| 20.9 | 17.8 |
| 21.2 | 12.0 |
| 21.9 | 52.3 |
| 22.3 | 9.6 |
| 22.5 | 11.4 |
| 23.2 | 29.5 |
| 23.6 | 100.0 |
| 24.1 | 8.3 |
| 24.3 | 7.8 |
| 24.8 | 5.2 |
| 25.3 | 8.6 |
| 25.5 | 21.3 |
| 25.9 | 13.3 |
| 26.4 | 2.2 |
| 27.7 | 11.4 |
| 29.0 | 5.5 |
| 29.2 | 5.0 |
| 30.3 | 5.3 |
| 31.2 | 3.7 |
| 31.7 | 3.8 |
| 32.0 | 2.2 |
| 32.6 | 0.9 |
| 35.0 | 4.0 |
| 37.1 | 1.4 |
| 37.4 | 2.7 |
| 37.9 | 1.0 |

Above all, 17 crystalline forms of Compound 1 in free form were obtained and characterized, wherein Forms I, II, III, IV, V, VIII, X, XIII, XIV, XV and XVI were anhydrates, Forms VI (di-hydrate) and VII (channel hydrate) were hydrates, and Forms IX, XI, XII and XVII are solvates, Besides, 11 crystalline salts of Compound 1 with different forms were obtained, including sulfate, phosphate, besylate, mesylate, potassium salt and choline salt.

Inter-conversion study among identified anhydrates (Form I, Form II, Form III, Form IV, Form V, Form VIII, Form X, Form XIII, Form XIV, Form XV) was conducted in different organic solvents between RT to 60° C. Results suggests Form III is the most stable anhydrate form between RT to 60° C.

The slurry bridging studies among Form I, Form III and Form VI under different water activities was performed to identify the critical water activity under both 25° C. and 50° C., Result shows Form III is more stable when the water activity is not more than 0.56 at 25° C. and 0.83 at 50° C., respectively.

Solubility of Form III is low and pH-dependent with higher solubility observed in Simulated Gastric Fluid (SGF), Solid stability result showed Form III was physically and chemically stable at 40° C./75% RH and 60° C. for 7 days, and the crystal form remained unchanged at 92.5% RH for 10 days. Physical properties of the lead form are presented in Table 28.

TABLE 28

| Physical Properties of Form III of Compound 1. | | |
|---|---|---|
| Solid form | | Free Form III |
| Purity | | 98.95 |
| Solvation | | Anhydrate |
| PLM | | Needle |
| XRPD | | High crystallinity |
| DSC Onset/Peak (° C.), ΔH (J/g) | | 272/281° C., 7 J/g [a] Peak 312/318° C. endo/endo melting/decomposition |
| TGA Wt. loss %/T (° C.) | | None/RT to 200° C. |
| DVS Wt. gain % | | 0.09%, 0-80% RH 0.03%, 80-90% RH Reversible |
| Solubility [b] (μg/mL) 0.5/2/24 h | FaSSIF | 1.1/1.1/1.3 |
| | FeSSIF | 2.6/3.4/4.1 |
| | SGF | 7.3/8.2/5.7 |
| Solid stability | 40° C./75% RH for 7 d | Chemically and physically stable |
| | 60° C. for 7 d | Chemically and physically stable |
| | 92.5% RH for 10 d | Physically stable |

Among the crystalline salts, sulfate Form B and phosphate Form E of Compound 1 are anhydrates and showed better physical properties than other crystalline salts. Like Form III of free form, sulfate Form B and phosphate Form E showed low solubility (<0.02 mg/mL) in bio-relevant media.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

If aspects of the invention are described as “comprising” a feature, embodiments also are contemplated “consisting of” or “consisting essentially of” the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. An amorphous form of a compound having the following formula, in its free

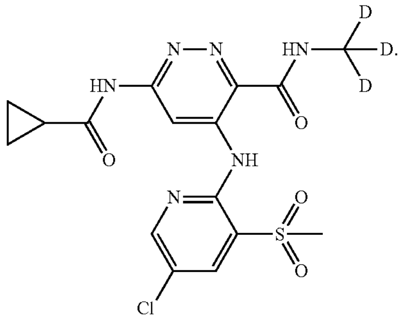

2. A pharmaceutical composition comprising the amorphous form of claim 1 and a pharmaceutically acceptable excipient.

3. A method of treating a disease or disorder in a subject in need thereof, the method comprising administering to the subject a pharmaceutical composition comprising a therapeutically effective amount of the amorphous form of claim 1, wherein the disease or disorder is one or more disease or disorder selected from multiple sclerosis, rheumatoid arthritis, inflammatory bowel disease, systemic lupus erythematosus, psoriasis, psoriatic arthritis, Crohn's Disease, Sjogren's syndrome and scleroderma.

4. The method of claim 3, wherein the disease or disorder is multiple sclerosis.

5. The method of claim 3, wherein the disease or disorder is rheumatoid arthritis.

6. The method of claim 3, wherein the disease or disorder is inflammatory bowel disease.

7. The method of claim 3, wherein the disease or disorder is systemic lupus erythematosus.

8. The method of claim 3, wherein the disease or disorder is psoriasis.

9. The method of claim 3, wherein the disease or disorder is psoriatic arthritis.

10. The method of claim 3, wherein the disease or disorder is Crohn's Disease.

11. The method of claim 3, wherein the disease or disorder is Sjogren's syndrome.

12. The method of claim 3, wherein the disease or disorder is scleroderma.

* * * * *